US008987422B2

(12) United States Patent
Delaney et al.

(10) Patent No.: US 8,987,422 B2
(45) Date of Patent: Mar. 24, 2015

(54) CD27L ANTIGEN BINDING PROTEINS

(71) Applicants: John M. Delaney, Bellevue, WA (US); William Christian Fanslow, III, Normandy Park, WA (US); Chadwick Terence King, North Vancouver (CA)

(72) Inventors: John M. Delaney, Bellevue, WA (US); William Christian Fanslow, III, Normandy Park, WA (US); Chadwick Terence King, North Vancouver (CA)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 13/623,836

(22) Filed: Sep. 20, 2012

(65) Prior Publication Data

US 2013/0078237 A1 Mar. 28, 2013

Related U.S. Application Data

(60) Provisional application No. 61/538,024, filed on Sep. 22, 2011.

(51) Int. Cl.
*C07K 16/30* (2006.01)
*C07K 16/46* (2006.01)
*C07K 16/28* (2006.01)
*A61K 47/48* (2006.01)

(52) U.S. Cl.
CPC ......... *C07K 16/2875* (2013.01); *C07K 2317/21* (2013.01); *C07K 2317/33* (2013.01); *C07K 2317/56* (2013.01); *C07K 2317/732* (2013.01); *C07K 2317/734* (2013.01); *C07K 2317/76* (2013.01); *C07K 2317/92* (2013.01); *C07K 2317/77* (2013.01); *A61K 47/48384* (2013.01); *A61K 47/48561* (2013.01)
USPC ............ 530/388.85; 530/388.73; 530/388.15; 530/391.7

(58) Field of Classification Search
CPC .. C07K 16/2875; C07K 16/46; C07K 16/461; C07K 16/464; C07K 2317/21; C07K 2317/24; C07K 16/468; A61K 47/48384; A61K 47/48561
See application file for complete search history.

(56) References Cited

U.S. PATENT DOCUMENTS

| 5,573,924 | A | 11/1996 | Beckmann et al. |
| 7,261,892 | B2 | 8/2007 | Terrett |
| 7,288,251 | B2 * | 10/2007 | Bedian et al. ............... 424/153.1 |
| 7,641,903 | B2 | 1/2010 | Law et al. |
| 8,101,724 | B2 * | 1/2012 | MacDonald et al. ...... 530/387.9 |
| 8,192,738 | B2 * | 6/2012 | Bedian et al. ............... 424/130.1 |
| 8,663,642 | B2 | 3/2014 | Law et al. |
| 2006/0246071 | A1 * | 11/2006 | Green et al. ................ 424/145.1 |

FOREIGN PATENT DOCUMENTS

| WO | 03/046581 A2 | 6/2003 |
| WO | WO2004/073656 A2 | 9/2004 |
| WO | WO2006/044643 A2 | 4/2006 |
| WO | WO2006/113909 A2 | 10/2006 |
| WO | WO2007/038637 A2 | 4/2007 |
| WO | WO2008/051424 A2 | 5/2008 |
| WO | WO2008/070593 A2 | 6/2008 |
| WO | WO2008/074004 A2 | 6/2008 |
| WO | WO2009/126934 A2 | 10/2009 |

OTHER PUBLICATIONS

Paul, Fundamental Immunology, 3rd Edition, 1993, pp. 292-295.*
Rudikoff et al., Proc. Nat'l Acad. Sci. USA 1982; 79:1979-83.*
Dall'Acqua et al., Methods 2005; 36:43-60.*
Lucy J. Holt, "Domain antibodies: proteins for therapy," pp. 484-490, Trends in Biotechnology, vol. 21, No. 11, Nov. 1, 2003.
Julian Davies, "Affinity improvement of single antibody VH domains: residues in all three hypervariable regions affect antigen binding," pp. 169-179, Immunotechnology, Elsevier Science, vol. 2, No. 3, Sep. 1, 1996.
Paul J. Carter, "Potent antibody therapeutics by design," pp. 343-357, Nature Reviews, Immunology, vol. 6, Apr. 7, 2006.
Kim L Wark, "Latest technolgies for the enhancement of antibody affinity," pp. 657-670, vol. 58, No. 5-6, Aug. 7, 2006.
Ansell et al. (Oct. 8, 2010), "Targeting CD70 in non-hodgkin lymphoma and renal cell carcinoma: a phase 1 study of the antibody-drug conjugate SGN-75", 35th ESMO Congress, Milan, Italy, poster abstract #532P.
Law et al. (Feb. 15, 2006), "Lymphocyte activation antigen CD70 expressed by renal cell carcinoma is a potential therapeutic target for anti-CD70 antibody-drug conjugates", Cancer Res., 66(4):2328-2337.
Smith et al. (Apr. 18, 2009), "CD70 expression in multiple types of carcinomas: new targets for auristatin-based anti-CD70 antibody-drug conjugate, SGN-75", Amer. Assoc, Cancer Res., Denver, Colorado, poster abstract #4652.

* cited by examiner

*Primary Examiner* — Sheela J Huff
*Assistant Examiner* — Jessica H Roark
(74) *Attorney, Agent, or Firm* — Joseph W. Bulock

(57) ABSTRACT

The present invention relates to CD27L antigen binding proteins, such an antibodies, polynucleotides encoding said CD27l antigen binding proteins, antibody drug conjugate compositions, and methods for diagnosing and treating diseases associated with CD27L expression.

29 Claims, 12 Drawing Sheets

| | Epitope Bin | Affinity Hu Biacore K$_D$ nM | Native cell Avidity EC50 nM | Cyno Avidity EC50 nM | ADCC EC50 nM | ADCP EC50 pM | CDC # EC50 nM | Internalization T ½ (hr) |
|---|---|---|---|---|---|---|---|---|
| Chimeric mouse anti-human CD27L | 3 | 1.25 | 0.60 | 2.22 | 0.195 | 2.17 | 2.64 | 0.41 |
| Ab1 | 1 | 0.62 | 0.32 | 0.05 | 0.021 | 1.12 | 1.0 | 1.03 |
| Ab2 | 1 | 0.59 | 0.24 | 0.24 | 0.034 | 1.19 | 1.17 | 0.69 |
| Ab3 | 1 | 4.35 | 4.18 | 2.80 | 0.715 | 64.8 | 10.6 | 0.49 |
| Ab4 | 3 | 3.05 | 0.25 | 0.48 | 0.332 | 1.55 | 1.54 | 0.30 |
| Ab5 | 2 | 10.4 | 0.66 | 1.40 | 0.422 | 2.36 | 5.28 | 0.75 |
| Ab6 | 4 | 6.06 | 0.87 | 0.87 | 0.167 | 1.88 | 4.20 | 1.08 |
| Ab7 | 4 | 0.71 | 0.18 | 0.43 | 0.076 | 0.80 | 0.64 | 0.43 |
| Ab8 | 2 | 10.8 | 0.09 | 0.34 | >67 | 1.60 | >67 | 1.81 |

FIG. 1

| Tumor Type | mRNA Expression | | Protein Expression | | | | |
|---|---|---|---|---|---|---|---|
| | | | IHC | | Flow Cytometry | | |
| | Literature | Amgen | Literature | Amgen | Literature | Amgen | |
| Clear cell renal cell carcinoma | | | | | | | |
| OCT embedded | 86% (n=6/7) | 90% (n=44/49) | 100% (n=41/41) | 100% (n=13/13) | | | |
| Fresh frozen | 100% (n=10/10) | 94% (n=44/47) | | | | n.d. | |
| FFPE | | | 82% (n=189/230) | | | | |
| B-NHL subsets (Frozen) | | | | | | | |
| Diffuse large B-cell lymphoma | 85% (n=335/414) | 100% (n=30/30) 100%(n=15/15) | 71% (n=15/21) | 67% (n=10/15) | | n.d. | |
| Follicular lymphoma | n.d. | 64% (n=21/33) 100% (n=10/10) | 33% (n=6/18) | 50% (n=5/10) | | n.d. | |
| Mantle cell lymphoma | n.d. | 100% (n=10/10) | 25% (n=1/4) | n.d. | | n.d. | |
| Chronic lymphocytic leukemia (Frozen) | n.d. | 75% (n=21/28) 90% (n=9/10) | 50% (n=3/6) | 50% (n = 5/10) | 90% (17/19) | 100% (11/11) | |

IHC = immunohistochemistry
qPCR = quantitative PCR
n.d. = not determined

Amgen mRNA results show; between 35 to 50% of SCCH&N (primarily ESO) and about 14% of ovarian patient samples express CD27L; 40% of papillary RCC express CD27L

FIG. 11

Linker: MCC: 4-[N-maleimidomethyl] cyclohexane-1-carboxylate (SMCC starting material)

CD27L ANTIGEN BINDING PROTEINS

RELATED APPLICATIONS

This application claims the benefit of U.S. Provisional Application No. 61/538,024 filed on Sep. 22, 2011, the contents of which are hereby incorporated by reference in their entirety.

The present application is being filed along with a Sequence Listing in electronic format. The Sequence Listing is provided as a file entitled A-1437-US-NP(US Non-Prov)_ST25.txt, created Sep. 17, 2012, which is 94.3 KB in size. The information in the electronic format of the Sequence Listing is incorporated herein by reference in its entirety.

FIELD OF THE INVENTION

The field of this invention relates to compositions of antigen binding proteins including antibodies capable of binding CD27L, as well as related methods.

BACKGROUND

CD27L (CD70, TNFSF7) is a type II integral membrane protein whose expression on normal tissues is highly restricted to a subset of activated T and B cells, dendritic cells and to a small subset of cells in the thymic epithelium. The biological functions of CD27L, which include augmentation or regulation of the immune response, are mediated via binding to its receptor, CD27, which is expressed predominately on lymphoid cells. CD27L/CD27 interactions regulate B-cell proliferation and differentiation and T-cell costimulation/activation. Disruption of the CD27L/CD27 interaction in mice deficient for CD27 does not result in any phenotype in the absence of an immune challenge. (Grewal, *Expert Opin. Ther. Targets.* 12, 341-351 (2008)).

In addition to its very restricted expression on normal tissues, CD27L is expressed at relatively high levels in some B cell non-Hodgkin's lymphoma (B-NHL) tumor sub-types, in pre-B cell acute lymphocytic leukemia (ALL) and in B cell type-chronic lymphocytic leukemia (B-CLL). Aberrant expression of CD27L is also observed in renal cell carcinoma (RCC) but not in normal kidney or other normal tissues. Thus, CD27L comes close to exhibiting properties consistent with those of a "tumor specific antigen" (Grewal, *Expert Opin. Ther. Targets.* 12, 341-351 (2008)).

Each year, of the approximately 49,000 patients that will develop RCC, a little over 40,000 of those will be diagnosed with ccRCC in the US (American Cancer Society: Cancer Facts and Figures final (2008). While some newer therapeutics have been approved for RCC over the last 4 years, the 5 year survival rate for patients with metastatic RCC remains dismal at 10-20% (National Caner Institute. SEER cancer statistics fact sheet: cancer of the kidney and renal pelvis—accessed 2008) and significant unmet medical need remains. The projected yearly number of newly diagnosed ccRCC patients (U.S.) that are expected to express CD27L is approximately 36,000. There are an estimated 64,000 ccRCC patients currently with active disease.

Of the B-cell malignancies reported to aberrantly express CD27L, the B-NHL subsets of diffuse large cell B-cell lymphoma (DLBCL) and follicular lymphoma (FL) show the highest incidence of expression ranging from 33% for FL to 71% for DLBCL as assessed by IHC on frozen sections using a validated antibody (Lens et al., *Brit. J. Hematol.* 106, 491-503 (1999). 50-89% of B-CLL tumors also express CD27L as assessed by IHC on frozen tumor sections or by flow cytometry on circulating tumor cells (Ranheim et al., *Blood* 85, 3556-3565 (1965); Trentin et al., *Cancer Res.* 57, 4940-4947 (1997)).

Of the 127,000 patients in the US currently with active B-NHL, approximately 50% of these patients present with the DLBCL (intermediate grade) sub-type (Morton et al., *Blood* 107, 265-276 (2002)). Despite Rituxan plus cyclophosphamide, adriamycin, vincristine, prednisone (CHOP) standard of care therapy for DLBCL patients, almost 50% relapse. Therefore an unmet medical need remains in this disease as well.

SUMMARY

The invention provides anti-CD27L antigen binding proteins, e.g., antibodies and functional fragments thereof. The anti-CD27L antigen binding proteins are particularly useful in methods of treating diseases and disorders associated with aberrant cell proliferation, e.g., cancer, and/or with inflammation.

In a first aspect, the CD27L antigen binding protein comprises a) a light chain variable domain having at least 90% identity, at least 95% identity, or is identical to the amino acid sequence set forth in SEQ ID NO:63, SEQ ID NO:64, SEQ ID NO:65, SEQ ID NO:66, SEQ ID NO:67, SEQ ID NO:68, SEQ ID NO:69, or SEQ ID NO:70; b) a heavy chain variable domain having at least 90% identity, at least 95% identity, or is identical to the amino acid sequence set forth in SEQ ID NO:17, SEQ ID NO:18, SEQ ID NO:19, SEQ ID NO:20, SEQ ID NO:21, SEQ ID NO:22, SEQ ID NO:23, or SEQ ID NO:24; or c) the light chain variable domain of a) and the heavy chain variable domain of b).

Preferred antigen binding proteins of the first aspect include those comprising a light chain variable domain having at least 90%, at least 95%, or is identical to the amino acid sequence set forth in SEQ ID NO:63 and a heavy chain variable domain having at least 90%, at least 95%, or is identical to the amino acid sequence set forth in SEQ ID NO:17; those comprising a light chain variable domain having at least 90%, at least 95%, or is identical to the amino acid sequence set forth in SEQ ID NO:64 and a heavy chain variable domain having at least 90%, at least 95%, or is identical to the amino acid sequence set forth in SEQ ID NO:18; those comprising a light chain variable domain having at least 90%, at least 95%, or is identical to the amino acid sequence set forth in SEQ ID NO:65 and a heavy chain variable domain having at least 90%, at least 95%, or is identical to the amino acid sequence set forth in SEQ ID NO:19; those comprising a light chain variable domain having at least 90%, at least 95%, or is identical to the amino acid sequence set forth in SEQ ID NO:66 and a heavy chain variable domain having at least 90%, at least 95%, or is identical to the amino acid sequence set forth in SEQ ID NO:20; those comprising a light chain variable domain having at least 90%, at least 95%, or is identical to the amino acid sequence set forth in SEQ ID NO:67 and a heavy chain variable domain having at least 90%, at least 95%, or is identical to the amino acid sequence set forth in SEQ ID NO:21; those comprising a light chain variable domain having at least 90%, at least 95%, or is identical to the amino acid sequence set forth in SEQ ID NO:68 and a heavy chain variable domain having at least 90%, at least 95%, or is identical to the amino acid sequence set forth in SEQ ID NO:22; those comprising a light chain variable domain having at least 90%, at least 95%, or is identical to the amino acid sequence set forth in SEQ ID NO:69 and a heavy chain variable domain having at least 90%, at least 95%, or is identical to the amino acid sequence set forth in SEQ ID NO:23; and those comprising a light chain variable domain having at least 90%, at least 95%, or is identical to the amino acid sequence set forth in SEQ ID NO:70 and a heavy chain variable domain having at least 90%, at least 95%, or is identical to the amino acid sequence set forth in SEQ ID NO:24.

In a second aspect, the CD27L antigen binding protein comprises a) a light chain variable domain having no more than ten or no more than five amino acid additions, deletions or substitutions from the amino acid sequence set forth in SEQ ID NO:63, SEQ ID NO:64, SEQ ID NO:65, SEQ ID NO:66, SEQ ID NO:67, SEQ ID NO:68, SEQ ID NO:69, or SEQ ID NO:70; b) a heavy chain variable domain having no more than ten or no more than five amino acid additions, deletions or substitutions from the amino acid sequence set forth in SEQ ID NO:17, SEQ ID NO:18, SEQ ID NO:19, SEQ ID NO:20, SEQ ID NO:21, SEQ ID NO:22, SEQ ID NO:23, or SEQ ID NO:24; or c) the light chain variable domain of a) and the heavy chain variable domain of b).

Preferred antigen binding proteins of the second aspect include those comprising a light chain variable domain having no more than ten or no more than five amino acid additions, deletions or substitutions from the amino acid sequence set forth in SEQ ID NO:63 and a heavy chain variable domain having no more than ten or no more than five amino acid additions, deletions or substitutions from the amino acid sequence set forth in SEQ ID NO:17; those comprising a light chain variable domain having no more than ten or no more than five amino acid additions, deletions or substitutions from the amino acid sequence set forth in SEQ ID NO:64 and a heavy chain variable domain having no more than ten or no more than five amino acid additions, deletions or substitutions from the amino acid sequence set forth in SEQ ID NO:18; those comprising a light chain variable domain having no more than ten or no more than five amino acid additions, deletions or substitutions from the amino acid sequence set forth in SEQ ID NO:65 and a heavy chain variable domain having no more than ten or no more than five amino acid additions, deletions or substitutions from the amino acid sequence set forth in SEQ ID NO:19; those comprising a light chain variable domain having no more than ten or no more than five amino acid additions, deletions or substitutions from the amino acid sequence set forth in SEQ ID NO:66 and a heavy chain variable domain having no more than ten or no more than five amino acid additions, deletions or substitutions from the amino acid sequence set forth in SEQ ID NO:20; those comprising a light chain variable domain having no more than ten or no more than five amino acid additions, deletions or substitutions from the amino acid sequence set forth in SEQ ID NO:67 and a heavy chain variable domain having no more than ten or no more than five amino acid additions, deletions or substitutions from the amino acid sequence set forth in SEQ ID NO:21; those comprising a light chain variable domain having no more than ten or no more than five amino acid additions, deletions or substitutions from the amino acid sequence set forth in SEQ ID NO:68 and a heavy chain variable domain having no more than ten or no more than five amino acid additions, deletions or substitutions from the amino acid sequence set forth in SEQ ID NO:22; those comprising a light chain variable domain having no more than ten or no more than five amino acid additions, deletions or substitutions from the amino acid sequence set forth in SEQ ID NO:69 and a heavy chain variable domain having no more than ten or no more than five amino acid additions, deletions or substitutions from the amino acid sequence set forth in SEQ ID NO:23; and those comprising a light chain variable domain having no more than ten or no more than five amino acid additions, deletions or substitutions from the amino acid sequence set forth in SEQ ID NO:70 and a heavy chain variable domain having no more than ten or no more than five amino acid additions, deletions or substitutions from the amino acid sequence set forth in SEQ ID NO:24.

In a third aspect, the CD27L antigen binding protein contains a light chain variable domain comprising a) an LCDR1 having no more than three amino acid additions, deletions, or substitutions from the LCDR1 sequence set forth in SEQ ID NO:71; an LCDR2 having no more than three amino acid additions, deletions, or substitutions from the LCDR2 sequence set forth in SEQ ID NO:79; and an LCDR3 having no more than three amino acid additions, deletions, or substitutions from the LCDR3 sequence set forth in SEQ ID NO:87; b) an LCDR1 having no more than three amino acid additions, deletions, or substitutions from the LCDR1 sequence set forth in SEQ ID NO:72; an LCDR2 having no more than three amino acid additions, deletions, or substitutions from the LCDR2 sequence set forth in SEQ ID NO:80; and an LCDR3 having no more than three amino acid additions, deletions, or substitutions from the LCDR3 sequence set forth in SEQ ID NO:88; c) an LCDR1 having no more than three amino acid additions, deletions, or substitutions from the LCDR1 sequence set forth in SEQ ID NO:73; an LCDR2 having no more than three amino acid additions, deletions, or substitutions from the LCDR2 sequence set forth in SEQ ID NO:81; and an LCDR3 having no more than three amino acid additions, deletions, or substitutions from the LCDR3 sequence set forth in SEQ ID NO:89; d) an LCDR1 having no more than three amino acid additions, deletions, or substitutions from the LCDR1 sequence set forth in SEQ ID NO:74; an LCDR2 having no more than three amino acid additions, deletions, or substitutions from the LCDR2 sequence set forth in SEQ ID NO:82; and an LCDR3 having no more than three amino acid additions, deletions, or substitutions from the LCDR3 sequence set forth in SEQ ID NO:90; e) an LCDR1 having no more than three amino acid additions, deletions, or substitutions from the LCDR1 sequence set forth in SEQ ID NO:75; an LCDR2 having no more than three amino acid additions, deletions, or substitutions from the LCDR2 sequence set forth in SEQ ID NO:83; and an LCDR3 having no more than three amino acid additions, deletions, or substitutions from the LCDR3 sequence set forth in SEQ ID NO:91; f) an LCDR1 having no more than three amino acid additions, deletions, or substitutions from the LCDR1 sequence set forth in SEQ ID NO:76; an LCDR2 having no more than three amino acid additions, deletions, or substitutions from the LCDR2 sequence set forth in SEQ ID NO:84; and an LCDR3 having no more than three amino acid additions, deletions, or substitutions from the LCDR3 sequence set forth in SEQ ID NO:92; g) an LCDR1 having no more than three amino acid additions, deletions, or substitutions from the LCDR1 sequence set forth in SEQ ID NO:77; an LCDR2 having no more than three amino acid additions, deletions, or substitutions from the LCDR2 sequence set forth in SEQ ID NO:85; and an LCDR3 having no more than three amino acid additions, deletions, or substitutions from the LCDR3 sequence set forth in SEQ ID NO:93; or h) an LCDR1 having no more than three amino acid additions, deletions, or substitutions from the LCDR1 sequence set forth in SEQ ID NO:78; an LCDR2 having no more than three amino acid additions, deletions, or substitutions from the LCDR2 sequence set forth in SEQ ID NO:86; and an LCDR3 having no more than three amino acid additions, deletions, or substitutions from the LCDR3 sequence set forth in SEQ ID NO:94; and a heavy chain variable domain comprising i) an HCDR1 having no more than three amino acid additions, deletions, or substitutions from the HCDR1 sequence set forth in SEQ ID NO:25; an HCDR2 having no more than three amino acid additions, deletions, or substitutions from the HCDR2 sequence set forth in SEQ ID NO:33; and an HCDR3 having no more than three amino acid additions, deletions, or substitutions from the HCDR3 sequence set forth in SEQ ID NO:41; j) an HCDR1 having no more than three amino acid additions, deletions, or substitutions from the HCDR1 sequence set forth in SEQ ID NO:26; an HCDR2 having no more than three amino acid additions, deletions, or substitutions from the HCDR2 sequence set forth in SEQ ID NO:34; and an HCDR3 having no more than three amino acid additions, deletions, or substitutions from the HCDR3 sequence set forth in SEQ ID NO:42; k) an HCDR1 having no more than three amino acid additions, deletions, or substitutions from the HCDR1 sequence set forth in SEQ ID NO:27; an HCDR2 having no more than three amino acid additions, deletions, or substitutions from the HCDR2 sequence set forth in SEQ ID NO:35; and an HCDR3 having no more than three amino acid additions, deletions, or substitutions from the HCDR3 sequence set forth in SEQ ID NO:43; l) an HCDR1 having no more than three amino acid additions, deletions, or substitutions from the HCDR1 sequence set forth in SEQ ID NO:28; an HCDR2 having no more than three amino acid additions, deletions, or substitutions from the HCDR2 sequence set forth in SEQ ID NO:36; and an HCDR3 having no more than three amino acid additions, deletions, or substitutions from the HCDR3 sequence set forth in SEQ ID NO:44; m) an HCDR1 having no more than three amino acid additions, deletions, or substitutions from the HCDR1 sequence set forth in SEQ ID NO:29; an HCDR2 having no more than three amino acid additions, deletions, or substitutions from the HCDR2 sequence set forth in SEQ ID NO:37; and an HCDR3 having no more than three amino acid additions, deletions, or substitutions from the HCDR3 sequence set forth in SEQ ID NO:45; n) an HCDR1 having no more than three amino acid additions, deletions, or substitutions from the HCDR1 sequence set forth in SEQ ID NO:30; an HCDR2 having Gno more than three amino acid additions, deletions, or substitutions from the HCDR2 sequence set forth in SEQ ID NO:38; and an HCDR3 having no more than three amino acid additions, deletions, or substitutions from the HCDR3 sequence set forth in SEQ ID NO:46; o) an HCDR1 having no more than three amino acid additions, deletions, or substitutions from the HCDR1 sequence set forth in SEQ ID NO:31; an HCDR2 having no more than three amino acid additions, deletions, or substitutions from the HCDR2 sequence set forth in SEQ ID NO:39; and an HCDR3 having no more than three amino acid additions, deletions, or substitutions from the HCDR3 sequence set forth in SEQ ID NO:47; or p) an HCDR1 having no more than three amino acid additions, deletions, or substitutions from the HCDR1 sequence set forth in SEQ ID NO:32; an HCDR2 having no more than three amino acid additions, deletions, or substitutions from the HCDR2 sequence set forth in SEQ ID NO:40; and an HCDR3 having no more than three amino acid additions, deletions, or substitutions from the HCDR3 sequence set forth in SEQ ID NO:48.

Preferred CD27L antigen binding proteins of third aspect include those comprising the light chain variable domain of a) and the heavy chain variable domain of i); those comprising the light chain variable domain of b) and the heavy chain variable domain of j); those comprising the light chain variable domain of c) and the heavy chain variable domain of k); those comprising the light chain variable domain of d) and the heavy chain variable domain of l); those comprising the light chain variable domain of e) and the heavy chain variable domain of m); those comprising the light chain variable domain of f) and the heavy chain variable domain of n); those comprising the light chain variable domain of g) and the heavy chain variable domain of o); and those comprising the light chain variable domain of h) and the heavy chain variable domain of p).

In a fourth aspect of the invention, the CD27L antigen binding protein of the first, second, or third aspect binds to human CD27L with an affinity of less than or equal to $2 \times 10^{-11}$ M.

In a fifth aspect of the invention, the CD27L antigen binding protein of the first, second, third, or fourth aspect inhibits binding of CD27L to CD27.

In a sixth aspect of the invention, the CD27L antigen binding protein of the first, second, third, fourth, or fifth aspect is an antibody, such as a human antibody. Preferred antibodies include those antibodies that comprise a light chain having the amino acid sequence set forth in SEQ ID:56 and a heavy chain having the amino acid sequence set forth in SEQ ID NO:10; those that comprise a light chain having the amino acid sequence set forth in SEQ ID:57 and a heavy chain having the amino acid sequence set forth in SEQ ID NO:11; those that comprise a light chain having the amino acid sequence set forth in SEQ ID:58 and a heavy chain having the amino acid sequence set forth in SEQ ID NO:12; those that comprise a light chain having the amino acid sequence set forth in SEQ ID:59 and a heavy chain having the amino acid sequence set forth in SEQ ID NO:13; those that comprise a light chain having the amino acid sequence set forth in SEQ ID:60 and a heavy chain having the amino acid sequence set forth in SEQ ID NO:14; those that comprise a light chain having the amino acid sequence set forth in SEQ ID:61 and a heavy chain having the amino acid sequence set forth in SEQ ID NO:15; and those that comprise a light chain having the amino acid sequence set forth in SEQ ID:62 and a heavy chain having the amino acid sequence set forth in SEQ ID NO:16.

In a seventh aspect, a CD27L antigen binding protein of the first, second, third, fourth, fifth, or sixth aspect is conjugated to a drug or chemotherapeutic agent. In preferred embodiments, the drug or chemotherapeutic agent is conjugated to the antigen binding protein, e.g. antibody, using a linker. Preferred linkers include non-cleavable linkers such as MCC. A preferred chemotherapeutic agent is DM1. Thus, in particularly preferred embodiments, the seventh aspect provides a CD27L antigen binding protein of the first, second, third, fourth, fifth, or sixth aspect conjugated to DM1 by a MCC linker attached to one or more lysine residues.

The process of conjugating DM1 to a CD27L antigen binding protein, e.g. antibody, will produce a composition comprising a population of DM1-conjugated antibodies having a range of DM1 molecules per antibody. It is possible to measure an average number for the composition. In preferred embodiments, the average number of DM1 molecules per CD27L antigen binding protein, e.g. antibody, is between 1 and 10, between 3 and 7, or between 4 and 6. In preferred embodiments, the composition of CD27L antigen binding proteins of the first, second, third, fourth, fifth, sixth, or seventh aspect of this invention has an average number of DM1 molecules per CD27L antigen binding protein of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. Such a composition may contain a therapeutically effective amount of the CD27L antigen binding protein and may be lyophilized.

In an eight aspect, the invention provides isolated nucleic acids encoding one or more polypeptide components of a CD27L antigen binding protein, e.g., an antibody light chain or antibody heavy chain. In preferred embodiments the nucleic acid encodes a polypeptide comprising:

a) a light chain variable domain having at least 95% identity to the amino acid sequence set forth in SEQ ID NO:63, SEQ ID NO:64, SEQ ID NO:65, SEQ ID NO:66, SEQ ID NO:67, SEQ ID NO:68, SEQ ID NO:69, or SEQ ID NO:70;

b) a heavy chain variable domain having at least 95% identity to the amino acid sequence set forth in SEQ ID NO:17, SEQ ID NO:18, SEQ ID NO:19, SEQ ID NO:20, SEQ ID NO:21, SEQ ID NO:22, SEQ ID NO:23, or SEQ ID NO:24;

c) a light chain variable domain having no more than five amino acid additions, deletions or substitutions from the amino acid sequence set forth in SEQ ID NO:63, SEQ ID NO:64, SEQ ID NO:65, SEQ ID NO:66, SEQ ID NO:67, SEQ ID NO:68, SEQ ID NO:69, or SEQ ID NO:70;

d) a heavy chain variable domain having no more than five amino acid additions, deletions or substitutions from the amino acid sequence set forth in SEQ ID NO:17, SEQ ID NO:18, SEQ ID NO:19, SEQ ID NO:20, SEQ ID NO:21, SEQ ID NO:22, SEQ ID NO:23, or SEQ ID NO:24;

e) a light chain variable domain comprising:

i) an LCDR1 having no more than three amino acid additions, deletions, or substitutions from the LCDR1 sequence set forth in SEQ ID NO:71; an LCDR2 having no more than three amino acid additions, deletions, or substitutions from the LCDR2 sequence set forth in SEQ ID NO:79; and an LCDR3 having no more than three amino acid additions, deletions, or substitutions from the LCDR3 sequence set forth in SEQ ID NO:87;

ii) an LCDR1 having no more than three amino acid additions, deletions, or substitutions from the LCDR1 sequence set forth in SEQ ID NO:72; an LCDR2 having no more than three amino acid additions, deletions, or substitutions from the LCDR2 sequence set forth in SEQ ID NO:80; and an LCDR3 having no more than three amino acid additions, deletions, or substitutions from the LCDR3 sequence set forth in SEQ ID NO:88;

iii) an LCDR1 having no more than three amino acid additions, deletions, or substitutions from the LCDR1 sequence set forth in SEQ ID NO:73; an LCDR2 having no more than three amino acid additions, deletions, or substitutions from the LCDR2 sequence set forth in SEQ ID NO:81; and an LCDR3 having no more than three amino acid additions, deletions, or substitutions from the LCDR3 sequence set forth in SEQ ID NO:89;

iv) an LCDR1 having no more than three amino acid additions, deletions, or substitutions from the LCDR1 sequence set forth in SEQ ID NO:74; an LCDR2 having no more than three amino acid additions, deletions, or substitutions from the LCDR2 sequence set forth in SEQ ID NO:82; and an LCDR3 having no more than three amino acid additions, deletions, or substitutions from the LCDR3 sequence set forth in SEQ ID NO:90;

v) an LCDR1 having no more than three amino acid additions, deletions, or substitutions from the LCDR1 sequence set forth in SEQ ID NO:75; an LCDR2 having no more than three amino acid additions, deletions, or substitutions from the LCDR2 sequence set forth in SEQ ID NO:83; and an LCDR3 having no more than three amino acid additions, deletions, or substitutions from the LCDR3 sequence set forth in SEQ ID NO:91;

vi) an LCDR1 having no more than three amino acid additions, deletions, or substitutions from the LCDR1 sequence set forth in SEQ ID NO:76; an LCDR2 having no more than three amino acid additions, deletions, or substitutions from the LCDR2 sequence set forth in SEQ ID NO:84; and an LCDR3 having no more than three amino acid additions, deletions, or substitutions from the LCDR3 sequence set forth in SEQ ID NO:92;

vii) an LCDR1 having no more than three amino acid additions, deletions, or substitutions from the LCDR1 sequence set forth in SEQ ID NO:77; an LCDR2 having no more than three amino acid additions, deletions, or substitutions from the LCDR2 sequence set forth in SEQ ID NO:85; and an LCDR3 having no more than three amino acid additions, deletions, or substitutions from the LCDR3 sequence set forth in SEQ ID NO:93; or viii) an LCDR1 having no more than three amino acid additions, deletions, or substitutions from the LCDR1 sequence set forth in SEQ ID NO:78; an LCDR2 having no more than three amino acid additions, deletions, or substitutions from the LCDR2 sequence set forth in SEQ ID NO:86; and an LCDR3 having no more than three amino acid additions, deletions, or substitutions from the LCDR3 sequence set forth in SEQ ID NO:94; or f) a heavy chain variable domain comprising:

i) an HCDR1 having no more than three amino acid additions, deletions, or substitutions from the HCDR1 sequence set forth in SEQ ID NO:25; an HCDR2 having no more than three amino acid additions, deletions, or substitutions from the HCDR2 sequence set forth in SEQ ID NO:33; and an HCDR3 having no more than three amino acid additions, deletions, or substitutions from the HCDR3 sequence set forth in SEQ ID NO:41;

ii) an HCDR1 having no more than three amino acid additions, deletions, or substitutions from the HCDR1 sequence set forth in SEQ ID NO:26; an HCDR2 having no more than three amino acid additions, deletions, or substitutions from the HCDR2 sequence set forth in SEQ ID NO:34; and an HCDR3 having no more than three amino acid additions, deletions, or substitutions from the HCDR3 sequence set forth in SEQ ID NO:42;

iii) an HCDR1 having no more than three amino acid additions, deletions, or substitutions from the HCDR1 sequence set forth in SEQ ID NO:27; an HCDR2 having no more than three amino acid additions, deletions, or substitutions from the HCDR2 sequence set forth in SEQ ID NO:35; and an HCDR3 having no more than three amino acid additions, deletions, or substitutions from the HCDR3 sequence set forth in SEQ ID NO:43;

iv) an HCDR1 having no more than three amino acid additions, deletions, or substitutions from the HCDR1 sequence set forth in SEQ ID NO:28; an HCDR2 having no more than three amino acid additions, deletions, or substitutions from the HCDR2 sequence set forth in SEQ ID NO:36; and an HCDR3 having no more than three amino acid additions, deletions, or substitutions from the HCDR3 sequence set forth in SEQ ID NO:44;

v) an HCDR1 having no more than three amino acid additions, deletions, or substitutions from the HCDR1 sequence set forth in SEQ ID NO:29; an HCDR2 having no more than three amino acid additions, deletions, or substitutions from the HCDR2 sequence set forth in SEQ ID NO:37; and an HCDR3 having no more than three amino acid additions, deletions, or substitutions from the HCDR3 sequence set forth in SEQ ID NO:45;

vi) an HCDR1 having no more than three amino acid additions, deletions, or substitutions from the HCDR1 sequence set forth in SEQ ID NO:30; an HCDR2 having no more than three amino acid additions, deletions, or substitutions from the HCDR2 sequence set forth in SEQ ID NO:38; and an HCDR3 having no more than three amino acid additions, deletions, or substitutions from the HCDR3 sequence set forth in SEQ ID NO:46;

vii) an HCDR1 having no more than three amino acid additions, deletions, or substitutions from the HCDR1 sequence set forth in SEQ ID NO:31; an HCDR2 having no more than three amino acid additions, deletions, or substitutions from the HCDR2 sequence set forth in SEQ ID NO:39; and an HCDR3 having no more than three amino acid additions, deletions, or substitutions from the HCDR3 sequence set forth in SEQ ID NO:47; or viii) an HCDR1 having no more than three amino acid additions, deletions, or substitutions from the HCDR1 sequence set forth in SEQ ID NO:32; an HCDR2 having no more than three amino acid additions, deletions, or substitutions from the HCDR2 sequence set forth in SEQ ID NO:40; and an HCDR3 having no more than three amino acid additions, deletions, or substitutions from the HCDR3 sequence set forth in SEQ ID NO:48.

In certain embodiments of the eighth aspect, the polypeptide encodes an antibody light chain and is at least 80%, at least 90%, at least 95%, or is 100% identical to the nucleotide sequence set forth in SEQ ID NO:49, SEQ ID NO:50, SEQ ID NO:51, SEQ ID NO:52, SEQ ID NO:53, SEQ ID NO:54, or SEQ ID NO:55. In other embodiments of the eighth aspect, the polypeptide encodes an antibody heavy chain and is at least 80%, at least 90%, at least 95%, or is 100% identical to the nucleotide sequence set forth in SEQ ID NO:3, SEQ ID NO:4, SEQ ID NO:5, SEQ ID NO:6, SEQ ID NO:7, SEQ ID NO:8, or SEQ ID NO:9.

In a ninth aspect, the invention provides an expression vector comprising one or more isolated nucleic acids of the eighth aspect. In certain embodiments, the expression vector encodes an antibody light chain, an antibody heavy chain, or both an antibody light chain and a heavy chain.

In a tenth aspect, the invention provides a recombinant host cell comprising one or more isolated nucleic acids of the eighth aspect operably linked to a promoter, including recombinant host cells comprising one or more expression vectors of the ninth aspect of the invention. In preferred embodiments, the recombinant host cell secretes an antibody that binds CD27L. Preferred host cells are mammalian host cells, including CHO cell lines.

In an eleventh aspect, the invention provides methods of making a CD27L antibody drug conjugate of the seventh aspect by conjugating a linker and drug, e.g., chemotherapeutic agent, to any of the CD27L antigen binding proteins of the first, second, third, fourth, fifth, or sixth aspects. The linker and drug may be connect first and then conjugated to the CD27L antigen binding protein or the linker may be first conjugated to the CD27L antigen binding protein then connected to the drug. In preferred embodiments, the linker is MCC and the drug is DM1. In particularly preferred embodiments, the CD27L antigen binding protein is an antibody comprising a light chain variable domain amino acid sequence as set forth in SEQ ID NO:63 and a heavy chain variable domain amino acid sequence as set forth in SEQ ID NO:17 (e.g., Ab1), an antibody comprising a light chain variable domain amino acid sequence as set forth in SEQ ID NO:64 and a heavy chain variable domain amino acid sequence as set forth in SEQ ID NO:18 (e.g., Ab2), an antibody comprising a light chain variable domain amino acid sequence as set forth in SEQ ID NO:65 and a heavy chain variable domain amino acid sequence as set forth in SEQ ID NO:19 (e.g., Ab3), an antibody comprising a light chain variable domain amino acid sequence as set forth in SEQ ID NO:66 and a heavy chain variable domain amino acid sequence as set forth in SEQ ID NO:20 (e.g., Ab4), an antibody comprising a light chain variable domain amino acid sequence as set forth in SEQ ID NO:67 and a heavy chain variable domain amino acid sequence as set forth in SEQ ID NO:21 (e.g., Ab5), an antibody comprising a light chain variable domain amino acid sequence as set forth in SEQ ID NO:68 and a heavy chain variable domain amino acid sequence as set forth in SEQ ID NO:22 (e.g., Ab6), an antibody comprising a light chain variable domain amino acid sequence as set forth in SEQ ID NO:69 and a heavy chain variable domain amino acid sequence as set forth in SEQ ID NO:23 (e.g., Ab7), or an antibody comprising a light chain variable domain amino acid sequence as set forth in SEQ ID NO:70 and a heavy chain variable domain amino acid sequence as set forth in SEQ ID NO:24 (e.g., Ab8) conjugated to DM1 by MCC by chemically reacting one or more lysine residues within the antibody with MCC or MCC-DM1.

In a twelfth aspect, the invention provides methods of treating cancer comprising administering to a patient a therapeutically effective amount of a composition comprising a therapeutically effective amount of a CD27L antigen binding protein of the first, second, third, fourth, fifth, or sixth aspect. In preferred embodiments, the CD27L antigen binding protein is an antibody comprising a light chain variable domain amino acid sequence as set forth in SEQ ID NO:63 and a heavy chain variable domain amino acid sequence as set forth in SEQ ID NO:17 (e.g., Ab1), an antibody comprising a light chain variable domain amino acid sequence as set forth in SEQ ID NO:64 and a heavy chain variable domain amino acid sequence as set forth in SEQ ID NO:18 (e.g., Ab2), an antibody comprising a light chain variable domain amino acid sequence as set forth in SEQ ID NO:65 and a heavy chain variable domain amino acid sequence as set forth in SEQ ID NO:19 (e.g., Ab3), an antibody comprising a light chain variable domain amino acid sequence as set forth in SEQ ID NO:66 and a heavy chain variable domain amino acid sequence as set forth in SEQ ID NO:20 (e.g., Ab4), an antibody comprising a light chain variable domain amino acid sequence as set forth in SEQ ID NO:67 and a heavy chain variable domain amino acid sequence as set forth in SEQ ID NO:21 (e.g., Ab5), an antibody comprising a light chain variable domain amino acid sequence as set forth in SEQ ID NO:68 and a heavy chain variable domain amino acid sequence as set forth in SEQ ID NO:22 (e.g., Ab6), an antibody comprising a light chain variable domain amino acid sequence as set forth in SEQ ID NO:69 and a heavy chain variable domain amino acid sequence as set forth in SEQ ID NO:23 (e.g., Ab7), or an antibody comprising a light chain variable domain amino acid sequence as set forth in SEQ ID NO:70 and a heavy chain variable domain amino acid sequence as set forth in SEQ ID NO:24 (e.g., Ab8). In particularly preferred embodiments, the CD27L antigen binding protein is conjugated to a chemotherapeutic agent (e.g., DM1) by a linker (MCC). In other preferred embodiments of the twelfth aspect, the antibody comprises enhanced effector function.

In some embodiments, the CD27L antigen binding protein is administered to a patient having renal cell carcinomas (RCC), clear cell RCC, head and neck cancer, glioblastoma, breast cancer, brain tumor, nasopharangeal carcinoma, non-Hodgkin's lymphoma (NHL), acute lymphocytic leukemia (ALL), chronic lymphocytic leukemia (CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphoma, T-cell leukemia/lymphomas (ATLL), adult T-cell leukemia (T-ALL), entroblastic/centrocytic (cb/cc) follicular lymphoma cancer, diffuse large cell lymphoma of B lineage, angioimmunoblastic lymphadenopathy (AILD)-like T cell lymphoma, HIV associated body cavity based lymphoma, embryonal carcinoma, undifferentiated carcinoma of the rhino-pharynx, Castleman's disease, Kaposi's Sarcoma, multiple myeloma, Waldenstrom's macroglobulinemia or other B-cell lymphoma.

In certain embodiments, a sample from a patient is tested for CD27L expression prior to administering the CD27L antigen binding protein. CD27L expression may be determined by testing for the presence of CD27L-encoding RNA or for the presence of CD27L protein in the sample. The sample may be a blood sample or biopsy.

In a thirteenth aspect, the invention provides methods of treating an autoimmune or inflammatory disorder said method comprising administering a therapeutically effective amount of a CD27L antigen binding protein of any one of the first, second, third, fourth, fifth, or sixth aspects to a patient in need thereof. In preferred embodiments, the CD27L antigen binding protein is an antibody comprising a light chain variable domain amino acid sequence as set forth in SEQ ID NO:63 and a heavy chain variable domain amino acid sequence as set forth in SEQ ID NO:17 (e.g., Ab1), an antibody comprising a light chain variable domain amino acid sequence as set forth in SEQ ID NO:64 and a heavy chain variable domain amino acid sequence as set forth in SEQ ID NO:18 (e.g., Ab2), an antibody comprising a light chain variable domain amino acid sequence as set forth in SEQ ID NO:65 and a heavy chain variable domain amino acid sequence as set forth in SEQ ID NO:19 (e.g., Ab3), an antibody comprising a light chain variable domain amino acid sequence as set forth in SEQ ID NO:66 and a heavy chain variable domain amino acid sequence as set forth in SEQ ID NO:20 (e.g., Ab4), an antibody comprising a light chain variable domain amino acid sequence as set forth in SEQ ID NO:67 and a heavy chain variable domain amino acid sequence as set forth in SEQ ID NO:21 (e.g., Ab5), an antibody comprising a light chain variable domain amino acid sequence as set forth in SEQ ID NO:68 and a heavy chain variable domain amino acid sequence as set forth in SEQ ID NO:22 (e.g., Ab6), an antibody comprising a light chain variable domain amino acid sequence as set forth in SEQ ID NO:69 and a heavy chain variable domain amino acid sequence as set forth in SEQ ID NO:23 (e.g., Ab7), or an antibody comprising a light chain variable domain amino acid sequence as set forth in SEQ ID NO:70 and a heavy chain variable domain amino acid sequence as set forth in SEQ ID NO:24 (e.g., Ab8). In preferred embodiments, the CD27L antigen binding protein inhibits binding of CD27 to CD27L. In particularly preferred embodiments, the autoimmune or inflammatory disorder is systemic lupus erythematosus (SLE), insulin dependent diabetes mellitus (IDDM), inflammatory bowel disease (IBD), multiple sclerosis (MS), psoriasis, autoimmune thyroiditis, rheumatoid arthritis (RA), or glomerulonephritis. In other embodiments, treatment inhibits or prevents transplant rejection or graft versus host disease in the patient.

BRIEF DESCRIPTION OF THE DRAWINGS

FIG. 1. Summary of functional and physical characteristics of exemplary embodiments of CD27L antigen binding proteins.

FIG. 11. Results of CD27L mRNA and Protein Expression Analysis. The results indicate that there is a high prevalence of CD27L expression in RCC, B-NHL and CLL cells.

DETAILED DESCRIPTION OF PREFERRED EMBODIMENTS

Figure 2:
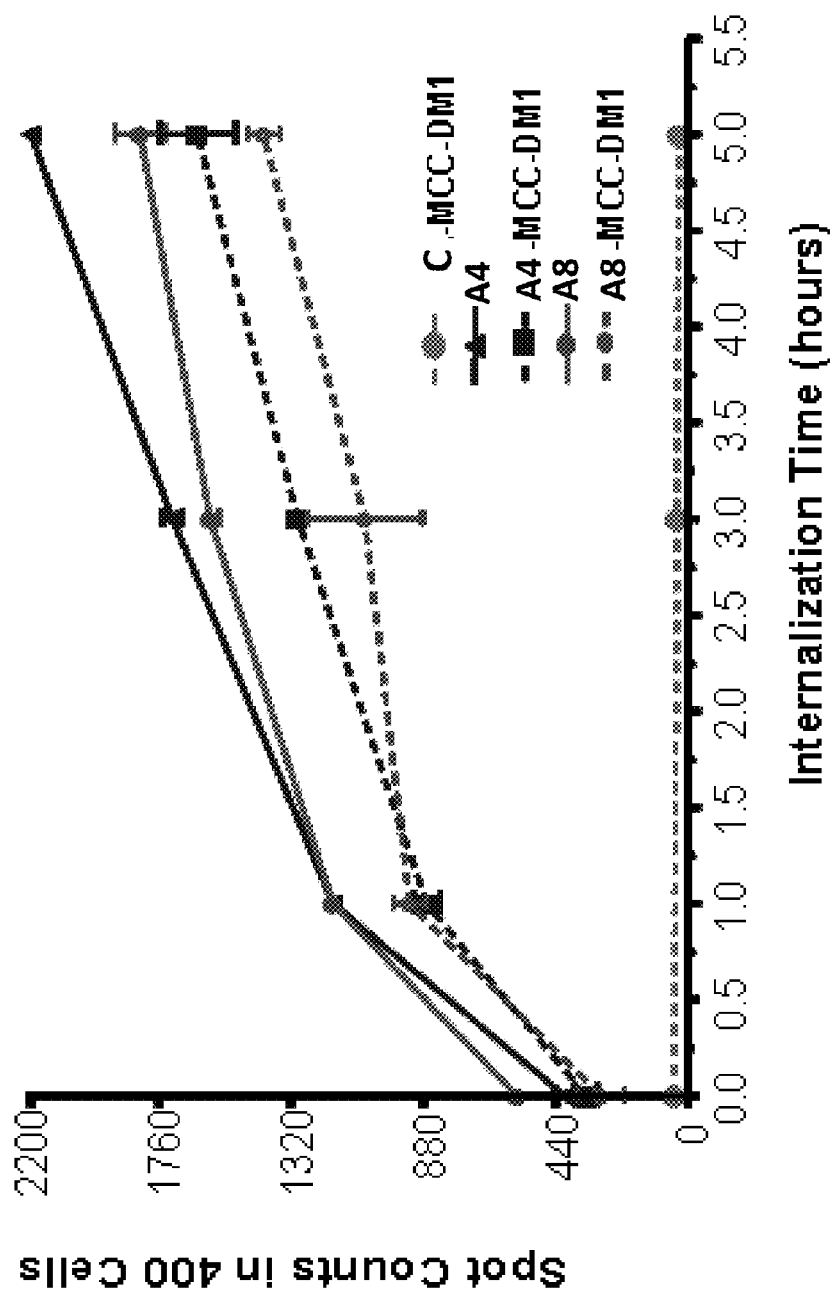
FIG. 2. Measurement of the level and the rate of internalization of Ab4 (A4) and Ab8 (A8) and their conjugated counterparts into 786-0 cells over time (A).

The section headings used herein are for organizational purposes only and are not to be construed as limiting the subject matter described. All references cited within the body of this specification are expressly incorporated by reference in their entirety.

Standard techniques may be used for recombinant DNA, oligonucleotide synthesis, tissue culture and transformation, protein purification, etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manuel*, $3^{rd}$ ed., Cold Spring Harbor Laboratory Press, cold Spring Harbor, N.Y., which is incorporated herein by reference for any purpose. Unless specific definitions are provided, the nomenclature used in connection with, and the laboratory procedures and techniques of, analytic chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

CD27L

The antigen binding proteins bind to CD27L, which is also known as CD70 and TNFSF7. CD27L was first described in U.S. Pat. No. 5,573,924. An exemplary human CD27L amino acid sequence is provided herein as SEQ ID NO:1, which corresponds to NCBI Reference Sequence NP_001423.1 (GI:4507605). In certain embodiments, the antigen binding protein blocks the interaction of CD27L with its receptor CD27. An exemplary CD27 amino acid sequence is provided as SEQ ID NO:2, which corresponds to Swiss-Prot: P26842.2 (GI:269849546). A mature CD27 amino acid sequence corresponds to amino acids 20-260 of SEQ ID NO:2.

CD27L Antigen Binding Proteins

The present invention provides antigen binding proteins that specifically bind CD27L. Embodiments of antigen binding proteins comprise peptides and/or polypeptides that specifically bind CD27L. Such peptides or polypeptides may optionally include one or more port-translational modification. Embodiments of antigen binding proteins comprise antibodies and fragments thereof, as variously defined herein, that specifically bind CD27L. These include antibodies that specifically bind human CD27L, including those that inhibit CD27L from binding and/or activating CD27.

The antigen binding proteins of the invention specifically bind to CD27L. "Specifically binds" as used herein means that the antigen binding protein preferentially binds CD27L over other proteins. In some embodiments "specifically binds" means the CD27L antigen binding protein has a higher affinity for CD27L than for other proteins. CD27L antigen binding proteins that specifically bind CD27L may have a binding affinity for human CD27L of less than or equal to $1 \times 10^{-7}$ M, less than or equal to $2 \times 10^{-7}$ M, less than or equal to $3 \times 10^{-7}$ M, less than or equal to $4 \times 10^{-7}$ M, less than or equal to $5 \times 10^{-7}$ M, less than or equal to $6 \times 10^{-7}$ M, less than or equal to $7 \times 10^{-7}$ M, less than or equal to $8 \times 10^{-7}$ M, less than or equal to $9 \times 10^{-7}$ M, less than or equal to $1 \times 10^{-8}$ M, less than or equal to $2 \times 10^{-8}$ M, less than or equal to $3 \times 10^{-8}$ M, less than or equal to $4 \times 10^{-8}$ M, less than or equal to $5 \times 10^{-8}$ M, less than or equal to $6 \times 10^{-8}$ M, less than or equal to $7 \times 10^{-8}$ M, less than or equal to $8 \times 10^{-8}$ M, less than or equal to $9 \times 10^{-8}$ M, less than or equal to $1 \times 10^{-9}$ M, less than or equal to $2 \times 10^{-9}$ M, less than or equal to $3 \times 10^{-9}$ M, less than or equal to $4 \times 10^{-9}$ M, less than or equal to $5 \times 10^{-9}$ M, less than or equal to $6 \times 10^{-9}$ M, less than or equal to $7 \times 10^{-9}$ M, less than or equal to $8 \times 10^{-9}$ M, less than or equal to $9 \times 10^{-9}$ M, less than or equal to $1 \times 10^{-10}$ M, less than or equal to $2 \times 10^{-10}$ M, less than or equal to $3 \times 10^{-10}$ M, less than or equal to $4 \times 10^{-10}$ M, less than or equal to $5 \times 10^{-10}$ M, less than or equal to $6 \times 10^{-10}$ M, less than or equal to $7 \times 10^{-10}$ M, less than or equal to $8 \times 10^{-10}$ M, less than or equal to $9 \times 10^{-10}$ M, less than or equal to $1 \times 10^{-11}$ M, less than or equal to $2 \times 10^{-11}$ M, less than or equal to $3 \times 10^{-11}$ M, less than or equal to $4 \times 10^{-11}$ M, less than or equal to $5 \times 10^{-11}$ M, less than or equal to $6 \times 10^{-11}$ M, less than or equal to $7 \times 10^{-11}$ M, less than or equal to $8 \times 10^{-11}$ M, less than or equal to $9 \times 10^{-11}$ M, less than or equal to $1 \times 10^{-12}$ M, less than or equal to $2 \times 10^{-12}$ M, less than or equal to $3 \times 10^{-12}$ M, less than or equal to $4 \times 10^{-12}$ M, less than or equal to $5 \times 10^{-12}$ M, less than or equal to $6 \times 10^{-12}$ M, less than or equal to $7 \times 10^{-12}$ M, less than or equal to $8 \times 10^{-12}$ M, or less than or equal to $9 \times 10^{-12}$ M. Methods of measuring the binding affinity of an antigen binding protein are well known in the art. Example 1 provides an exemplary method.

It is understood that when reference is made to the various embodiments of the CD27L-binding antibodies herein, that it also encompasses CD27L-binding fragments thereof. A CD27L-binding fragment comprises any of the antibody fragments or domains described herein that retains the ability to specifically bind to CD27L. The CD27L-binding fragment may be in any of the scaffolds described herein.

In certain therapeutic embodiments, a CD27L antigen binding protein inhibits binding of CD27L to CD27 and/or inhibits one or more biological activities associated with the binding of CD27L to CD27, e.g., CD27-mediated signaling. Such antigen binding proteins are said to be "neutralizing." In certain embodiments, the neutralizing CD27L antigen binding protein specifically binds CD27L and inhibits binding of CD27L to CD27 from anywhere between 10% to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more. For example, CD27L antigen binding proteins may be tested for neutralizing ability by determining the ability of the antigen binding protein to block binding of CD27-Fc to MP-1 cells (Slack et al, Int. Immunol. (1995) 7(7): 1087-1092)).

Embodiments of antigen binding proteins comprise a scaffold structure, as variously defined herein, with one or more complementarity determining regions (CDRs). Embodiments further include antigen binding proteins comprising a scaffold structure with one or more antibody variable domains, either heavy or light. Embodiments include antibodies that comprise a light chain variable domain selected from the group consisting of Ab1 Light Chain Variable Domain (LCv), Ab2 LCv, Ab3 LCv, Ab4 LCv, Ab5 LCv, Ab6 LCv, Ab7 LCv, and Ab8 LCv (SEQ ID NO:63-70, respectively) and/or a heavy chain variable domain selected from the group consisting of Ab1 Heavy Chain Variable Domain (HCv), Ab2 HCv, Ab3 HCv, Ab4 HCv, Ab5 HCv, Ab6 HCv, Ab7 HCv, and Ab8 HCv (SEQ ID NO:17-24, respectively), and fragments, derivatives, muteins, and variants thereof.

An exemplary light chain comprising Ab1 LCv is a light chain comprising the amino acid sequence set forth in SEQ ID NO:56.

An exemplary light chain comprising Ab2 LCv is a light chain comprising the amino acid sequence set forth in SEQ ID NO:57.

An exemplary light chain comprising Ab4 LCv is a light chain comprising the amino acid sequence set forth in SEQ ID NO:58.

An exemplary light chain comprising Ab5 LCv is a light chain comprising the amino acid sequence set forth in SEQ ID NO:59.

An exemplary light chain comprising Ab6 LCv is a light chain comprising the amino acid sequence set forth in SEQ ID NO:60.

An exemplary light chain comprising Ab7 LCv is a light chain comprising the amino acid sequence set forth in SEQ ID NO:61.

An exemplary light chain comprising Ab8 LCv is a light chain comprising the amino acid sequence set forth in SEQ ID NO:62.

An exemplary heavy chain comprising Ab1 HCv is a heavy chain comprising the amino acid sequence set forth in SEQ ID NO:10.

An exemplary heavy chain comprising Ab2 HCv is a heavy chain comprising the amino acid sequence set forth in SEQ ID NO:11.

An exemplary heavy chain comprising Ab4 HCv is a heavy chain comprising the amino acid sequence set forth in SEQ ID NO:12.

An exemplary heavy chain comprising Ab5 HCv is a heavy chain comprising the amino acid sequence set forth in SEQ ID NO:13.

An exemplary heavy chain comprising Ab6 HCv is a heavy chain comprising the amino acid sequence set forth in SEQ ID NO:14.

An exemplary heavy chain comprising Ab7 HCv is a heavy chain comprising the amino acid sequence set forth in SEQ ID NO:15.

An exemplary heavy chain comprising Ab8 HCv is a heavy chain comprising the amino acid sequence set forth in SEQ ID NO:16.

Additional examples of scaffolds that are envisioned include: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDZ domains, TEM-1 beta-lactamase, thioredoxin, staphylococcal nuclease, PHD-finger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ld1 receptor domains, gamma-crystallin, ubiquitin, transferrin, and or C-type lectin-like domains. Non-antibody scaffolds and their use as therapeutics are reviewed in Gebauer and Skerra, *Curr. Opin. Chem. Biol.*, 13:245-255 (2009) and Binz et al., Nat. Biotech., 23(10): 1257-1268 (2005), which are incorporated herein by reference in its entirety.

Aspects of the invention include antibodies comprising the following variable domains: Ab1 LCv/Ab1 HCv (SEQ ID NO:63/SEQ ID NO:17), Ab2 LCv/Ab2 HCv (SEQ ID NO:64/SEQ ID NO:18), Ab3 LCv/Ab3 HCv (SEQ ID NO:65/SEQ ID NO:19), Ab4 LCv/Ab4 HCv (SEQ ID NO:66/SEQ ID NO:20), Ab5 LCv/Ab5 HCv (SEQ ID NO:67/SEQ ID NO:21), Ab6 LCv/Ab6 HCv (SEQ ID NO:68/SEQ ID NO:22), Ab7 LCv/Ab7 HCv (SEQ ID NO:69/SEQ ID NO:23), Ab8 LCv/Ab8 HCv (SEQ ID NO:70/SEQ ID NO:24), and combinations thereof, as well as fragments, derivatives, muteins and variants thereof.

Exemplary antibodies of the invention include Ab1 (SEQ ID NO:56/SEQ ID NO:10), Ab2 (SEQ ID NO:57/SEQ ID NO:11), Ab4 (SEQ ID NO:58/SEQ ID NO:12), Ab5 (SEQ ID NO:59/SEQ ID NO:13), Ab6 (SEQ ID NO:60/SEQ ID NO:14), Ab7 (SEQ ID NO:61/SEQ ID NO:15), Ab8 (SEQ ID NO:62/SEQ ID NO:16).

Typically, each variable domain of an antibody light or heavy chain comprises three CDRs. The heavy chain variable domain comprises a heavy chain CDR1 (HCDR1), a heavy chain CDR2 (HCDR2), and a heavy chain CDR3 (HCDR3). The light chain variable domain comprises a light chain CDR1 (LCDR1), a light chain CDR2 (LCDR2), and a light chain CDR3 (LCDR3). In certain embodiments, an antigen binding protein comprises one or more CDRs contained within the preferred variable domains described herein.

Examples of such CDRs include, but are not limited to:

the CDRs of Ab1 LCv: LCDR1 (SEQ ID NO:71), LCDR2 (SEQ ID NO:79), and LCDR3 (SEQ ID NO:87);

the CDRs of Ab2 LCv: LCDR1 (SEQ ID NO:72), LCDR2 (SEQ ID NO:80), and LCDR3 (SEQ ID NO:88);

the CDRs of Ab3 LCv: LCDR1 (SEQ ID NO:73), LCDR2 (SEQ ID NO:81), and LCDR3 (SEQ ID NO:89);

the CDRs of Ab4 LCv: LCDR1 (SEQ ID NO:74), LCDR2 (SEQ ID NO:82), and LCDR3 (SEQ ID NO:90);

the CDRs of Ab5 LCv: LCDR1 (SEQ ID NO:75), LCDR2 (SEQ ID NO:83), and LCDR3 (SEQ ID NO:91);

the CDRs of Ab6 LCv: LCDR1 (SEQ ID NO:76), LCDR2 (SEQ ID NO:84), and LCDR3 (SEQ ID NO:92);

the CDRs of Ab7 LCv: LCDR1 (SEQ ID NO:77), LCDR2 (SEQ ID NO:85), and LCDR3 (SEQ ID NO:93);

the CDRs of Ab8 LCv: LCDR1 (SEQ ID NO:78), LCDR2 (SEQ ID NO:86), and LCDR3 (SEQ ID NO:94);

the CDRs of Ab1 HCv: HCDR1 (SEQ ID NO:25), HCDR2 (SEQ ID NO:33), and HCDR3 (SEQ ID NO:41);

the CDRs of Ab2 HCv: HCDR1 (SEQ ID NO:26), HCDR2 (SEQ ID NO:34), and HCDR3 (SEQ ID NO:42);

the CDRs of Ab3 HCv: HCDR1 (SEQ ID NO:27), HCDR2 (SEQ ID NO:35), and HCDR3 (SEQ ID NO:43);

the CDRs of Ab4 HCv: HCDR1 (SEQ ID NO:28), HCDR2 (SEQ ID NO:36), and HCDR3 (SEQ ID NO:44);

the CDRs of Ab5 HCv: HCDR1 (SEQ ID NO:29), HCDR2 (SEQ ID NO:37), and HCDR3 (SEQ ID NO:45);

the CDRs of Ab6 HCv: HCDR1 (SEQ ID NO:30), HCDR2 (SEQ ID NO:38), and HCDR3 (SEQ ID NO:46);

the CDRs of Ab7 HCv: HCDR1 (SEQ ID NO:31), HCDR2 (SEQ ID NO:39), and HCDR3 (SEQ ID NO:47); and the CDRs of Ab8 HCv: HCDR1 (SEQ ID NO:32), HCDR2 (SEQ ID NO:40), and HCDR3 (SEQ ID NO:48).

In some embodiments, the antigen binding protein comprises: A) a polypeptide, e.g., a light chain, that comprises an LCDR1 having an amino acid sequence selected from the group consisting of SEQ ID NOS:71, 72, 73, 74, 75, 76, 77, and 78; an LCDR2 having an amino acid sequence selected from the group consisting of SEQ ID NOS: 79, 80, 81, 82, 83, 84, 85, and 86; and/or an LCDR3 having an amino acid sequence selected from the group consisting of SEQ ID NOS: 87, 88, 89, 90, 91, 92, 93, and 94; and/or B) a polypeptide, e.g., a heavy chain, that comprises an HCDR1 having an amino acid sequence selected from the group consisting of SEQ ID NOS:25, 26, 27, 28, 29, 30, 31, and 32; an HCDR2 having an amino acid sequence selected from the group consisting of SEQ ID NOS:33, 34, 35, 36, 37, 38, 39, and 40; and/or an HCDR3 having an amino acid sequence selected from the group consisting of SEQ ID NOS:41, 42, 43, 44, 45, 46, 47, and 48.

In further embodiments, the antigen binding protein comprise A) a light chain amino acid sequence that comprises a LCDR1, LCDR2, and LCDR3 of any of Ab1 LCv, Ab2 LCv, Ab3 LCv, Ab4 LCv, Ab5 LCv, Ab6 LCv, Ab7 LCv, and Ab8 LCv, and B) a heavy chain amino acid sequence that comprises a HCDR1, HCDR2, and HCDR3 of any of Ab1 HCv, Ab2 HCv, Ab3 HCv, Ab4 HCv, Ab5 HCv, Ab6 HCv, Ab7 HCv, and Ab8 HCv.

In certain embodiments, the CDRs include no more than one, no more than two, no more than three, no more than four, no more than five, or no more than six amino acid additions, deletions, or substitutions from an exemplary CDR set forth herein.

Aspects of the invention include antibodies comprising a light chain variable domain selected from the group consisting of SEQ ID NOS:63, 64, 65, 66, 67, 68, 69, and 70. Aspects of the invention include antibodies comprising a heavy chain variable domain selected from the group consisting of SEQ ID NOS:17, 18, 19, 20, 21, 22, 23, and 24. Further aspects of the invention include antibodies comprising A) a light chain variable domain selected from the group consisting of SEQ ID NOS:63, 64, 65, 66, 67, 68, 69, and 70, and B) a heavy chain variable domain selected from the group consisting of SEQ ID NOS:17, 18, 19, 20, 21, 22, 23, and 24.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant region, e.g., a human alpha-, delta-, epsilon-, gamma-, or mu-type heavy chain constant region. In one embodiment the light or heavy chain constant region is a fragment, derivative, variant, or mutein of a naturally occurring constant region.

Aspects of the invention include antibodies comprising a light chain variable region selected from the group consisting of SEQ ID NOS:63, 64, 65, 66, 67, 68, 69, and 70 having no more than one, no more than two, no more than three, no more than four, no more than five, no more than six, no more than seven, no more than eight, no more than nine, or no more than ten amino acid additions, deletions, or substitutions. Aspects of the invention include antibodies comprising a heavy chain variable region selected from the group consisting of SEQ ID NOS:17, 18, 19, 20, 21, 22, 23, and 24 having no more than one, no more than two, no more than three, no more than four, no more than five, no more than six, no more than seven, no more than eight, no more than nine, or no more than ten amino acid additions, deletions, or substitutions. Further aspects of the invention include antibodies comprising A) comprising a light chain variable region selected from the group consisting of SEQ ID NOS:63, 64, 65, 66, 67, 68, 69, and 70 having no more than one, no more than two, no more than three, no more than four, no more than five, no more than six, no more than seven, no more than eight, no more than nine, or no more than ten amino acid additions, deletions, or substitutions, and B) a heavy chain variable region selected from the group consisting of SEQ ID NOS:17, 18, 19, 20, 21, 22, 23, and 24 having no more than one, no more than two, no more than three, no more than four, no more than five, no more than six, no more than seven, no more than eight, no more than nine, or no more than ten amino acid additions, deletions, or substitutions. For example, in certain exemplary embodiments, an antibody comprises 1) a variant of the light chain variable domain set forth in SEQ ID NO:66, wherein the phenylalanine at position 51 is mutated to a leucine and/or the proline at position 105 is mutated to a glycine or a glutamine; 2) a variant of the heavy chain variable domain set forth in SEQ ID NO:20, wherein the glutamine at position 1 is mutated to glutamic acid and/or the arginine at position 16 is mutated to a glycine; or a variant of the light chain variable domain set forth in SEQ ID NO:66, wherein the phenylalanine at position 51 is mutated to a leucine and/or the proline at position 105 is mutated to a glycine or a glutamine and a variant of the heavy chain variable domain set forth in SEQ ID NO:20, wherein the glutamine at position 1 is mutated to glutamic acid and/or the arginine at position 16 is mutated to a glycine.

In one variation, the antigen binding protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a light chain amino acid sequence selected from the group consisting of SEQ ID NOS:63, 64, 65, 66, 67, 68, 69, and 70. In another variation, the antigen binding protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a heavy chain amino acid sequence selected from the group consisting of SEQ ID NOS:17, 18, 19, 20, 21, 22, 23, and 24. In yet a further embodiment, the antigen binding protein comprises A) an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a light chain amino acid sequence selected from the group consisting of SEQ ID NOS:63, 64, 65, 66, 67, 68, 69, and 70, and B) an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a heavy chain amino acid sequence selected from the group consisting of SEQ ID NOS:17, 18, 19, 20, 21, 22, 23, and 24.

In certain embodiments, the antigen binding protein comprises a light chain and/or heavy chain CDR3. In some embodiments, the antigen binding protein comprises an amino acid sequence selected from the group of sequences set forth in SEQ ID NOS:87, 88, 89, 90, 91, 92, 93, 94, 41, 42, 43, 44, 45, 46, 47, and 48. In certain embodiments, the amino acid sequence includes no more than one, no more than two, no more than three, no more than four, no more than five, or no more than six amino acid additions, deletions, or substitutions from the exemplary sequence set forth in SEQ ID NOS:87, 88, 89, 90, 91, 92, 93, 94, 41, 42, 43, 44, 45, 46, 47, and 48. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS:87, 88, 89, 90, 91, 92, 93, 94, 41, 42, 43, 44, 45, 46, 47, and 48.

In certain embodiments, the antigen binding protein comprises a light chain and/or heavy chain CDR2. In some embodiments, the antigen binding protein comprises an amino acid sequence selected from the group of sequences set forth in SEQ ID NOS:79, 80, 81, 82, 83, 84, 85, 86, 33, 34, 35, 36, 37, 38, 39, and 40. In certain embodiments, the amino acid sequence includes no more than one, no more than two, no more than three, no more than four, no more than five, or no more than six amino acid additions, deletions, or substitutions from the exemplary sequence set forth in SEQ ID NOS: 79, 80, 81, 82, 83, 84, 85, 86, 33, 34, 35, 36, 37, 38, 39, and 40. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS: 79, 80, 81, 82, 83, 84, 85, 86, 33, 34, 35, 36, 37, 38, 39, and 40.

In certain embodiments, the antigen binding protein comprises a light chain and/or heavy chain CDR1. In some embodiments, the antigen binding protein comprises an amino acid sequence selected from the group of sequences set forth in SEQ ID NOS:71, 72, 73, 74, 75, 76, 77, 78, 25, 26, 27, 28, 29, 30, 31, and 32. In certain embodiments, the amino acid sequence includes no more than one, no more than two, no more than three, no more than four, no more than five, or no more than six amino acid additions, deletions, or substitutions from the exemplary sequence set forth in SEQ ID NOS: 71, 72, 73, 74, 75, 76, 77, 78, 25, 26, 27, 28, 29, 30, 31, and 32. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS: 71, 72, 73, 74, 75, 76, 77, 78, 25, 26, 27, 28, 29, 30, 31, and 32.

The antigen binding proteins of the invention comprise the scaffolds of traditional antibodies, including human and monoclonal antibodies, bispecific antibodies, diabodies, minibodies, domain antibodies, synthetic antibodies (sometimes referred to herein as "antibody mimetics"), chimeric antibodies, antibody fusions (sometimes referred to as "antibody conjugates"), and fragments of each, respectively. The above described CDRs, including various combinations of the CDRs, may be grafted into any of the following scaffolds.

As used herein, the term "antibody" refers to the various forms of monomeric or multimeric proteins comprising one or more polypeptide chains that specifically binds to an antigen, as variously described herein. In certain embodiments, antibodies are produced by recombinant DNA techniques. In additional embodiments, antibodies are produced by enzymatic or chemical cleavage of naturally occurring antibodies. In another aspect, the antibody is selected from the group consisting of: a) a human antibody; b) a humanized antibody; c) a chimeric antibody; d) a monoclonal antibody; e) a polyclonal antibody; f) a recombinant antibody; g) an antigen-binding fragment; h) a single chain antibody; i) a diabody; j) a triabody, k) a tetrabody, l) a Fab fragment; m) a F(ab')$_2$ fragment, n) an IgA antibody, o) an IgD antibody, p) an IgE antibody, q) an IgG1 antibody, r) an IgG2 antibody, s) an IgG3 antibody, t) an IgG4 antibody, and u) an IgM antibody.

A variable region comprises at least three heavy or light chain CDRs embedded within a framework region (designated framework regions FR1, FR2, FR3, and FR4). Kabat et al., 1991, *Sequences of Proteins of Immunological Interest*, Public Health Service N.I.H., Bethesda, Md. Traditional antibody structural units typically comprise a tetramer. Each tetramer is typically composed of two identical pairs of polypeptide chains, each pair having one "light" and one "heavy" chain. The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to IgM1 and IgM2. Embodiments of the invention include all such classes and subclasses of antibodies that incorporate a variable domain or CDR of the antigen binding proteins, as described herein.

Some naturally occurring antibodies, such as those found in camels and llamas, are dimers consisting of two heavy chains and include no light chains. The invention encompasses dimeric antibodies of two heavy chains, or fragments thereof, that can bind to CD27L.

The variable regions of the heavy and light chains typically exhibit the same general structure of relatively conserved framework regions (FR) joined by three hypervariable regions, i.e., the complementarity determining regions or CDRs. The CDRs are primarily responsible for antigen recognition and binding. The CDRs fromt eh two chains of each pair are aligned by the framework regions, enabling binding to a specific epitope. From N-terminal to C-terminal, both light and heavy chains comprise the domains FR1, CDR1, FR2, CDR2, FR3, CDR3, and FR4. The assignment of amino acids to each domain is in accordance with the definitions of Kabat.

CDRs constitute the major surface contact points for antigen binding. The CDR3 or the light chain and, particularly, CDR3 of the heavy chain may constitute the most important determinants in antigen binding within the light and heavy chain variable regions. In some antibodies, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen.

Naturally occurring antibodies typically include a signal sequence, which directs the antibody into the cellular pathway for protein secretion and which is typically not present in the mature antibody. A polynucleotide encoding an antibody of the invention may encode a naturally occurring a signal sequence or a heterologous signal sequence as described below.

In one embodiment, the antigen binding protein is a antibody comprising from one to six of the exemplary CDRs described herein. The antibodies of the invention may be of any type including IgM, IgG (including IgG1, IgG2, IgG3, IgG4), IgD, IgA, or IgE antibody. In a specific embodiment the antigen biding protein is an IgG type antibody, e.g., a IgG1 antibody.

In some embodiments, for example when the antigen binding protein is an antibody with complete heavy and light chains, the CDRs are all from the same species, e.g., human. Alternatively, for example in embodiments wherein the antigen binding protein contains less than six CDRs from the sequences outlined above, additional CDRs may be either from other species or may be different human CDRs than those depicted in the exemplary sequences. For example, HCDR3 and LCDR3 regions from the appropriate sequences identified herein may be used with HCDR1, HCDR2, LCDR1, and LCDR2 being optionally selected from alternate species or different human antibody sequences, or combinations thereof. For example, the CDRs of the invention can replace the CDR regions of commercially relevant chimeric or humanized antibodies.

Specific embodiments utilize scaffold components of the antigen binding proteins that are human components. In some embodiments, however, the scaffold components can be a mixture from different species. As such, if the antigen binding protein is an antibody, such antibody may be a chimeric antibody and/or humanized antibody. In general, both "chimeric antibodies" and humanized antibodies" refer to antibodies that combine regions from more than one species. For example, "chimeric antibodies" traditionally comprise variable region(s) from a mouse (or rat, in some casaes) and the constant region(s) from a human.

"Humanized antibodies" generally refer to non-human antibodies that have had the variable domain framework regions swapped for sequences found in human antibodies. Generally, in a humanized antibody, the entire antibody, except one or more CDRs, is encoded by a polynucleotide of human origin or is identical to such an antibody except within one or more CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones 1986, *Nature* 321:522-525, Verhoeyen et al., 1988, *Science* 239:1534-1536. Humanized antibodies can also be generated using mice with a genetically engineered immune system. Roque et al., 2004, Biotechnol. Prog. 20:639-654. In the exemplary embodiments described herein, the identified CDRs are human, and thus both humanized and chimeric antibodies in this context include some non-human CDRs; for example, humanized antibodies may be generated that comprise the HCDR3 and LCDR3 regions, with one or more of the other CDR regions being of a different species origin.

In one embodiment, the CD27L antigen binding protein is a mutlispecific antibody, and notably a bispecfic antibody, also sometimes referred to as "diabodies." These are antibodies that bind to two or more different antigens or different epitopes on a single antigen. In certain embodiments, a bispecific antibody binds CD27L and an antigen on a human effector cell (e.g., T cell). Such antibodies are useful in targeting an effector cell response against a CD27L expressing cells, such as a tumor cell. In preferred embodiments, the human effector cell antigen is CD3. U.S. Pat. No. 7,235,641. Methods of making bispecific antibodies are known in the art. One such method involves engineering the Fc portion of the heavy chains such as to create "knobs" and "holes" which facilitate heterodimer formation of the heavy chains when co-expressed in a cell. U.S. Pat. No. 7,695,963. Another method also involves engineering the Fc portion of the heavy chain but uses electrostatic steering to encourage heterodimer formation while discouraging homodimer formation of the heavy chains when co-expressed in a cell. WO 09/089,004, which is incorporated herein by reference in its entirety.

In one embodiment, the CD27L antigen binding protein is a minibody. Minibodies are minimized antibody-like proteins comprising a scFv joined to a CH3 domain. Hu et al., 1996, *Cancer Res.* 56:3055-3061.

In one embodiment, the CD27L antigen binding protein is a domain antibody; see, for example U.S. Pat. No. 6,248,516. Domain antibodies (dAbs) are functional binding domains of antibodies, corresponding to the variable regions of either the heavy (VH) or light (VL) chains of human antibodies. dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609.

In one embodiment, the CD27L antigen binding protein is an antibody fragment, that is a fragment of any of the antibodies outlined herein that retain binding specificity to CD27L. In various embodiments, the antibody binding proteins comprise, but are not limited to, a F(ab), F(ab'), F(ab')2, Fv, or a single chain Fv fragments. At a minimum, an antibody, as meant herein, comprises a polypeptide that can bind specifically to CD27L comprising all or part of a light or heavy chain variable region, such as one or more CDRs.

Further examples of CD27L-binding antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, *Nature* 341:544-546) which consists of a single variable, (v) isolated CDR regions, (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, *Science* 242: 423-426, Huston et al., 1988, *Proc. Natl. Acad. Sci. U.S.A.* 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448). The antibody fragments may be modified. For example, the molecules may be stabilized by the incorporation of disulphide bridges linking the VH and VL domains (Reiter et al., 1996, *Nature Biotech.* 14:1239-1245). Aspects of the invention include embodiments wherein the non-CDR components of these fragments are human sequences.

In one embodiment, the CD27L antigen binding protein is a fully human antibody. In this embodiment, as outlined above, specific structures comprise complete heavy and light chains depicted comprising the CDR regions. Additional embodiments utilize one or more of the CDRs of the invention, with the other CDRs, framework regions, J and D regions, constant regions, etc., coming from other human antibodies. For example, the CDRs of the invention can replace the CDRs of any number of human antibodies, particularly commercially relevant antibodies Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87. Single chain antibodies derived from antibodies provided herein (including but not limited to scFvs comprising the variable domain combinations of Ab1 LCv/Ab1 HCv (SEQ ID NO:63/SEQ ID NO:17), Ab2 LCv/Ab2 HCv (SEQ ID NO:64/SEQ ID NO:18), Ab3 LCv/Ab3 HCv (SEQ ID NO:65/SEQ ID NO:19), Ab4 LCv/Ab4 HCv (SEQ ID NO:66/SEQ ID NO:20), Ab5 LCv/Ab5 HCv (SEQ ID NO:67/SEQ ID NO:21), Ab6 LCv/Ab6 HCv (SEQ ID NO:68/SEQ ID NO:22), Ab7 LCv/Ab7 HCv (SEQ ID NO:69/SEQ ID NO:23), Ab8 LCv/Ab8 HCv (SEQ ID NO:70/SEQ ID NO:24), and combinations thereof are encompassed by the present invention.

In one embodiment, the CD27L antigen binding protein is an antibody fusion protein (sometimes referred to herein as an "antibody conjugate"). The conjugate partner can be proteinaceous or non-proteinaceous; the latter generally being generated using functional groups on the antigen binding protein and on the conjugate partner. In certain embodiments, the antibody is conjugated to a non-proteinaceous chemical (drug) to form an antibody drug conjugate. Exemplary antibody drug conjugates and methods of making such conjugates are discussed below.

In one embodiment, the CD27L antigen binding protein is an antibody analog, sometimes referred to as "synthetic antibodies." For example, a variety of work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, *Proteins: Structure, Function, and Bioinformatics*, Volume 53, Issue 1:121-129. Roque et al., 2004, *Biotechnol. Prog.* 20:639-654. In addition, peptide antibody mimetics ("PAMs") can be used, as well as work based on antibody mimetics utilizing fibronection components as a scaffold.

By "protein," as used herein, is meant at least two covalently attached amino acids, which includes proteins, polypeptides, oligopeptides and peptides. In some embodiments, the two or more covalently attached amino acids are attached by a peptide bond. The protein may be made up of naturally occurring amino acids and peptide bonds, for example when the protein is made recombinantly using expression systems and host cells, as outlined below. Alternatively, the protein may include synthetic amino acids (e.g., homophenylalanine, citrulline, ornithine, and norleucine), or peptidomimetic structures, i.e., "peptide or protein analogs", such as peptoids (see, Simon et al., 1992, *Proc. Natl. Acad. Sci. U.S.A.* 89:9367, incorporated by reference herein), which can be resistant to proteases or other physiological and/or storage conditions. Such synthetic amino acids may be incorporated in particular when the antigen binding protein is synthesized in vitro by conventional methods well known in the art. In addition, any combination of peptidomimetic, synthetic and naturally occurring residues/structures can be used. "Amino acid" also includes imino acid residues such as proline and hydroxyproline. The amino acid "R group" or "side chain" may be in either the (L)- or the (S)-configuration. In a specific embodiment, the amino acids are in the (L)- or (S)-configuration.

In certain aspects, the invention provides recombinant antigen binding proteins that bind a CD27L and, in some embodiments, a recombinant human CD27L or portion thereof. In this context, a "recombinant protein" is a protein made using recombinant techniques using any techniques and methods known in the art, i.e., through the expression of a recombinant nucleic acid as described herein. Methods and techniques for the production of recombinant proteins are well known in the art. Embodiments of the invention include recombinant antigen binding proteins that bind wild-type CD27L and variants thereof.

"Consisting essentially of" means that the amino acid sequence can vary by about 1, 2, 3, 4, 5, 6, 7, 8, 9, 10, 11, 12, 13, 14, or 15% relative to the recited SEQ ID NO: sequence and still retain biological activity, as described herein.

In some embodiments, the antigen binding proteins of the invention are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antigen binding protein in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, CABIOS 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 80%, and more typically with preferably increasing homologies or identities of at least 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities, such as CD27L binding.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 1.

TABLE 1

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the antigen binding protein proteins as needed. Alternatively, the variant may be designed such that the biological activity of the antigen binding protein is altered. For example, glycosylation sites may be altered or removed as discussed herein.

Other derivatives of CD27L antibodies within the scope of this invention include covalent or aggregative conjugates of CD27L antibodies, or fragments thereof, with other proteins or polypeptides, such as by expression of recombinant fusion proteins comprising heterologous polypeptides fused to the N-terminus or C-terminus of a CD27L antibody polypeptide. For example, the conjugated peptide may be a heterologous signal (or leader) polypeptide, e.g., the yeast alpha-factor leader, or a peptide such as an epitope tag. CD27L antibody-containing fusion proteins can comprise peptides added to facilitate purification or identification of the CD27L antibody (e.g., poly-His). A CD27L antibody polypeptide also can be linked to the FLAG peptide as described in Hopp et al., *Bio/Technology* 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more CD27L antibody polypeptides may be employed as CD27L antagonists. Oligomers may be in the form of covalently-linked or non-covalently-linked dimers, trimers, or higher oligomers. Oligomers comprising two or more CD27L antibody polypeptides are contemplated for use, with one example being a homodimer. Other oligomers include heterodimers, homotrimers, heterotrimers, homotetramers, heterotetramers, etc.

One embodiment is directed to oligomers comprising multiple CD27L antibody polypeptides joined via covalent or non-covalent interactions between peptide moieties fused to the CD27L antibody polypeptides. Such peptides may be peptide linkers (spacers), or peptides that have the property of promoting oligomerization. Leucine zippers and certain polypeptides derived from antibodies are among the peptides that can promote oligomerization of CD27L antibody polypeptides attached thereto, as described in more detail below.

In particular embodiments, the oligomers comprise from two to four CD27L antibody polypeptides. The CD27L antibody moieties of the oligomer may be in any of the forms described above, e.g., variants or fragments. Preferably, the oligomers comprise CD27L antibody polypeptides that have CD27L binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment of the present invention is directed to a dimer comprising two fusion proteins created by fusing a CD27L binding fragment of a CD27L antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a CD27L antibody may be substituted for the variable portion of an antibody heavy and/or light chain.

Alternatively, the oligomer is a fusion protein comprising multiple CD27L antibody polypeptides, with or without peptide linkers (spacer peptides). Among the suitable peptide linkers are those described in U.S. Pat. Nos. 4,751,180 and 4,935,233.

Another method for preparing oligomeric CD27L antibody derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one approach, recombinant fusion proteins comprising CD27L antibody fragment or derivative fused to a leucine zipper peptide are expressed in suitable host cells, and the soluble oligomeric CD27L antibody fragments or derivatives that form are recovered from the culture supernatant.

Covalent modifications of antigen binding proteins are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking antigen binding proteins to a water-insoluble support matrix or surface for use in a variety of methods. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the $\alpha$-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antigen binding protein included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, CRC Crit. Rev. Biochem., pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118: 131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages.

Another type of covalent modification of the antigen binding protein comprises linking the antigen binding protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antigen binding protein to facilitate the addition of polymers such as PEG.

In some embodiments, the covalent modification of the antigen binding proteins of the invention comprises the addition of one or more labels.

The term "labelling group" means any detectable label. Examples of suitable labelling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, $\beta$-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, $\beta$-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antigen binding protein via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla, Ptilosarcus,* or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

Polynucleotides Encoding CD27L Antigen Binding Proteins

Encompassed within the invention are nucleic acids encoding CD27L antigen binding proteins, including antibodies, as defined herein. Preferred nucleic acids include those that encode the exemplary light and heavy chains described herein.

An exemplary nucleic acid encoding Ab1 LC is a nucleic acid comprising the sequence set forth in SEQ ID NO:49.

An exemplary nucleic acid encoding Ab2 LC is a nucleic acid comprising the sequence set forth in SEQ ID NO:50.

An exemplary nucleic acid encoding Ab4 LC is a nucleic acid comprising the sequence set forth in SEQ ID NO:51.

An exemplary nucleic acid encoding Ab5 LC is a nucleic acid comprising the sequence set forth in SEQ ID NO:52.

An exemplary nucleic acid encoding Ab6 LC is a nucleic acid comprising the sequence set forth in SEQ ID NO:53.

An exemplary nucleic acid encoding Ab7 LC is a nucleic acid comprising the sequence set forth in SEQ ID NO:54.

An exemplary nucleic acid encoding Ab8 LC is a nucleic acid comprising the sequence set forth in SEQ ID NO:55.

An exemplary nucleic acid encoding Ab1 HC is a nucleic acid comprising the sequence set forth in SEQ ID NO:3.

An exemplary nucleic acid encoding Ab2 HC is a nucleic acid comprising the sequence set forth in SEQ ID NO:4.

An exemplary nucleic acid encoding Ab4 HC is a nucleic acid comprising the sequence set forth in SEQ ID NO:5.

An exemplary nucleic acid encoding Ab5 HC is a nucleic acid comprising the sequence set forth in SEQ ID NO:6.

An exemplary nucleic acid encoding Ab6 HC is a nucleic acid comprising the sequence set forth in SEQ ID NO:7.

An exemplary nucleic acid encoding Ab7 HC is a nucleic acid comprising the sequence set forth in SEQ ID NO:8.

An exemplary nucleic acid encoding Ab8 HC is a nucleic acid comprising the sequence set forth in SEQ ID NO:9.

Aspects of the invention include polynucleotide variants (e.g., due to degeneracy) that encode the amino acid sequences described herein.

Aspects of the invention include a variety of embodiments including, but not limited to, the following exemplary embodiments.

An isolated polynucleotide, wherein said polynucleotide encodes one or more polypeptides comprising an amino acid sequence selected from the group consisting of:

A. 1. a light chain variable domain sequence that is at least 90% identical to a light chain variable domain sequence set forth in SEQ ID NOs:63-70;
  2. a heavy chain variable domain sequence that is at least 90% identical to a heavy chain variable domain sequence set forth in SEQ ID NOs:17-24;
  3. a light chain variable domain of (1) and a heavy chain variable domain of (2); and B. a light chain variable domain comprising a CDR1, CDR2, CDR3 and/or a heavy chain variable domain comprising a CDR1, CDR2, CDR3 that differ by no more than a total of three amino acid additions, substitutions, and/or deletions in each CDR from the following sequences:
  1. a light chain CDR1 (SEQ ID NO:71), CDR2 (SEQ ID NO:79), CDR3 (SEQ ID NO:87) or a heavy chain CDR1 (SEQ ID NO:25), CDR2 (SEQ ID NO:33), CDR3 (SEQ ID NO:41) of Ab1;
  2. a light chain CDR1 (SEQ ID NO:72), CDR2 (SEQ ID NO:80), CDR3 (SEQ ID NO:88) or a heavy chain CDR1 (SEQ ID NO:26), CDR2 (SEQ ID NO:34), CDR3 (SEQ ID NO:42) of Ab2;
  3. a light chain CDR1 (SEQ ID NO:73), CDR2 (SEQ ID NO:81), CDR3 (SEQ ID NO:89) or a heavy chain CDR1 (SEQ ID NO:27), CDR2 (SEQ ID NO:35), CDR3 (SEQ ID NO:43) of Ab3;
  4. a light chain CDR1 (SEQ ID NO:74), CDR2 (SEQ ID NO:82), CDR3 (SEQ ID NO:90) or a heavy chain CDR1 (SEQ ID NO:28), CDR2 (SEQ ID NO:36), CDR3 (SEQ ID NO:44) of Ab4;
  5. a light chain CDR1 (SEQ ID NO:75), CDR2 (SEQ ID NO:83), CDR3 (SEQ ID NO:91) or a heavy chain CDR1 (SEQ ID NO:29), CDR2 (SEQ ID NO:37), CDR3 (SEQ ID NO:45) of Ab5;
  6. a light chain CDR1 (SEQ ID NO:76), CDR2 (SEQ ID NO:84), CDR3 (SEQ ID NO:92) or a heavy chain CDR1 (SEQ ID NO:30), CDR2 (SEQ ID NO:38), CDR3 (SEQ ID NO:46) of Ab6;
  7. a light chain CDR1 (SEQ ID NO:77), CDR2 (SEQ ID NO:85), CDR3 (SEQ ID NO:93) or a heavy chain CDR1 (SEQ ID NO:31), CDR2 (SEQ ID NO:39), CDR3 (SEQ ID NO:47) of Ab7; and
  8. a light chain CDR1 (SEQ ID NO:78), CDR2 (SEQ ID NO:86), CDR3 (SEQ ID NO:94) or a heavy chain CDR1 (SEQ ID NO:32), CDR2 (SEQ ID NO:40), CDR3 (SEQ ID NO:48) of Ab8.

In preferred embodiments, the polypeptide encoded by the isolated nucleic acid is a component of an antigen binding protein that binds CD27L.

Nucleotide sequences corresponding to the amino acid sequences described herein, to be used as probes or primers for the isolation of nucleic acids or as query sequences for database searches, can be obtained by "back-translation"

from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a CD27L antigen binding proteins or a desired combination of CD27L antigen binding protein polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids that hybridize under moderately stringent conditions, and more preferably highly stringent conditions, to nucleic acids encoding CD27L antigen binding proteins as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH.sub.2 PO.sub.4, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10.degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6($\log_{10}$ [$Na^+$])+0.41(% G+C)−(600/N), where N is the number of bases in the hybrid, and [$Na^+$] is the concentration of sodium ions in the hybridization buffer ([$Na^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

The variants according to the invention are ordinarily prepared by site specific mutagenesis of nucleotides in the DNA encoding the antigen binding protein, using cassette or PCR mutagenesis or other techniques well known in the art, to produce DNA encoding the variant, and thereafter expressing the recombinant DNA in cell culture as outlined herein. However, antigen binding protein fragments comprising variant CDRs having up to about 100-150 residues may be prepared by in vitro synthesis using established techniques. The variants typically exhibit the same qualitative biological activity as the naturally occurring analogue, e.g., binding to CD27L, although variants can also be selected which have modified characteristics as will be more fully outlined below.

As will be appreciated by those in the art, due to the degeneracy of the genetic code, an extremely large number of nucleic acids may be made, all of which encode the CDRs (and heavy and light chains or other components of the antigen binding protein) of the present invention. Thus, having identified a particular amino acid sequence, those skilled in the art could make any number of different nucleic acids, by simply modifying the sequence of one or more codons in a way which does not change the amino acid sequence of the encoded protein.

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the CD27L antigen binding protein coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the CD27L antigen binding protein from the host cell. Affinity purification can be accomplished, for example, by column chromatography using antibodies against the tag as an affinity matrix. Optionally, the tag can subsequently be removed from the purified CD27L antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thyrnidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein antibody that binds to CD27L polypeptide. As a result, increased quantities of a polypeptide such as an CD27L antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the CD27L antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an CD27L antigen binding protein of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (VIIIa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315: 115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising a CD27L antigen binding protein of the invention by higher eukaryotes. Enhancers are cis-acting elements of DNA, usually about 10-300 by in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-fetoprotein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat.

No. 4,968,607; the type II interleukin-1 receptor signal peptide described in EP Patent No. 0 460 846.

The vector may contain one or more elements that facilitate expression when the vector is integrated into the host cell genome. Examples include an EASE element (Aldrich et al. 2003 *Biotechnol Prog.* 19:1433-38) and a matrix attachment region (MAR). MARs mediate structural organization of the chromatin and may insulate the integrated vactor from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an CD27L antigen binding sequence has been inserted into the proper site of the vector, the completed vector may be inserted into a suitable host cell for amplification and/or polypeptide expression. The transformation of an expression vector for an CD27L antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an CD27L antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention. In general, host cells are transformed with a recombinant expression vector that comprises DNA encoding a desired anti-CD27L antibody polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., 1998, *Cytotechnology* 28: 31), HeLa cells, BHK (ATCC CRL 10) cell lines, and the CVI/EBNA cell line derived from the African green monkey kidney cell line CV1 (ATCC CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces strains, Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods. The polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, *Bio/Technology* 6:47 (1988). Cell-free translation systems could also be employed to produce polypeptides using RNAs derived from nucleic acid constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, New York, 1985). A host cell that comprises an isolated nucleic acid of the invention, preferably operably linked to at least one expression control sequence, is a "recombinant host cell".

In certain embodiments, cell lines may be selected through determining which cell lines have high expression levels and constitutively produce antigen binding proteins with CD27L binding properties. In another embodiment, a cell line from the B cell lineage that does not make its own antibody but has a capacity to make and secrete a heterologous antibody can be selected.

Antibody Drug Conjugates

Embodiments of the invention include antibody drug conjugates (ADCs). Generally the ADC comprises an antibody conjugated to a chemotherapeutic agent, e.g., a cytotoxic agent, a cytostatic agent, a toxin, or a radioactive agent. A linker molecule can be used to conjugate the drug to the antibody. A wide variety of linkers and drugs useful in ADC technology are known in the art and may be used in embodiments of the present invention. (See US20090028856; US2009/0274713; US2007/0031402; WO2005/084390; WO2009/099728; U.S. Pat. No. 5,208,020; U.S. Pat. No. 5,416,064; U.S. Pat. Nos. 5,475,092; 5,585,499; 6,436,931; 6,372,738; and 6340701, all incorporated herein by reference).

The antibody drug conjugates may be prepared by in vitro methods. In order to link a drug or prodrug to the antibody, a linking group is used. Suitable linking groups are well known in the art and include disulfide groups, acid labile groups, photolabile groups, peptidase labile groups, and esterase labile groups. Preferred linking groups are disulfide groups. For example, conjugates can be constructed using a disulfide exchange reaction between the antibody and the drug or prodrug. The drug molecules also can be linked to a cell binding agent through an intermediary carrier molecule such as serum albumin.

In certain embodiments, the cell binding agent is modified by reacting a bifunctional crosslinking reagent with the cell binding agent, thereby resulting in the covalent attachment of a linker molecule to the cell binding agent. As used herein, a "bifunctional crosslinking reagent" or "linker" is any chemical moiety that covalently links a cell binding agent to a drug, such as the drugs described herein. In a particular embodiment of the invention, a portion of the linking moiety is provided by the drug. In this respect, the drug comprises a linking moiety that is part of a larger linker molecule that is used to join the cell binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

Any suitable bifunctional crosslinking reagent can be used in connection with the invention, so long as the linker reagent provides for retention of the therapeutic, e.g., cytotoxicity, and targeting characteristics of the drug and the cell binding agent, respectively. Preferably, the linker molecule joins the drug to the cell binding agent through chemical bonds (as described above), such that the drug and the cell binding agent are chemically coupled (e.g., covalently bonded) to each other.

Linkers

In certain embodiments, the ADC comprises a linker made up of one or more linker components. Preferably the drug is linked to a cell binding agent through a disulfide bond. The linker molecule comprises a reactive chemical group that can react with the cell binding agent. Preferred reactive chemical groups for reaction with the cell binding agent are N-succinimidyl esters and N-sulfosuccinimidyl esters. Additionally the linker molecule comprises a reactive chemical group, preferably a dithiopyridyl group, that can react with the drug to form a disulfide bond. Exemplary linker molecules include, for example, N-succinimidyl 3-(2-pyridyldithio)propionate (SPDP) (see, e.g., Carlsson et al., Biochem. J., 173, 723-737 (1978)), N-succinimidyl 4-(2-pyridyldithio)butanoate (SPDB) (see, e.g., U.S. Pat. No. 4,563,304) and N-succinimidyl 4-(2-pyridyldithio)pentanoate (SPP) (see, e.g., CAS Registry number 341498-08-6). Additional exemplary linker components include 6-maleimidocaproyl, maleimidopropanoyl, valine-citrulline, alanine-phenylalanine, p-aminobenzyloxycarbonyl, and those resulting from conjugation with linker reagents, including, but not limited to, N-succinimidyl 4-(2-pyridylthio)pentanoate ("SPP"), N-succinimidyl 4-(N-maleimidomethyl)cyclohexane-1 carboxylate ("SMCC," also referred to herein also as "MCC"), and N-succinimidyl (4-iodo-acetyl)aminobenzoate ("SIAB").

Linkers may be a "cleavable" linker or a "non-cleavable" linker (Ducry and Stump, *Bioconjugate Chem.* 2010, 21, 5-13; incorporated herein by reference in its entirety) Cleavable linkers are designed to release the drug when subjected to certain environment factors, e.g., when internalized into the target cell. Cleavable linkers include acid labile linkers, protease sensitive linkers, photolabile linkers, dimethyl linker or disulfide-containing linkers. Non-cleavable linkers tend to remain covalently associated with at least one amino acid of the antibody and the drug upon internalization by and degradation within the target cell. A non-cleavable linker is any chemical moiety that is capable of linking a drug, such as a maytansinoid (e.g., DM1, and the like), a taxane, or a CC-1065 analog, to a cell binding agent in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the drug or the cell binding agent remains active.

Suitable crosslinking reagents that form non-cleavable linkers between a drug and the cell-binding agent are well known in the art. Examples of non-cleavable linkers include linkers having an N-succinimidyl ester or N-sulfosuccinimidyl ester moiety for reaction with the cell binding agent, as well as a maleimido- or haloacetyl-based moiety for reaction with the drug. Crosslinking linker reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), x-maleimidoundecanoic acid N-succinimidyl ester (KMUA), .gamma.-maleimidobutyric acid N-succinimidyl ester (GMBS), .epsilon.-maleimidocaproic acid N-hydroxysuccinimide ester (EMCS), m-maleimidobenzoyl-N-hydroxysuccinimide ester (MBS), N-(.alpha.-maleimidoacetoxy)-succinimide ester (AMAS), succinimidyl-6-(.beta.-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP). An exemplary preferred non-cleavable linker is MCC.

Other crosslinking reagent linkers lacking a sulfur atom that form non-cleavable linkers can also be used in the inventive method. Such linkers can be derived from dicarboxylic acid based moieties. Suitable dicarboxylic acid based moieties include, but are not limited to, alpha, omega-dicarboxylic acids of the general formula (IX):

$$HOOC-X_1-Y_n-Z_m-COOH \qquad (IX),$$

wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. Patent Application Publication 2005/0169933 A1.

Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., Proc. Natl. Acad. Sci. USA, 79, 626-629 (1982), and Umemoto et al., Int. J. Cancer, 43, 677-684 (1989)).

Drugs

In certain embodiments, the antibody is conjugated to a chemotherapeutic agent. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin gammal and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above. Other chemotherapeutic agents that can be used with the present invention are disclosed in US Publication No. 20080171040 or US Publication No. 20080305044 and are incorporated in their entirety by reference.

It is contemplated that an antibody may be conjugated to two or more different chemotherapeutic agents or a pharmaceutical composition may comprise a mixture of antibodies wherein the antibody component is identical except for being conjugated to a different chemotherapeutic agent. Such embodiments may be useful for targeting multiple biological pathways with a target cell.

In preferred embodiments, the ADC comprises an antibody conjugated to one or more maytansinoid molecules, which are mitotic inhibitors that act by inhibiting tubulin polymerization. Maytansinoids, including various modifications, are described in U.S. Pat. Nos. 3,896,111; 4,151,042; 4,137,230; 4,248,870; 4,256,746; 4,260,608; 4,265,814; 4,294,757; 4,307,016; 4,308,268; 4,309,428; 4,313,946; 4,315,929; 4,317,821; 4,322,348; 4,331,598; 4,361,650; 4,364,866; 4,424,219; 4,450,254; 4,362,663; 4,371,533; and WO 2009/099728. Maytansinoid drug moieties may be isolated from natural sources, produced using recombinant technology, or prepared synthetically. Exemplary maytansinoids include C-19-dechloro (U.S. Pat. No. 4,256,746), C-20-hydroxy (or C-20-demethyl)+/−C-19-dechloro (U.S. Pat. Nos. 4,307,016 and 4,361,650), C-20-demethoxy (or C-20-acyloxy (—OCOR), +/−dechrolo (U.S. Pat. No. 4,294,757), C-9-SH (U.S. Pat. No. 4,424,219), C-14-alkoxymethyl (demethoxy/CH2OR) (U.S. Pat. No. 4,331,598), C-14-hydroxymethyl or acyloxymethyl (CH2OH or CH2OAc) (U.S. Pat. No. 4,450,254), C-15-hydroxy/acyloxy (U.S. Pat. No. 4,364,866), C-15-methoxy (U.S. Pat. Nos. 4,313,946 and 4,315,929), C-18-N-demethyl (U.S. Pat. Nos. 4,362,663 and 4,322,348), and 4,5-deoxy (U.S. Pat. No. 4,371,533).

Various positions on maytansinoid compounds may be used as the linkage position, depending upon the type of link desired. For example, for forming an ester linkage, the C-3 position having a hydroxyl group, the C-14 position modified with hydrozymethyl, the C-15 position modified with a hydroxyl a group, and the C-20 position having a hydroxyl group are all suitable (U.S. Pat. Nos. 5,208,020, RE39151, and 6,913,748; US Patent Appl. Pub. Nos. 20060167245 and 20070037972, and WO 2009099728).

Preferred maytansinoids include those known in the art as DM1, DM3, and DM4 (US Pat. Appl. Pub. Nos. 2009030924 and 20050276812, incorporated herein by reference).

ADCs containing maytansinoids, methods of making such ADCs, and their therapeutic use are disclosed in U.S. Pat. Nos. 5,208,020 and 5,416,064, US Pat. Appl. Pub. No. 20050276812, and WO 2009099728 (all incorporated by reference herein). Linkers that are useful for making maytansinoid ADCs are know in the art (U.S. Pat. No. 5,208,020 and US Pat. Appl. Pub. Nos. 2005016993 and 20090274713; all incorporated herein by reference). Maytansinoid ADCs comprising an SMCC linker may be prepared as disclosed in US Pat. Publ. No. 2005/0276812.

In certain embodiments, the ADC comprises an antibody conjugated to DM1 with an SMCC linker. Preferred embodiments include Ab1-SMCC-DM1, Ab2-SMCC-DM1, Ab3-SMCC-DM1, Ab4-SMCC-DM1, Ab5-SMCC-DM1, Ab6-SMCC-DM1, Ab7-SMCC-DM1, and Ab8-SMCC-DM1.

Drug Loading

An ADC may have 1 to 20 chemotherapeutic agents per antibody. Compositions of ADCs may be characterized by the average number of drug moieties per antibody molecule in the composition. The average number of drug moieties may be determined by conventional means such as mass spectrometry, immunoassay, and HPLC. In some instances, a homogeneous ADC population may be separated and purified by means of reverse phase HPLC or electrophoresis. Thus, pharmaceutical ADC compositions may contain a heterogeneous or homogeneous population of antibodies linked to 1, 2, 3, 4, 5, 6, 7 or more drug moieties.

In preferred embodiments, the ADC comprises as antibody conjugated to one or more DM1 molecules. Embodiments of the invention include compositions comprising an average of about 1, about 2, about 3, about 4, about 5, about 6, about 7, about 8, about 9, about 10, about 11, about 12, about 13, about 14, about 15, about 16, about 17, about 18, about 19, or about 20 DM1 molecules per antibody. Preferred ADC compositions are those comprising an Ab1, Ab2, Ab3, Ab4, Ab5, Ab6, Ab7, or Ab8 having on average between 1 and 10 DM1 molecules per antibody, those comprising antibodies having on average between 3 and 7 DM1 molecules per antibody, and those comprising antibodies having on average between 4 and 6 DM1 molecules, including an average of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9 and about 6.0 DM1 molecules per antibody.

Effector Function-Enhanced Antibodies

One of the functions of the Fc portion of an antibody is to communicate to the immune system when the antibody binds its target. This is considered "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fc with proteins of the complement system, e.g., Clq.

The IgG subclasses vary in their ability to mediate effector functions. For example IgG1 is much superior to IgG2 and IgG4 at mediating ADCC and CDC. Thus, in embodiments wherein a cell expressing CD27L is targeted for destruction, an anti-CD27L IgG1 antibody would be preferred.

The effector function of an antibody can be increased, or decreased, by introducing one or more mutations into the Fc. Embodiments of the invention include antigen binding proteins, e.g., antibodies, having an Fc engineered to increase effector function (U.S. Pat. No. 7,317,091 and Strohl, *Curr. Opin. Biotech.*, 20:685-691, 2009; both incorporated herein by reference in its entirety). Exemplary IgG1 Fc molecules having increased effector function include (based on the Kabat numbering scheme) those have the following substitutions: S239D/I332E
S239D/A330S/I332E
S239D/A330L/I332E
S298A/D333A/K334A
P247I/A339D
P247I/A339Q
D280H/K290S
D280H/K290S/S298D
D280H/K290S/S298V
F243L/R292P/Y300L
F243L/R292P/Y300L/P396L
F243L/R292P/Y300LN3051/P396L
G236A/S239D/I332E
K326A/E333A
K326W/E333S
K290E/S298G/T299A
K290N/S298G/T299A
K290E/S298G/T299A/K326E
K290N/S298G/T299A/K326E Further embodiments of the invention include antigen binding proteins, e.g., antibodies, having an Fc engineered to decrease effector function. Exemplary Fc molecules having decreased effector function include (based on the Kabat numbering scheme) those have the following substitutions:
N297A (IgG1)
L234A/L235A (IgG1)
V234A/G237A (IgG2)
L235A/G237A/E318A (IgG4)
H268Q/V309L/A330S/A331S (IgG2)
C220S/C226S/C229S/P238S (IgG1)
C226S/C229S/E233P/L234V/L235A (IgG1)
L234F/L235E/P331S (IgG1)
S267E/L328F (IgG1)

Another method of increasing effector function of IgG Fc-containing proteins is by reducing the fucosylation of the Fc. Removal of the core fucose from the biantennary complex-type oligosachharides attached to the Fc greatly increased ADCC effector function without altering antigen binding or CDC effector function. Several ways are known for reducing or abolishing fucosylation of Fc-containing molecules, e.g., antibodies. These include recombinant expression in certain mammalian cell lines including a FUT8 knockout cell line, variant CHO line Lec13, rat hybridoma cell line YB2/0, a cell line comprising a small interfering RNA specifically against the FUT8 gene, and a cell line coexpressing B-1,4-N-acetylglucosaminyltransferase III and Golgi α-mannosidase II. Alternatively, the Fc-containing molecule may be expressed in a non-mammalian cell such as a plant cell, yeast, or prokaryotic cell, e.g., *E. coli*. Thus, in certain embodiments of the invention, a composition comprises an antibody, e.g., Ab1, Ab2, Ab3, Ab4, Ab5, Ab6, Ab7, or Ab8, having reduced fucosylation or lacking fucosylation altogether.

Pharmaceutical Compositions

In some embodiments, the invention provides a pharmaceutical composition comprising a therapeutically effective amount of one or a plurality of the antigen binding proteins of the invention together with a pharmaceutically effective diluents, carrier, solubilizer, emulsifier, preservative, and/or adjuvant. In certain embodiments, the antigen binding protein is an antibody, including a drug-conjugated antibody or a bispecific antibody. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of a CD27L antigen binding protein, e.g., a CD27L-binding ADC, are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, CD27L antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the CD27L antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired CD27L antigen binding protein in a pharmaceutically acceptable vehicle. A particularly suitable vehicle for parenteral injection is sterile distilled water in which the CD27L antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, CD27L antigen binding proteins are advantageously formulated as a dry, inhalable powder. In specific embodiments, CD27L antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. CD27L antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the CD27L antigen binding protein. Diluents, flavorings, low melting point waxes, vegetable oils, lubricants, suspending agents, tablet disintegrating agents, and binders may also be employed.

Additional pharmaceutical compositions will be evident to those skilled in the art, including formulations involving CD27L antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036, 676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering CD27L antigen binding protein formulations, which can be used as pharmaceutical compositions, as described in international patent application WO 06138181A2 (PCT/US2006/022599), which is incorporated by reference in its entirety herein.

As discussed above, certain embodiments provide CD27L antigen binding proteins protein compositions, particularly pharmaceutical CD27L antigen binding protein compositions, that comprise, in addition to the CD27L antigen binding protein, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofineister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in CD27L antigen binding protein formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the CD27L antigen binding protein formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of CD27L antigen binding protein formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the CD27L antigen binding protein formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol.

Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized-dual chamber cartridge, Pharmacia & Upjohn) contain phenol while Somatrope (Eli Lilly) is formulated with m-cresol.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (.about.18 to 24 months). An important point to note is that preservative effectiveness should be demonstrated in the final formulation containing the active drug and all excipient components.

CD27L antigen binding protein formulations generally will be designed for specific routes and methods of administration, for specific administration dosages and frequencies of administration, for specific treatments of specific diseases, with ranges of bio-availability and persistence, among other things. Formulations thus may be designed in accordance with the invention for delivery by any suitable route, including but not limited to orally, aurally, opthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of a CD27L antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the CD27L antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of a CD27L antigen binding protein preferably results in a decrease in severity of disease symptoms, in increase in frequency or duration of disease symptom-free periods or a prevention of impairment or disability due to the disease affliction. For treating CD27L-expressing tumors, a therapeutically effective amount of CD27L antigen binding protein, e.g. an anti-CD27L ADC, preferably inhibits cell growth or tumor growth by at least about 20%, at least about 40%, at least about 50%, at least about 60%, at least about 70%, at least about 80%, or at least about 90% relative to untreated patients. The ability of a compound to inhibit tumor growth may be evaluated in an animal model predictive of efficacy in human tumors.

Pharmaceutical compositions may be administered using a medical device. Examples of medical devices for administering pharmaceutical compositions are described in U.S. Pat. Nos. 4,475,196; 4,439,196; 4,447,224; 4,447,233; 4,486,194; 4,487,603; 4,596,556; 4,790,824; 4,941,880; 5,064,413; 5,312,335; 5,312,335; 5,383,851; and 5,399,163, all incorporated by reference herein.

Methods of Diagnosing or Treating a CD27L-Associated Disease or Disorder

The CD27L antigen binding proteins of the invention are particularly useful for detecting CD27L in a biological sample. In certain embodiments, a biological sample obtained from a patient is contacted with a CD27L antigen binding protein. Binding of the CD27L antigen binding protein to CD27L is then detected to determine the presence or relative amount of CD27L in the sample. Such methods may be useful in diagnosing or determining patients that are amenable to treatment with a CD27L antigen binding protein, e.g., an anti-CD27L ADC.

In certain embodiments, a CD27L antigen binding protein of the invention is used to diagnose, detect, or treat an autoimmune or inflammatory disorder. In treating autoimmune or inflammatory disorders, the CD27L antigen binding protein may target CD27L-expressing cells of the immune system for destruction and/or may block the interaction of CD27L with the receptor CD27.

CD27L interaction with CD27 is thought to play a role in cell-mediated autoimmune diseases, such as experimental autoimmune encephalomyelitis (EAE) (Nakajima et al. (2000) J. Neuroimmunol. 109:188-96). This effect is thought to be mediated in part by an inhibition of TNF-a production. Furthermore, blocking of CD27L signaling inhibits CD40-mediated clonal expansion of CD8+ T-cells and reduces the generation of CD8+ memory T-cells (Taraban et al. (2004) J. Immunol. 173:6542-6). As such, the CD27L antigen binding proteins can be used to treat a subject with an autoimmune disorder, e.g., a disorder characterized by the presence of B-cells expressing CD27L including, for example, experimental autoimmune encephalomyelitis. Additional autoimmune disorders in which the antibodies of this disclosure can be used include, but are not limited to systemic lupus erythematosus (SLE), insulin dependent diabetes mellitus (IDDM), inflammatory bowel disease (IBD) (including Crohn's Disease, ulcerative colitis and Celiac disease), multiple sclerosis (MS), psoriasis, autoimmune thyroiditis, rheumatoid arthritis (RA) and glomerulonephritis. Furthermore, the cd27L antigen binding protein compositions of this disclosure can be used for inhibiting or preventing transplant rejection or in the treatment of graft versus host disease (GVHD).

Additionally, the interaction of CD27L with CD27 has also been proposed to play a role in signaling on CD4+ T cells. Some viruses have been shown to signal the CD27 pathway, leading to destruction of neutralizing antibody responses (Matter et al. (2006) J Exp Med 203:2145-55). As such, the CD27L antigen binding protein compositions and methods of the present disclosure can be used to treat a subject with a viral infection including, for example, infections from human immunodeficiency virus (HIV), Hepatitis (A, B, & C), Herpesvirus, (e.g., VZV, HSV-1, HAV-6, HSV-II and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus and lymphocytic choriomeningitis virus (LCMV) or in the treatment of HIV infection/AIDS. Additionally, the human antibodies, antibody compositions and methods of the present disclosure can be used to inhibit TNF-a production.

In certain embodiments, a CD27L antigen binding protein of the invention is used to diagnose, detect, or treat a cancer or tumorigenic disorder. Tumors and cancers amenable for treatment herein, wherein the cells of the tumor or cancer may express CD27L include, but are not limited to: renal cell carcinomas (RCC), such as clear cell RCC, papillary RCC, chromophobe RCC, and the like, glioblastoma, Head and Neck Cancers (e.g., squamous cell carcinomas(HNSCC), and the like), breast cancer, brain tumors, nasopharangeal carcinomas, non-Hodgkin's lymphoma (NHL), such as low grade NHL, diffuse large cell NHL, and the like, acute lymphocytic leukemia (ALL), such as pre-B-ALL, and the like, chronic lymphocytic leukemia (CLL or B-CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas. Additional tumor types amenable for treatment herein, include tumors of the: kidney, pancreas, larynx or pharynx, melanoma, ovary, lung adenocarcinoma, colon breast, brain, and the like.

EXAMPLES

The following examples, both actual and prophetic, are provided for the purpose of illustrating specific embodiments or features of the present invention and are intended to limit its scope.

Example 1

Fully Human Monoclonal Antibodies Against CD27L

The generation of fully human antibodies directed against human CD27L was carried out using XENOMOUSE® technology (U.S. Pat. Nos. 6,114,598; 6,162,963; 6,833,268; 7,049,426; 7,064,244, which are incorporated herein by reference in their entirety; Green et al., 1994, *Nature Genetics* 7:13-21; Mendez et al., 1997, *Nature Genetics* 15:146-156; Green and Jakobovitis, 1998, *J. Ex. Med.* 188:483-495).

IgG1, IgG2, and IgG4 XENOMOUSE® mice were immunized/boosted with soluble human CD27L or human CD27L recombinantly expressed on the surface of Chinese Hamster Ovary (CHO) cells. Hybridomas were produced from the immunized mice. Hybridoma supernatants were screened for binding to recombinant human CD27L-expressing 293 cells. Over 260 supernatants were positive for binding.

The positive supernatants were then screened for binding to native CD27L on the surface of Raji and/or 786-0 cells. The native CD27L binding assay revealed 161 positive supernatants.

Those supernatants were tested for cross-reactivity with cynomolgus CD27L. Twenty-five supernatants were positive for cross-reactivity with cynomolgus monkey CD27L. Those twenty five were then tested for CDC activity and the ability to block human CD27 binding to human CD27L. Nineteen supernatants were positive for CDC activity and for inhibition of CD27 binding to CD27L. Subcloning and sequencing of the 13 IgG1 and 6 IgG4 lines revealed 7 unique IgG1 antibodies (Ab 1-Ab7) and 1 unique IgG4 antibody (Ab8).

A summary of the characteristics of the eight antibodies along with those of a chimeric version of a commercially available mouse anti-human CD27L antibody are provided in FIG. 1.

Affinity

Affinity for recombinant soluble human CD27L was determined using a CM5 chip on a BIACORE 3000. Goat anti-human IgG antibody was used to capture the test antibody. Binding and dissociation of Histidine-tagged human soluble CD27L was measured to determine $K_a$, $K_a$, and $K_D$. The conditions were as follows:

Temperature=25° C.
Flow Rate=50 ul/min
Running Buffer=HBS-EP
Regenerations with 10 mM Glycine pH 1.5
Concentration range of Hu CD27L-his were 200 nM→0.217 nM
Model Fit (Scrubber2): 1:1 Binding+local Rmax
5 Minute Association and 25 Minute Dissociation ADCC Activity The ADCC assay was performed in a sterile 96 well round bottom tissue culture plate (Corning). Antibodies were titrated from 20 μg/mL to 0.0002 μg/mL by carrying 10 μL in 100 μL of complete RPMI containing 10% FCS (a 1:10 dilution). Calcein-labeled targets were added, 50 μL to contain 10,000 cells. Target cells and various concentrations of antibody were incubated for 40 minutes at 4° C., then NK cell effectors added, 50 μL to contain 200,000 cells. Cultures were incubated for 4 hrs at 37° C. then supernatants pulled and assayed for calcein release by measuring fluorescence at 485-535 nm on a Wallac Victor II 1420 Multilable HTS counter. 100% lysis values were determined by lysing six wells of calcein labeled Raji targets with Igepal 630 detergent (3 μL per well) and spontaneous lysis values determined by measuring the fluorescence in supernatants from targets alone.

Percent (%) specific lysis was defined as (sample fluorescence)−(spontaneous lysis fluorescence)/(100% lysis−spontaneous lysis fluorescence). Raw data was entered in an Excel spreadsheet with the embedded formulae to calculate % specific lysis and resultant values transferred to graphic program (GraphPad Prism) where the data was transformed in a sigmoidal curve fit graph. Subsequent analyses (linear regression calculations) were done in GraphPad to generate $EC_{50}$ values.

ADCP Activity

Monocytes were negative selected from human peripheral blood and stored in 4° C. cold room over night with medium RPMI 1640 containing 10% FBS. Then monocytes were seeded to a 48-well tissue culture plate at 200,000 cells per well with 200 μL of growth medium (RPMI 1640 containing 10% FBS and 40 ng/ml Hu M-CSF) and incubated at 37° C., 5% $CO_2$ for 6 days to let monocytes differentiate to macrophages.

On Day 6, the ADCP assay was performed as follows:
1. Labeling target cells with PKH67 green dye at final concentrations of $2\times10^{-6}$ M PKH67 dye Tumor cells were collected and washed once with PBS by centrifuging the cells (400' g) for 5 minutes.
  After centrifuging cells, the supernatant was carefully aspirated, but leaving no more than 25 mL of supernatant.
  Four μL of the PKH67 ethanolic dye solution at stock concentration of $4\times10^{-6}$ M was added to 1 ml of Diluent C from kit in polypropylene tube and mixed well.
  Cell pellets were re-suspended into 1 mL of Diluent C at a density of $20\times10^6$ in polypropylene tube.
  Cells were rapidly transferred to dye work solution with gently pipetting to insure complete dispersion.
  The mixture was incubated at room temperature for 4 minutes with mixing periodically.
  Two mL of whole activated FBS was added into cells to stop the staining and incubated at room temp for 1 minute to allow binding of excess dye.
  Forty mL of RPMI containing 10% FBS was added into cells and washed once by centrifuging the cells (400' g) for 10 minutes.
  Cell pellets were suspended with 40 mL of medium again and transferred to a new tube.
  Cells were washed again three times with medium RPMI+10% FBS and 1× with complete growth medium (RPMI 1640 containing 10% FBS and 40 ng/ml Hu M-CSF).
  Cells were counted and suspended with growth medium at $1\times10^6$ cells per mL for T:E at 1:2 ratio.

2. Treatment of tumor cells with antibodies for antibody dependent cellular phagocytosis (ADCP)

Antibody dilutions were prepared in macrophage growth medium. These dilutions were concentrated at four times higher than final concentrations.
  To preincubate PKH67 green labeled target cells with antibodies, 280 ul of 4× concentrated antibodies was mixed with 280 ul of green labeled tumor cells and incubated at 4° C. for 30 minutes.
  The mixture of green labeled tumor cells with anti-tumor antibodies was added to macrophage cells in 48-well plate at 200 μl for each well as indicated in the Experiment Design table below. The final volume is 0.4 ml per well. The ratio of target cells to effect cells (macrophages) is 1:2.
  Cells were incubated at 37° C., 5% $CO_2$ for one hour.

3. Counterstaining macrophages with macrophages marker

Target cells and macrophages in 48-well plate were detached with Trypsin-Versene mixture.
  Cells were transferred into a 96-well block with 2.2-ml volume per well and washed once with pre-warmed FASC wash solution by spinning the blocks at 400' g for 5 minutes and then discarding supernatant.

Macrophages were stained with their marker, CD11b-Biotin at 1:200 dilution in block solution with 100 μl per well for 10 min on ice.

After washing cells once, macrophages were detected with streptavidin Alexa 568 at 1:1000 dilutions for 10 minute on ice.

After washing cells 1× with PBS, cells were fixed with 4% formaldehyde-PBS at room temperature for 20 minutes. Then cells were washed 1× with dH2O.

Cell pellets were resuspended with water at 200 μl per well and transferred to a 96-well plate at 100 μl per well.

4. Quantitative measurement of phagocytosis activity on an ArrayScan $V^{TI}$ HCS reader (version 6, Cellomics Inc. Thermo Fisher Scientific, Pittsburgh, Pa.) with Target Activation Bio-Application employing a 20× objective. The filter setting was indicated in Table 2. At least 200 cells were counted in each well.

TABLE 2

| Channel | Target | Label | Fluor |
|---|---|---|---|
| 1 | macrophages | Ms-anti-Hu CD11b Biotin→streptavidin Alexa 568 | red |
| 2 | Tumor cells | PHK67 | green |

Statistical analysis was performed using Prism 4.01 (GraphPad, San Diego, Calif.). A plot shows % tumor cell phagocytosis vs. the log of antibody concentration in ng/ml. The percentage of tumor cell phagocytosis is represented with percentage of tumor cells that were overlapped with macrophages vs. total macrophages in the selected fields and obtained from output feature of ArrayScan reader "% Object-Counts". The % values were expressed as the mean+/−standard error of the mean (SEM) for duplicate measurements (n=2). The $EC_{50}$ was determined by using nonlinear regression (curve fit) followed by using Sigmoidal dose-response equation. Data were normalized to the maximum and minimum signal and fit to a sigmoidal dose-response curve.

CDC Activity

Preparation of tumor cells: Raji cells were washed once with assay medium and resuspended in assay medium (RPMI 1640 plus 1% FBS). Cells were seeded in a 96-well tissue culture plate at 50 μL per well with two cell densities for both rabbit and human complement complements. For rabbit complement, the cell density was $5 \times 10^4$ cells per well. For human complement, the cell density was $2 \times 10^5$ cellsper well.

Treatment of cells with complement and test antibody: Three times concentrated complements were prepared in assay medium as outlined in Table 3. Then they were added to cells in plates at 50 μL per well. For cells treated with rabbit complement, the final concentration of rabbit complement was 10%; for cells treated with human complement, the final concentration of human complement was 20%.

TABLE 3

Preparation of 3× concentrated complement
in assay medium (RPMI 1640 + 1% FBS)

| 3× Complement | Complement (ml) | Assay Medium (ml) | Total Volume (ml) |
|---|---|---|---|
| 30% HI rabbit C' (inactive) | 0.5 | 1.16 | 1.66 |
| 30% no HI rabbit C' (active) | 2.5 | 5.83 | 8.33 |
| 60% HI Hu C' (inactive) | 0.5 | 0.33 | 0.83 |
| 60% no HI Hu C' (active) | 3 | 2.0 | 5.0 |

Test antibodies at 10 μg/mL were added to cells at 50 μL per well. The total volume in each well at the start of culture was 150 μL. Cells were continuously incubated at 37° C., 5% $CO_2$ for one hour for cells treated with rabbit complement and 6 hours for cells treated with human complement.

Measurement of cytotoxicity with ArrayScan plate reader: After incubation, 50 μl medium from each well was removed. The cocktail of Hoechst 33342 and propidium iodide (PI) which was prepared at 1:1000 dilution in PBS solution containing 2% FBS was added into cells at 100 μL per well. Cells treated with human complement were transferred into a new 96-well plate at 40 μL per well after gently mixing. Samples were analyzed on an ArrayScan $V^{TI}$ HCS reader (version 6, Cellomics, Thermo Fisher Scientific, Pittsburgh, Pa.) with BioApplication "Target Activation" employing a 20× objective. The filter setting was indicated in Table 4. At least 200 cells were counted in each well.

TABLE 4

| Channel | Target | Label | Fluor | Filter |
|---|---|---|---|---|
| 1 | Nucleic acid for all cells | Hoechst 33342 | UV/460 | nm DAPI |
| 2 | Nucleic acid for dead cells | Propidium iodide | 488/>575 | nm TRITC |

Statistical Analysis: Statistical analysis was performed using Prism 4.01 (GraphPad, San Diego, Calif.).

Internalization Time

Seeding cells: 786-0 cells were seeded on a 96-well plate at 10,000 cells per well with 100 μL of growth medium (RPMI containing 10% FBS) and incubated at 37° C., 5% $CO_2$ for 2 days to reach to 100% cell confluency on assay day. Plated cells were evaluated for 1) internalization and 2) endosomal co-localization.

Staining cells for internalization time-course: Plate was washed 1× with assay medium (PBS containing 2% FBS). Antibodies were added to wells at 2 μg/mL per well (100 μL, per well) in assay medium. Human antibodies were allowed to bind to cells at 4° C. for 30 minutes and then washed 1× with assay medium. Anti-human IgG Fab' Alexa 488 (1:100) and Hoechst 33342 (1:2000) were added to cells in assay medium at 4° C. for 20 minutes. Next cells were washed 1× with assay medium. Cells were either fixed and permeabilized, starting with time zero or incubated at 37° C., 5% $CO_2$ for 1, 3, or 5 hours. Post incubation, cells were fixed and permeabilized with the following procedure. Cells were washed 1× with BD wash buffer, followed by addition of Fix/perm solution to wells at 100 μL per well. Samples were analyzed on an ArrayScan $V^{TI}$ HCS reader (version 6, Cellomics, Thermo Fisher Scientific, Pittsburgh, Pa.) with BioApplication "Spot Detector" employing a 40× objective. The filter setting for internalization was indicated in Table 5. At least 400 cells were counted in each well.

TABLE 5

| Channel | Target | Label | Filter |
|---|---|---|---|
| 1 | Nucleic acid for all cells | Hoechst 33342 | DAPI (blue) |
| 2 | Internalized spots | Alexa 488 | FITC (green) |

Count-staining cells for co-localizing internalized spots to the early endosomal compartment: After internalization analysis, 786-0 cells were washed 1× with BD buffer. Cells were explored to Fix/perm solution at RT for 20 minutes.

Following 2× wash steps, cells were incubated with EEA-1 in BD buffer at 0.5 μg/mL (100 μl/well) at RT for 20 minutes. Cells were washed 1× with BD buffer and added with anti-mouse Alexa 568 at 1:1000 dilution. Cells were incubated at RT for 20 minutes followed by two wash steps of BD buffer solution.

Photographing images: Cell images for internalization and co-localization were taken with a Leica florescent microscope connected to Hamamutsu digital camera with Openlab Image Analysis software (Improvision Inc, Lexington, Mass.) or ArrayScan $V^{TT}$ HCS reader.

Statistical Analysis: Statistical analysis was performed using Prism 4.01 (GraphPad, San Diego, Calif.). The spot counts were expressed as the mean±standard error of the mean (SEM) for duplicate measurements (n=2). Using analysis tool, spot count per unit time (internalization rate) was fit to a one phase exponential association equation.

Example 2

Assessment of MCC-DM1-Conjugated Antibodies

Figure 12:
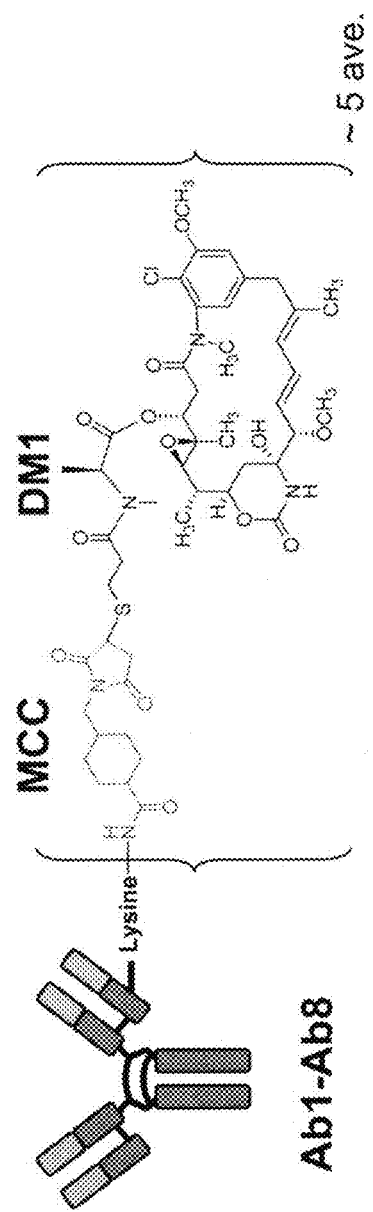
FIG. 12. Sets forth the structure of the Ab-MCC-DM1 ADCs described in Example 2 herein.

Ab1, Ab2, Ab4, Ab7, and Ab8 were conjugated to MCC-DM1 (see FIG. 12). The targeted load level was 4.5-5 drugs per antibody. Briefly, the lysines of the antibody were conjugated to the NHS-ester of the hetero-bifunctional cross-linker Succinimidyl 4-[N-maleimidomethyl]cyclohexane-1-carboxylate (SMCC) which contains an NHS-ester and a maleimide. Next the linker-modified antibody was purified from excess linker and then conjugated to the warhead DM1 via a sulfhydryl present on DM1. Excess DM1 was then removed by a second purification step to generate the final conjugate Ab-MCC-DM1.

More particularly, CD27L antibody, transiently expressed in mammalian cell culture 2936-E cells, was loaded onto a MabSelect SuRe column (GE Healthcare) that had been equilibrated in 25 mM Tris, 150 mM Sodium Chloride, pH 7.4. The column with bound CD27L antibody was then washed with 3 wash steps: first an equilibration buffer wash, followed by a 25 mM Tris, 500 mM L-Arginine, pH 7.5 wash and a final wash with equilibration buffer. CD27L antibody was eluted with 100 mM Sodium Acetate, pH 3.5. Fractions containing the antibody were pooled and adjusted to a final pH of 5.0 with 1M Tris, pH 8.0. The antibody was subsequently purified on a Fractogel® EMD $SO_3$-(M) column (EMD Chemicals Inc) equilibrated in 30 mM Sodium Acetate, pH 5.0. Bound antibody was eluted with an 8CV gradient between 0 to 0.8M Sodium Chloride in 30 mM Sodium Acetate, pH 5.0. Antibody containing fractions were pooled and dialyzed into Conjugation Buffer (2 mM EDTA, 50 mM Sodium Chloride, 50 mM Potassium Phosphate, pH 6.5).

The purified CD27L antibody was modified with the amine reactive linker Succinimidyl-4-(N-maleimidomethyl)cyclohexane-1-carboxylate (SMCC) (Thermo Scientific) to introduce thiol reactive maleimide groups. The antibody at a concentration of 55 μM was treated with 20 molar equivalents of SMCC in Conjugation Buffer adjusted to 10% dimethylacetamide (v/v) in the final reaction mixture. After incubation for 90 minutes at room temperature, the reaction mixture was desalted with a HiPrep 26/10 Desalting Column containing Sephadex G-25 fine resin (GE Healthcare) equilibrated in 2 mM EDTA, 150 mM Sodium Chloride, 35 mM Sodium Citrate, pH 5.0. Antibody containing fractions were pooled and assayed for degree of modification with linker using Ellman's reagent (5,5'-dithio-bis-[2-nitrobenzoic acid]) as described below. The antibody was found to be modified with an average of 7.5 maleimide groups per antibody.

Ellman's reagent is cleaved by thiols, yielding a yellow product with an absorbance at 412 nm. A subtractive Ellman's assay was used to determine the number of maleimide groups on the CD27L antibody after reaction with SMCC. CD27L antibody modified with SMCC or a control sample of buffer without antibody was incubated with an equivalent concentration of thiols, 0.4 mM DTT (dithiothreitol). Any maleimides present in the antibody sample would react with the thiols in DTT, making it unavailable for further reaction with Ellman's reagent. Ellman's reagent was then added to both samples and a colorimetric quantitation at 412 nm was made to determine the concentration of reacted Ellman's reagent. The decreased concentration of thiols in the antibody sample as compared to the control sample is proportional to the number of maleimides present in the antibody sample. This value was used to determine the number of linked maleimide groups per modified CD27L antibody.

The SMCC modified CD27L antibody (7.5 maleimide groups per antibody) at a concentration between 17 μM -27 μM was treated with 1.7 molar equivalents of DM1 (Immunogen) per maleimide group buffered with 2 mM EDTA, 150 mM NaCl, 35 mM Sodium Citrate, pH 5.0 adjusted to 3% DMA (v/v) in the final reaction mixture. Reaction mixtures were incubated at room temperature overnight for up to 20 hours. The reaction mixture was loaded on a Superdex 200 gel filtration column (GE Healthcare) equilibrated with 20 mM Sodium Phosphate, 150 mM Sodium Chloride, pH 6.5. Fractions were collected and monomeric antibody containing fractions pooled and assayed. The molar ratio of DM1 molecules linked per antibody was determined by measuring the absorbance at 252 nm and 280 nm, and found to be 4.5-5.0 DM1 molecules per antibody.

In Vitro Pharmacology

The antibody drug conjugates (ADC) Ab4- and Ab8-MCC-DM1 demonstrated comparable native CD27L binding to their un-conjugated counterparts as assessed by flow cytometry. The observed binding EC50 for Ab4 and Ab4-MCC-DM1 were the same while it was a modest 4-fold lower for Ab8-MCC-DM1 as compared to Ab8 (Table 6). A more precise measure of binding affinity was determined for Ab4, Ab8 and their conjugate counterparts by measuring their ability to bind native human CD27L expressed on Raji cells using Gyros technology. The results showed that both conjugates exhibited sub-nM affinities for CD27L within two-fold of those observed for the un-conjugated Ab4 and Ab8 (Table 6). Both unconjugated and conjugated Ab4 and Ab8 also exhibited binding affinities to soluble human CD27L-his within 2-fold of each other as determined by BIACORE.

TABLE 6

Binding comparison of Ab4 and Ab8 to their MCC-DM1 conjugate counterparts

| Measurement | Ab4 | Ab4-MCC-DM1 | Ab8 | Ab8-MCC-DM1 |
|---|---|---|---|---|
| Gyros $K_D$-native CD27L-Raji | 0.014 nM | 0.023 nM | 0.078 nM | 0.077 nM |
| FACS ($EC_{50}$)-786-0 | 0.1 nM | 0.1 nM | 0.02 nM | 0.08 nM |

The internalization of Ab4-MCC-DM1, Ab8-MCC-DM1, Ab4, and Ab8 was evaluated in the CD27L-expressing human ccRCC line 786-0. CD27L expressing 786-0 cells were exposed to un-conjugated Ab4 and Ab8 human anti-CD27L antibody, Ab4-MCC-DM1, Ab8-MCC-DM1, control HuIgG1, or control αSA-MCC-DM1 and allowed to bind at 4° C. Internalization of the test articles was evaluated using FluoroNanogold goat anti-hu IgG Fab' Alexa 488. Cells were fixed and permeabilized at specific times after incubation with test articles (time=0, 1, 3, and 5 hour) and imaged using an ArrayScan VTI HCS reader. Co-localization of internalized test articles to endosomes was determined using anti-EEA-1 antibody, an endosomal marker. The time-dependent internalization of the antibodies, including Ab4-MCC-DM1, was observed via fluorescence microscopy image analysis by the formation of punctate spots within the cellular cytoplasm at 37° C. compared with cell membrane localization at time zero at 4° C. Ab4-MCC-DM1 co-localized with the endosomal marker EEA-1 after a 5-hour incubation at 37° C., demonstrating that Ab4-MCC-DM1 is internalized into the endosomal subcellular compartment of 786-0 cells. The level and rate of internalization was within a similar range for Ab4, Ab8 and their conjugated counter-parts (FIG. 2).

Both Ab4-MCC-DM1 and Ab8-MCC-DM1 demonstrated potent and specific in vitro growth inhibition of CD27L-expressing tumor cells. In an anti-proliferation (tumor growth inhibition) assay, Ab4-MCC-DM1, Ab8-MCC-DM1 or unconjugated anti-CD27L Ab4 or Ab8 were incubated with CD27L expressing 786-0 luciferase or CD27L negative H1650 target cells in the presence/absence of naked Ab4 or Ab8, respectively, or control HuIgG1 for 4 days. Both cell lines, 786-0 luciferase and H1650, were seeded in 96-well tissue culture plates with growth medium at 100 μL of well with 500 cells per well for 786-0 luciferase and 1000 cells per well for H1650. All plates were incubated at 37° C., 5% $CO_2$ for 4 hours. After a 4 hour incubation, naked Ab and conjugates were added to cells at 100 μL per well at various dose titrations. The total volume in each well at the start of culture was 200 μL. Cells were continuously incubated at 37° C., 5% $CO_2$ for 4 days prior to measurement of cellular ATP levels. To assess cell growth inhibition, ATP levels (as a measure of cell number) were measured via luminescence using the Cell-Titer-Glo assay kit.

Figure 3:
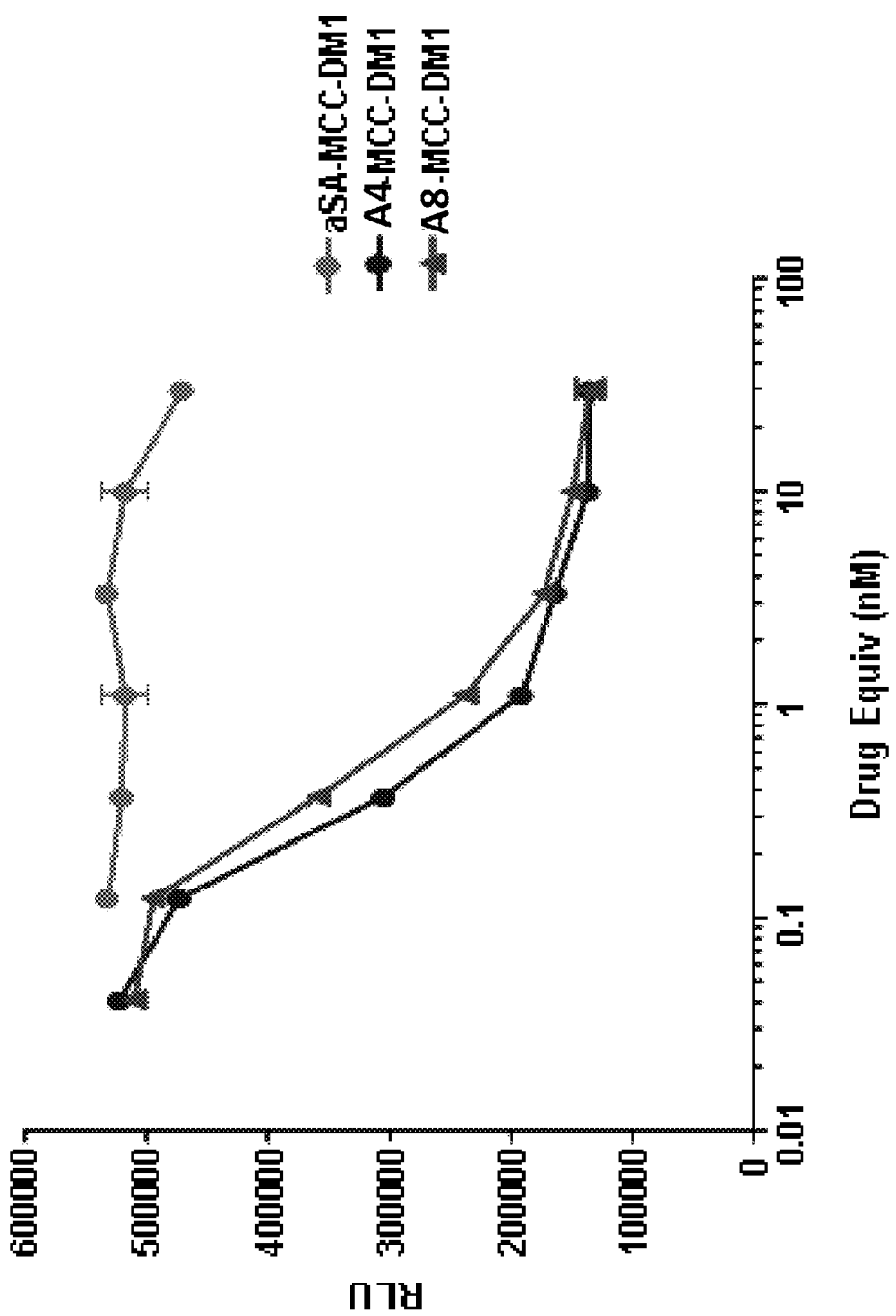
FIG. 3. 786-0 cells were cultured for 4 days in the presence of increasing concentrations of anti streptavidin-MCC-DM1, Ab4-MCC-DM1 and Ab8-MCC-DM1. Effect on cell growth was measured using the CELL-TITER-GLO reagent that measures cell number using a luminescent read-out.

Both Ab4-MCC-DM1 and Ab8-MCC-DM1 inhibited cell growth of CD27L-expressing 786-0 cells with a concentration of 50% inhibition ($IC_{50}$) as set forth in Table 7. Cell growth inhibition was not observed in CD27L-negative H1650 cells upon exposure to Ab4-MCC-DM1 and Ab8-MCC-DM1. Addition of an excess of unconjugated parental anti-CD27L antibody was able to block Ab4-MCC-DM1 mediated growth inhibition, confirming CD27L binding by Ab4-MCC-DM1 was required for activity. Unconjugated parental anti-CD27L antibody did not inhibit the growth of CD27L-expressing 786-0 cells. Control conjugate, anti-streptavidin-MCC-DM1 (αSA-MCC-DM1), did not exhibit any inhibition of cell growth in either the CD27L-positive or the CD27L-negative cell line. The results indicate that both Ab4-MCC-DM1 and Ab8-MCC-DM1 were potent inhibitors of 786-0 cell growth compared to control conjugate (FIG. 3). Ab4-MCC-DM1 tended to show a slight increase in potency over Ab8-MCC-DM1 (Table 7).

TABLE 7

Cellular Potency of anti CD27L-MCC-DM1 conjugates

| 786-0-$_{IC50}$ | Ab4-MCC-DM1 | Ab8-MCC-DM1 |
|---|---|---|
| Drug Conc. (nM) | 0.34 | 0.54 |
| Antibody Conc. (nM) | 0.07 | 0.11 |

Figure 8:
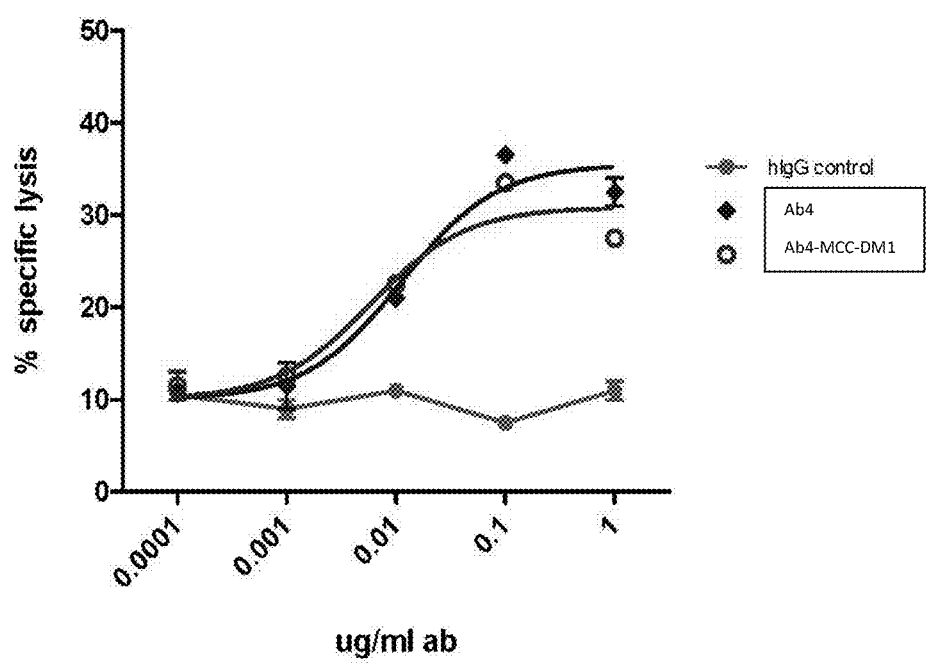
FIG. 8. Ab4-MCC-DM1 Antibody Dependent Cell Cytotoxicity (ADCC) Assay against Raji tumor cells.
Figure 9:
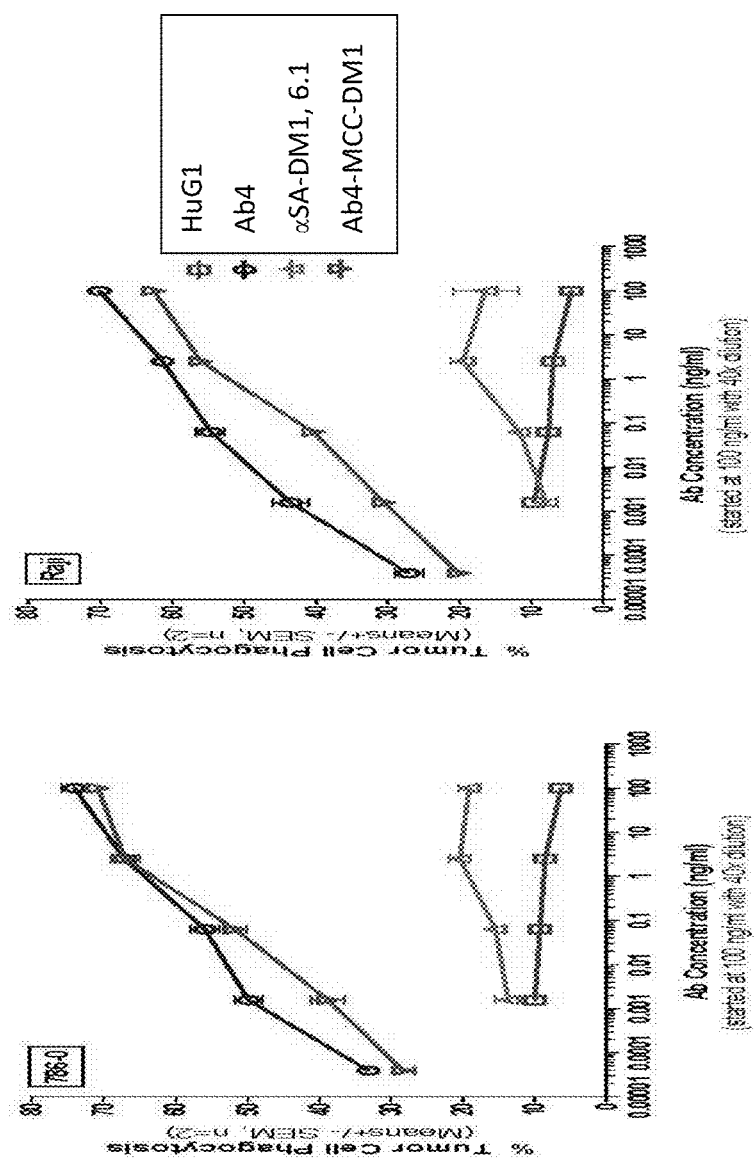
FIG. 9. Ab4-MCC-DM1 Antibody Dependent Cellular Phagocytosis (ADCP) Assay against both Raji and 786-0 tumor cells.
Figure 10:
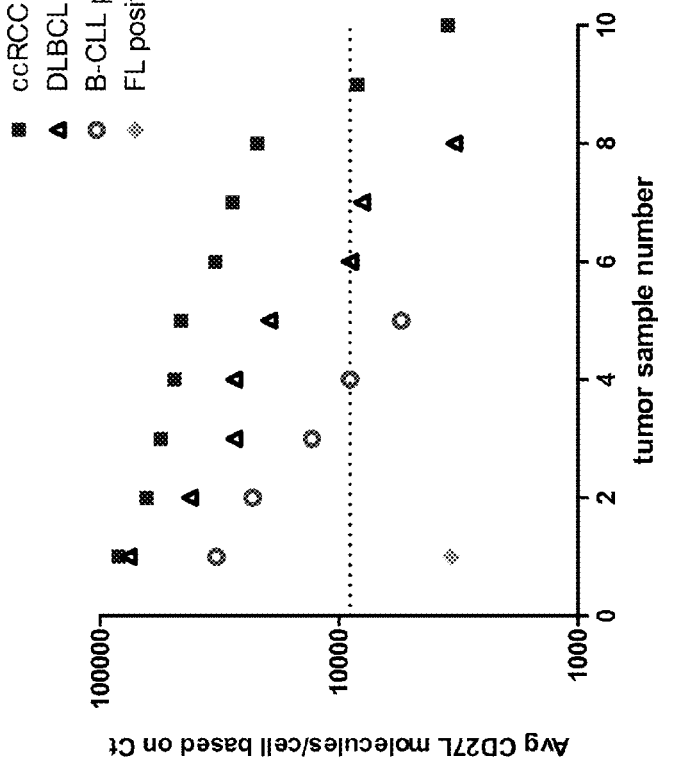
FIG. 10. Comparison of CD27L expression for primary frozen tumor samples that scored "positive" by masked IHC. The results indicate that overall CD27L protein expression is highest in ccRCC patient samples, followed by DLBCL (Diffuse Large B-Cell Lymphoma); B-CLL and FL samples.

Ab4-MCC-DM1 mediated Antibody Dependent Cell Cytotoxicity (ADCC) against Raji cells with similar potency (EC50=0.006 μg/mL) and magnitude to that observed for the unconjugated parental Ab4 anti-CD27L antibody (EC50=0.01 μg/mL). Briefly, Natural Killer (NK) cells isolated from the PBMC obtained from a normal human blood donor were incubated with calcein labeled Raji human B cell lymphoma target cells (express CD27L) in the presence of Ab4-MCC-DM1 or control antibodies as described above. Percent (%) specific cytotoxicity was determined by measuring calcein release from CD27L expressing target cells lysed in the presence of Ab4-MCC-DM1 as compared to control wells. The results are shown in FIG. 8 which indicate that Ab4-MCC-DM1 mediated a similar level of ADCC to that of the Ab4 antibody (EC 50 values of 0.006 and 0.01 μg/mL respectively). The huIgG1 control did not mediate any measurable lysis of CD27L expressing targets. Both the Ab4-MCC-DM1 and the unconjugated Ab4 antibody are capable of inducing NK cell mediated ADCC of CD27L specific targets at similar levels. Similar results were observed for Ab8-MCC-DM1 and the unconjugated Ab8 antibody.

vitro Antibody Dependent Cellular Phagocytosis (ADCP) activity of Ab4-MCC-DM1 or unconjugated parental antibody Ab4 was measured against both Raji and 786-0 tumor cells. Ab4-MCC-DM1 mediated a similar level of complement-mediated lysis to that observed for unconjugated parental antibody Ab4. Briefly, macrophages were differentiated from monocytes isolated from the human peripheral blood obtained from normal human blood donors. Macrophages were incubated with PHK67 green labeled CD27L expressing cell lines, 786-0 and Raji as target cells in the presence of unconjugated anti CD27L antibody Ab4, HuIgG1, Ab4-MCC-DM1, or control antibodies (αSA-MCC-DM1), as described above. Percent (%) tumor cell phagocytosis was determined from the percentage of tumor cells that were engulfed by macrophages vs. total macrophages in the selected fields. The results are shown in FIG. 9 and indicate that Ab4-MCC-DM1 mediated similar ADCP potency in CD27L expressing cell lines, 786-0 and Raji. EC50 values of the unconjugated Ab4 were within 10-fold of those observed for Ab4-MCC-DM1 (see Table 8).

TABLE 8

| Abs | 786-0 EC50 (pM) | Raji EC50 (pM) |
|---|---|---|
| Ab4 | 0.008 | 0.008 |
| Ab4-MCC-DM1 | 0.087 | 1.421 |

Given that the dilution curve was performed at 1:40 dilution intervals, the observed EC50 for both Ab4-MCC-DM1 and the unconjugated Ab4 are of a similar potency (with-in the margin of the dilution factor). Thus, both the conjugated Ab4-MCC-DM1 and the unconjugated WT Ab4 antibodies are capable of inducing human macrophage to mediate ADCP of CD27Lexpressing cells at similar levels. Similar results were observed for Ab8-MCC-DM1 and the unconjugated Ab8 antibody.

In vitro Complement Dependent Cytotoxicity (CDC) activity of Ab4-MCC-DM1 was assessed employing both human and rabbit complement and CD27L-expressing Raji tumor cells. At 10 μg/mL, Ab4-MCC-DM1 mediated a similar level of complement-mediated lysis to that observed for unconjugated parental antibody Ab4 (rabbit complement 72% lysis and human 17% lysis). Briefly, activated rabbit or human complements were incubated with CD27L expressing Raji target cells in the presence of anti CD27L antibodies or control antibodies, as described above. CDC mediated killing was measured from output feature of ArrayScan reader "% selected objects" to detect % of PI positive vs. Hoechst for "% Cytotoxicity." The results indicate that Ab4-MCC-DM1 mediated similar levels of CDC to that of the WT Ab4 antibody when incubating tumor Raji cells with 10% baby rabbit complement or 20% human complement. Heat inactivated rabbit or human complements didn't show any CDC mediated killing against Raji. Thus, both Ab4-MCC-DM1 and un-conjugated Ab4 induce a similar level of CDC activity against CD27L expressing tumor target cells. Similar results were observed for Ab8-MCC-DM1 and the unconjugated Ab8 antibody.

In Vivo Pharmacology

Figure 4:
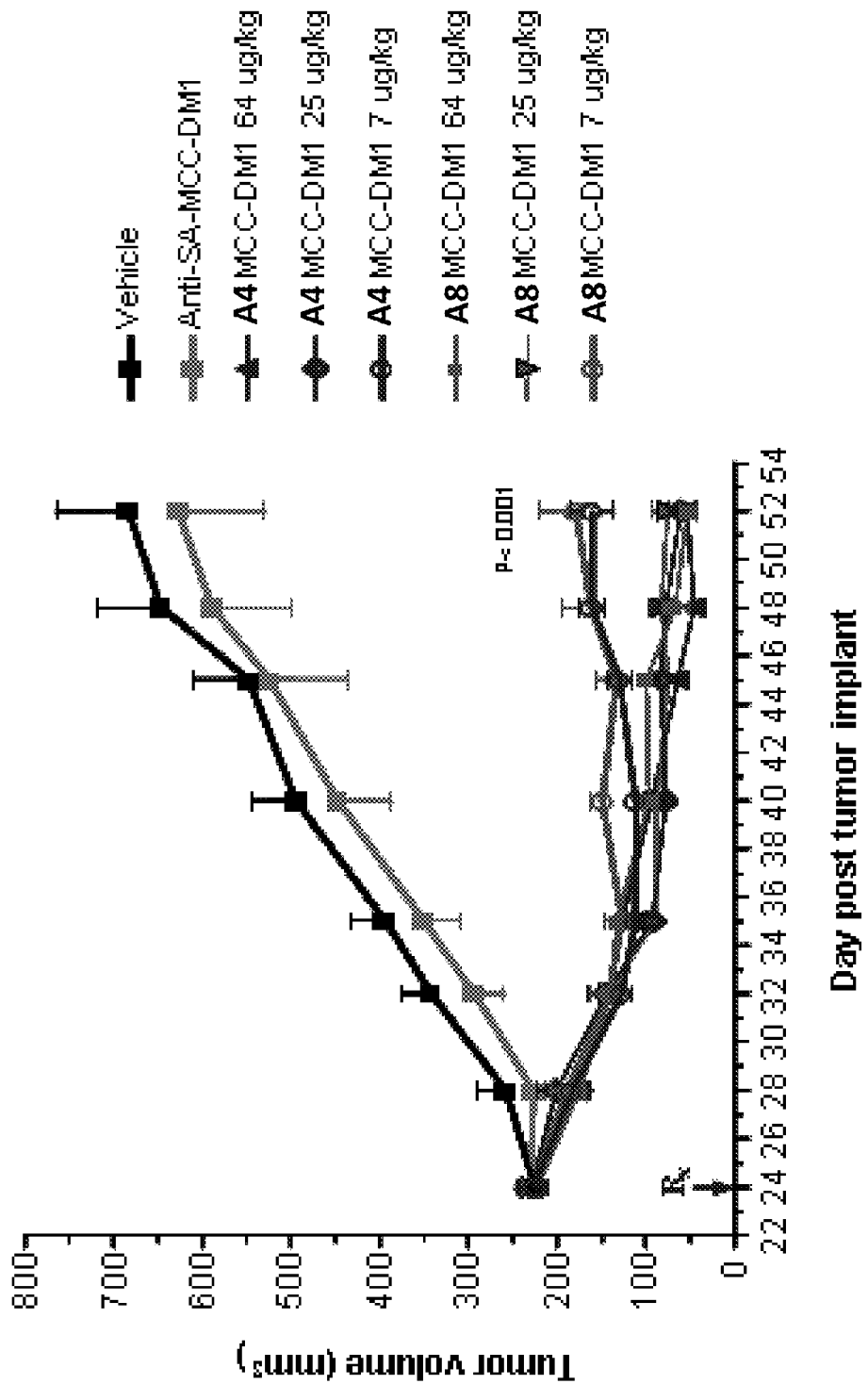
FIG. 4. Dose response of Ab4-MCC-DM1 and Ab8-MCC-DM1 in the 786-0 xenograft model. Intravenous dose on day 24 is denoted by arrow at the indicated doses.

In vivo passaged 786-0 ccRCC cells (786-0 S4) were implanted into female CB-17/SCID mice using growth-factor reduced MATRIGEL to generate tumor xenografts for efficacy studies. 786-0 S4 cells express an average of approximately 180,000 CD27L sites/cell. Treatment with Ab4-MCC-DM1 or Ab8-MCC-DM1 was initiated when the tumor size reached an average of approximately 250 $mm^3$. Tumor-bearing animals were randomized by tumor size into groups of ten animals each and dosed intravenously once. A blinded dose response study of Ab4-MCC-DM1 and Ab8-MCC-DM1 employing doses ranging from 7-64 ug DM1/kg (0.3-2.5 mg Ab/kg) was performed in this established tumor model. Robust tumor regression was observed at the low 7 ug DM1/kg, mid 25 ug DM1/kg and the high 64 ug DM1/kg doses. At the mid and high dose, complete regressions were maintained at least 28 days following a single dose (FIG. 4). No body weight loss was observed in any of the dosing groups over the course of the study.

Figure 5:
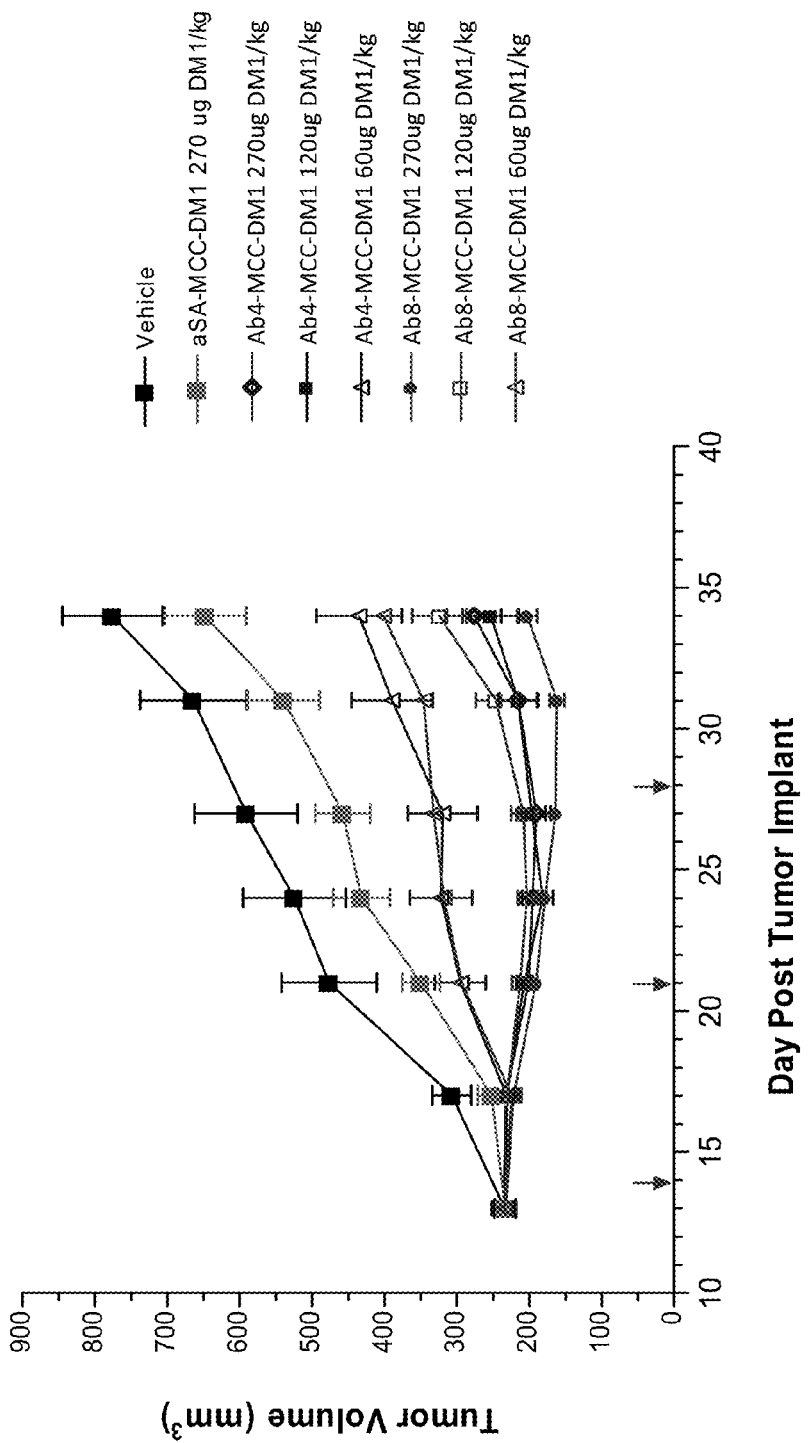
FIG. 5. Dose response of Ab4-MCC-DM1 and Ab8-MCC-DM1 in the Caki-1 xenograft model. Intravenous dosing schedule is denoted by the arrows.

In another demonstration of in vivo efficacy, Caki-1 ccRCC cells that express an average of 59,000 CD27L sites per cell (3-fold less that 786-0 cells) were implanted into CB-17/SCID mice as described above. When the Caki-1 xenografts reached an average size of 250 $mm^3$, tumor-bearing animals were randomized by tumor size into groups of ten animals each and dosed intravenously once per week for 3 weeks (to more closely mimic a weekly clinical dosing regimen). A blinded dose response study of Ab4-MCC-DM1 and Ab8-MCC-DM1 employing doses ranging from 60-270 ug DM1/kg (2.4-11 mg Ab/kg) was performed in this established tumor model. Tumor regression was initially observed at the mid 120 ug DM1/kg and the high 270 ug DM1/kg doses while tumor growth inhibition was observed at the low 60 ug DM1/kg dose compared to the control conjugate or vehicle. As time progressed, tumor regression in the two higher dose groups began to diminish within 7 days of receiving the last dose (FIG. 5).

Figure 6:
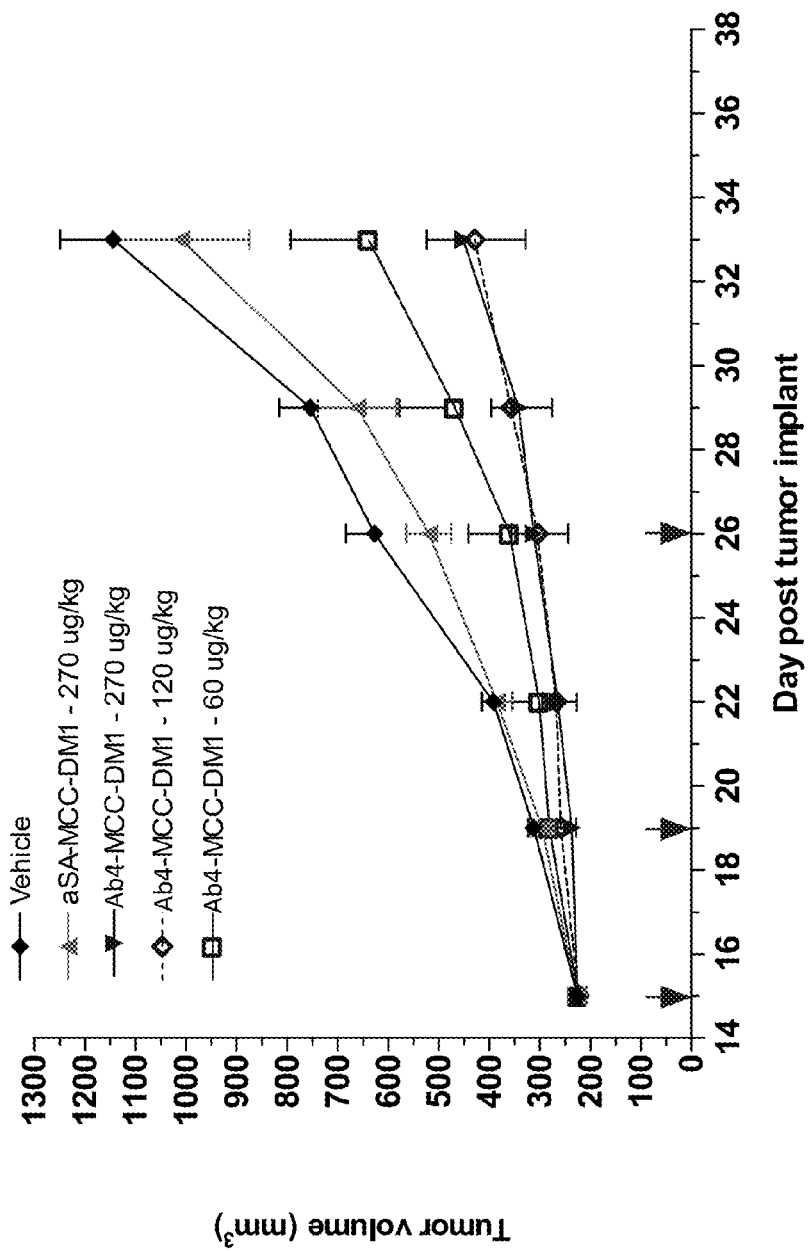
FIG. 6. Dose response of Ab4-MCC-DM1 in the Raji xenograft model. The intravenous dosing schedule is denoted by the arrows.

Like ccRCC cells, Raji B-lymphoma cells express CD27L (about 200,000 sites/cell) and internalize the anti-CD27L drug conjugate which results in mitotic arrest and cell death in vitro. Ab4-MCC-DM1 was evaluated for efficacy in the subcutaneous Raji Xenograft model. When the Raji xenografts reached an average size of 250 $mm^3$, tumor-bearing animals were randomized by tumor size into groups of ten animals each and dosed intravenously q4 days×2 and then once per week for one additional week for a total of 3 doses (to more closely mimic a weekly clinical dosing regimen). A blinded dose response study of Ab4-MCC-DM1 using doses ranging from 60-270 ug DM1/kg (2.4-11 mg Ab/kg) was performed in this established tumor model. Tumor growth inhibition was observed at all dose levels, with >90% tumor growth inhibition being observed at the mid 120 ug DM1/kg and the high 270 ug DM1/Kg doses during the active dosing period with an intermediate anti tumor response being observed at the low 60 ug DM1/kg dose compared to control conjugate (FIG. 6). At the end of the tumor measurement period a slight majority of animals in the mid and high dose groups exhibited tumor regression suggesting that further dose and schedule optimization could improve response.

Figure 7:
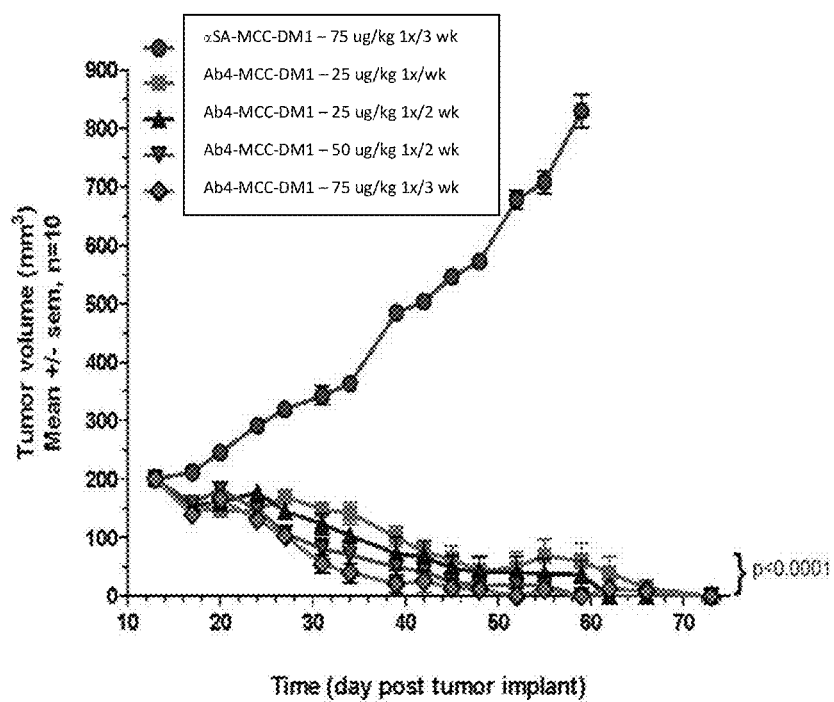
FIG. 7. Variable dose response of Ab4-MCC-DM1 in the 786-0 xenograft model.

The efficacy of different dosing intervals of control conjugate αSA-MCC-DM1, or Ab4-MCC-DM1 was evaluated in the 786-0 xenograft model. CB-17/SCID mice were implanted with 786-0 tumor cells. On day 13, 50 animals were randomized into cohorts of 10 animals each with an average tumor volume of 200 mm3 Each cohort was administered an intraperitoneal dose of either control conjugate αSA-MCC-DM1 or Ab4-MCC-DM1. Tumor volume is represented as group average±standard error of the mean (SEM). Statistical significance of observed differences between growth curves was evaluated from days 13 to 59 by repeated measures analysis of covariance (RMANOVA) of the log transformed tumor volume data with Dunnett adjusted multiple comparisons. Significance is attained if $p<0.05$. Three doselevels of Ab4-MCC-DM1 (1.0, 2.0, or 2.9 mg/kg of Ab4-MCC-DM1 based upon antibody or 25, 50, or 75 pg/kg based upon DM1 equivalents, respectively) were administered. The 1.0 mg/kg dose was administered once per week or once every 2 weeks for 6 weeks, the 2.0 mg/kg dose was administered once every 2 weeks for 6 weeks and the 2.9 mg/kg dose was administered once every 3 weeks for 6 weeks. Animals were dosed intraperitoneally starting on day 13 post tumor inoculation. By day 59, the αSA-MCC-DM1 treated group was euthanized due to large tumor volumes. On day 59, the average tumor volume of mice treated with each dose regimen of Ab4-MCC-DM1 administered was significantly less than that of the αSA-MCC-DM1 control conjugate group ($p<0.0001$) (FIG. 7). Ab4-MCC-DM1 mediated durable tumor regression with each dosing regimen. No body weight loss was observed in any of the Ab4-MCC-DM1 treatment groups.

Pharmokinetics

Ab4 and Ab8 antibody drug conjugates were assessed after intravenous administration to female CB-17/SCID mice containing CD27L-expressing 786-0 xenografts in the context of efficacy studies and a follow-on terminal PK study. The cumulative exposures and clearance values were within 1.33 and 1.4-fold between the Ab4-MCC-DM1 and Ab8-MCC-DM1 molecules, and the half-life of both ADCs was approximately 12 days in mice.

The stability and PK parameters of the Ab4-MCC-DM1 and Ab8-MCC-DM1 antibody drug conjugates were characterized in vivo following a single intravenous (IV) dose into CB-17/SCID mice bearing 786-0 xenografts. The exposures of the two antibody drug conjugates were highly comparable, but Ab4-MCC-DM1 demonstrated a more stable drug-to-antibody conjugation ratio over the 96 hour time-course of the study as determined by affinity-MS than did Ab8-MCC-DM1 molecule. Ab4-MCC-DM1 showed no detectable loss of conjugate integrity at the 30 min or 24 hour time point post injection while Ab8-MCC-DM1 exhibited changes at the 30 minute time point and significant decreases in all conjugate species by 24 hours post injection.

Example 3

Paratope Mapping

Modifications to Ab4 were tested for binding to CD27L by ELISA. CD27L was bound to Maxisorp plates at room temperature for >2 hours, shaking with lug/mL in 100 uL. The plates were then blocked with 250 uL 10% Non-fat dry milk in PBS+0.05% Tween 20 for 2 hours. After a 4×300 uL PBS+0.05% Tween20 (PBST) wash the modified Ab and purified parental control titrations ranging from 0.045 to 100 ng/mL were applied to the plates and incubated for 1 hour. A horseradish peroxidase conjugated αhuFc detection antibody (Jackson) diluted 1:7000 was applied to the plates after another PBST wash, and incubated for 1 hour. A final wash was performed and TMB substrate was incubated for 10 minutes and stopped with phosphoric acid. An OD reading at 450 nm was taken and plotted vs. concentration. These curves were then analyzed with a 3 parameter non linear curve fit and the $EC_{50}$ and Max calculated signal were compared to the purified control. Binding was determined to be similar to parental if the $EC_{50}$ was within 2 fold and the Max signal was greater than 50%. The binding was reduced if the $EC_{50}$ increased greater than 2 fold and/or the max signal was less than 50%. The binding was abolished if no curve could be generated or the max signal was less than 5%.

TABLE 8

Light and heavy chain modifications combinations are listed with their expression levels in ug/mL (determined By ForteBio Protein A quantitation) along with their effect on binding.

| Combinations | Expression | Binding |
|---|---|---|
| N31H-Y58N + N31S-I34M | 30.3 | Reduce |
| N31H-Y58N + G33S-I34L | 46.7 | Abolish |
| N31H-Y58N + D54E-G55S | 9.91 | Abolish |
| N31H-Y58N + S103G-G104S | 14.6 | Abolish |
| N31H-Y58N + Parent HC | 10.4 | Reduce |
| R24K-S26G + N31S-I34M | 13.8 | Similar |
| R24K-S26G + G33S-I34L | 16.9 | Abolish |

TABLE 8-continued

Light and heavy chain modifications combinations are listed with their expression levels in ug/mL (determined By ForteBio Protein A quantitation) along with their effect on binding.

| Combinations | Expression | Binding |
|---|---|---|
| R24K-S26G + D54E-G55S | 1.87 | Reduce |
| R24K-S26G + S103G-G104S | 3.76 | Reduce |
| R24K-S26G + Parent HC | 3.43 | Similar |
| L55I-Y58F + N31S-I34M | 9.53 | Reduce |
| L55I-Y58F + G33S-I34L | 11.6 | Abolish |
| L55I-Y58F + D54E-G55S | 1.26 | Reduce |
| L55I-Y58F + S103G-G104S | 2.61 | Reduce |
| L55I-Y58F + Parent HC | 2.72 | Similar |
| Q95N-T96S + N31S-I34M | 24.6 | Similar |
| Q95N-T96S + G33S-I34L | 32.7 | Abolish |
| Q95N-T96S + D54E-G55S | 1.89 | Reduce |
| Q95N-T96S + S103G-G104S | 4.99 | Abolish |
| Q95N-T96S + Parent HC | 5.85 | Similar |
| Parent LC + N31S-I34M | 31.6 | Reduce |
| Parent LC + G33S-I34L | 51.2 | Abolish |
| Parent LC + D54E-G55S | 7.03 | Reduce |
| Parent LC + S103G-G104S | 10.7 | Abolish |
| Parent LC + Parent HC | 9.25 | Similar |

13 of the 24 modification combinations made to Ab4 retained some level of binding to CD27L. The 9 that did not bind to CD27L had at least one of the following: "G335-134L" and "S103G-G104S" heavy chain modifications or the "N31H-Y58N" light chain modification. Of the 97% similar antibodies (2 amino acid modifications) 75% (6 of 8) retained some level of binding, while 56% (7 of 16) of the 94% similar antibodies (4 amino acid modifications) retain some level of binding, 2 of which have similar binding to the purified parental control. This shows that an antibody as low as 94% similar to Ab4 can still bind CD27L.

What is claimed is:

1. A CD27L antigen binding protein having a light chain variable domain comprising an LCDR1 as set forth in SEQ ID NO:71; an LCDR2 sequence as set forth in SEQ ID NO:79; and an LCDR3 sequence as set forth in SEQ ID NO:87; and a heavy chain variable domain comprising an HCDR1 as set forth in SEQ ID NO:25; an HCDR2 sequence as set forth in SEQ ID NO:33; and an HCDR3 sequence as set forth in SEQ ID NO:41.

2. A CD27L antigen binding protein having a light chain variable domain comprising an LCDR1 as set forth in SEQ ID NO:72; an LCDR2 sequence as set forth in SEQ ID NO:80; and an LCDR3 sequence as set forth in SEQ ID NO:88; and a heavy chain variable domain comprising an HCDR1 as set forth in SEQ ID NO:26; an HCDR2 sequence as set forth in SEQ ID NO:34; and an HCDR3 sequence as set forth in SEQ ID NO:42.

3. A CD27L antigen binding protein having a light chain variable domain comprising an LCDR1 as set forth in SEQ ID NO:73; an LCDR2 sequence as set forth in SEQ ID NO:81; and an LCDR3 sequence as set forth in SEQ ID NO:89; and a heavy chain variable domain comprising an HCDR1 as set forth in SEQ ID NO:27; an HCDR2 sequence as set forth in SEQ ID NO:35; and an HCDR3 sequence as set forth in SEQ ID NO:43.

4. A CD27L antigen binding protein having a light chain variable domain comprising an LCDR1 as set forth in SEQ ID NO:74; an LCDR2 sequence as set forth in SEQ ID NO:82; and an LCDR3 sequence as set forth in SEQ ID NO:90; and a heavy chain variable domain comprising an HCDR1 as set forth in SEQ ID NO:28; an HCDR2 sequence as set forth in SEQ ID NO:36; and an HCDR3 sequence as set forth in SEQ ID NO:44.

5. The A CD27L antigen binding protein having a light chain variable domain comprising an LCDR1 as set forth in SEQ ID NO:75; an LCDR2 sequence as set forth in SEQ ID NO:83; and an LCDR3 sequence as set forth in SEQ ID NO:91; and a heavy chain variable domain comprising an HCDR1 as set forth in SEQ ID NO:29; an HCDR2 sequence as set forth in SEQ ID NO:37; and an HCDR3 sequence as set forth in SEQ ID NO:45.

6. A CD27L antigen binding protein having a light chain variable domain comprising an LCDR1 as set forth in SEQ ID NO:76; an LCDR2 sequence as set forth in SEQ ID NO:84; and an LCDR3 sequence as set forth in SEQ ID NO:92; and a heavy chain variable domain comprising an HCDR1 as set forth in SEQ ID NO:30; an HCDR2 sequence as set forth in SEQ ID NO:38; and an HCDR3 sequence as set forth in SEQ ID NO:46.

7. A CD27L antigen binding protein having a light chain variable domain comprising an LCDR1 as set forth in SEQ ID NO:77; an LCDR2 sequence as set forth in SEQ ID NO:85; and an LCDR3 sequence as set forth in SEQ ID NO:93; and a heavy chain variable domain comprising an HCDR1 as set forth in SEQ ID NO:31; an HCDR2 sequence as set forth in SEQ ID NO:39; and an HCDR3 sequence as set forth in SEQ ID NO:47.

8. A CD27L antigen binding protein having a light chain variable domain comprising an LCDR1 as set forth in SEQ ID NO:78; an LCDR2 sequence as set forth in SEQ ID NO:86; and an LCDR3 sequence as set forth in SEQ ID NO:94; and a heavy chain variable domain comprising an HCDR1 as set forth in SEQ ID NO:32; an HCDR2 sequence as set forth in SEQ ID NO:40; and an HCDR3 sequence as set forth in SEQ ID NO:48.

9. The CD27L antigen binding protein of claim 1, wherein the light chain comprises the amino acid sequence set forth in SEQ ID:56 and the heavy chain comprises the amino acid sequence set forth in SEQ ID NO:10.

10. The CD27L antigen binding protein of claim 2, wherein the light chain comprises the amino acid sequence set forth in SEQ ID:57 and the heavy chain comprises the amino acid sequence set forth in SEQ ID NO:11.

11. The CD27L antigen binding protein of claim 4, wherein the light chain comprises the amino acid sequence set forth in SEQ ID:58 and the heavy chain comprises the amino acid sequence set forth in SEQ ID NO:12.

12. The CD27L antigen binding protein of claim 5, wherein the light chain comprises the amino acid sequence set forth in SEQ ID:59 and the heavy chain comprises the amino acid sequence set forth in SEQ ID NO:13.

13. The CD27L antigen binding protein of claim 6, wherein the light chain comprises the amino acid sequence set forth in SEQ ID:60 and the heavy chain comprises the amino acid sequence set forth in SEQ ID NO:14.

14. The CD27L antigen binding protein of claim 7, wherein the light chain comprises the amino acid sequence set forth in SEQ ID:61 and the heavy chain comprises the amino acid sequence set forth in SEQ ID NO:15.

15. The CD27L antigen binding protein of claim 8, wherein the light chain comprises the amino acid sequence set forth in SEQ ID:62 and the heavy chain comprises the amino acid sequence set forth in SEQ ID NO:16.

16. A variant of the CD27L antigen binding protein of claim 11, wherein the variant is selected from the group consisting of:
   an R24K-S26G light chain modification in SEQ ID NO:58 in combination with an N31S-I34M heavy chain modification in SEQ ID NO:12;
   an R24K-S26G light chain modification in SEQ ID NO:58;
   an L55I-Y58F light chain modification in SEQ ID NO:58;
   an Q95N-T96S light chain modification in SEQ ID NO:58 in combination with an N31S-I34M heavy chain modification in SEQ ID NO:12; and
   an Q95N-T96S light chain modification in SEQ ID NO:58.

17. A variant of the CD27L antigen binding protein of claim 11, wherein the variant is selected from the group consisting of:
   an N31H-Y58N light chain modification in SEQ ID NO:58 in combination with an N31S-I34M heavy chain modification in SEQ ID NO:12;
   an N31H-Y58N light chain modification in SEQ ID NO:58;
   an R24K-S26G light chain modification in SEQ ID NO:58 in combination with an D54E-G55S heavy chain modification in SEQ ID NO:12;
   an R24K-S26G light chain modification in SEQ ID NO:58 in combination with an S103G-G104S heavy chain modification in SEQ ID NO:12;
   an L55I-Y58F light chain modification in SEQ ID NO:58 in combination with an N31S-I34M heavy chain modification in SEQ ID NO:12;
   an L55I-Y58F light chain modification in SEQ ID NO:58 in combination with an D54E-G55S heavy chain modification in SEQ ID NO:12;
   an L55I-Y58F light chain modification in SEQ ID NO:58 in combination with an S103G-G104S heavy chain modification in SEQ ID NO:12;
   an Q95N-T96S light chain modification in SEQ ID NO:58 in combination with an D54E-G55S heavy chain modification in SEQ ID NO:12;
   an N31S-I34M heavy chain modification in SEQ ID NO:12; and an D54E-G55S heavy chain modification in SEQ ID NO:12.

18. The CD27L antigen binding protein of any one of claims 1, 2, 3, 4, 5, 6, 7, 8, 9, 10, 11, 12, 13, 14, 15, 16, or 17, wherein the CD27L antigen binding protein is conjugated to a chemotherapeutic agent.

19. The CD27L antigen binding protein of claim 18, wherein a linker conjugates the chemotherapeutic agent to the CD27L antigen binding protein.

20. The CD27L antigen binding protein of claim 19, wherein the linker is a non-cleavable linker.

21. The CD27L antigen binding protein of claim 20, wherein the linker comprises N-succinimidyl 4-(N-maleimidomethyl) cyclohexane-1 carboxylate (MCC).

22. The CD27L antigen binding protein of claim 21, wherein the chemotherapeutic agent is conjugated to one or more lysines contained within a polypeptide of the CD27L antigen binding protein.

23. The CD27L antigen binding protein of claim 22, wherein the chemotherapeutic agent is $N^{2'}$-deacetyl-$N^{2'}$(3-mercapto-1-oxopropyl)-maytansine (DM1).

24. A composition of CD27L antigen binding proteins of claim 23, wherein the average number of DM1 molecules per CD27L antigen binding protein is between 1 and 10.

25. The composition of CD27L antigen binding proteins of claim 24, wherein the average number of DM1 molecules per CD27L antigen binding protein is between 3 and 7.

26. The composition of CD27L antigen binding proteins of claim 25, wherein the average number of DM1 molecules per CD27L antigen binding protein is between 4 and 6.

27. The composition of CD27L antigen binding proteins of claim 25, wherein the average number of DM1 molecules per CD27L antigen binding protein is about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0.

28. The composition of CD27L antigen binding proteins of claim 24, wherein the composition is a pharmaceutical composition comprising a therapeutically effective amount of the CD27L antigen binding protein.

29. The composition of CD27L antigen binding proteins of claim 28, wherein the pharmaceutical composition is lyophilized.

* * * * *

SEQUENCE LISTING

```
<160> NUMBER OF SEQ ID NOS: 94

<210> SEQ ID NO 1
<211> LENGTH: 193
<212> TYPE: PRT
<213> ORGANISM: Homo sapiens
<220> FEATURE:
<221> NAME/KEY: MISC_FEATURE
<223> OTHER INFORMATION: Human CD27L

<400> SEQUENCE: 1

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125
```

```
Ala Val Gly Ile Cys Ser Pro Ala Ser Arg Ser Ile Ser Leu Leu Arg
        130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 2
<211> LENGTH: 217
<212> TYPE: PRT
<213> ORGANISM: Homo sapiens
<220> FEATURE:
<221> NAME/KEY: MISC_FEATURE
<223> OTHER INFORMATION: Human CD27 precursor

<400> SEQUENCE: 2

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr
210                 215

<210> SEQ ID NO 3
<211> LENGTH: 1350
<212> TYPE: DNA
<213> ORGANISM: Homo sapiens
<220> FEATURE:
<221> NAME/KEY: misc_feature
<223> OTHER INFORMATION: Ab1 Heavy Chain-encoding nucleotide sequence
```

<400> SEQUENCE: 3

```
cagatgcagc tgcaggagtc gggcccagga ctggtgaagc cctcacagac cctgtccctc    60
acctgcactg tctctgatgg ctccatcatc agtggtgttt actactggag ctggatccgc   120
cagcacccag ggaagggcct ggagtggatt ggatacatct attacagtgg gagcacctcc   180
tacaacccgt ccctcaagag tcgacttacc atgtcagtag acacgtctaa gaaccagttc   240
tccctgaagc tgagctctgt gactgccgcg gacacggccg tgtattactg tgcgaggagt   300
ggatacagct atgccctctt tgactactgg ggccagggaa ccctggtcac cgtctcctca   360
gctagcacca agggcccatc cgtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagag agttgagccc   660
aaatcttgtg acaaaactca cacatgccca ccgtgcccag cacctgaact cctgggggga   720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
aaagccaaag gcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                   1350
```

<210> SEQ ID NO 4
<211> LENGTH: 1350
<212> TYPE: DNA
<213> ORGANISM: Homo sapiens
<220> FEATURE:
<221> NAME/KEY: misc_feature
<223> OTHER INFORMATION: Ab2 Heavy Chain-encoding nucleotide sequence

<400> SEQUENCE: 4

```
caggtgcagc tgcaggagtc gggcccagga ctggtgaagc cttcacagac cctgtccctc    60
acctgcactg tctctggtga ctccatcatc agtggtggtt actactggag ctggatccgc   120
cagcacccag ggaagggcct ggagtggatt gggtacatct tttacagtgg gagcaccgac   180
tacaacccgt ccctcaagag tcgagttacc atatcagtag acacgtctaa gaaccagttc   240
tccctgaagc tgagctctgt gactgccgcg gacacggccg tatattactg tgcgaggagt   300
ggatacagct atgccctctt tgaccactgg ggccagggaa ccctggtcac cgtctcctca   360
gctagcacca agggcccatc cgtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
```

```
tacatctgca acgtgaatca caagcccagc aacaccaagg tggacaagag agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                     1350
```

<210> SEQ ID NO 5
<211> LENGTH: 1359
<212> TYPE: DNA
<213> ORGANISM: Homo sapiens
<220> FEATURE:
<221> NAME/KEY: misc_feature
<223> OTHER INFORMATION: Ab4 Heavy Chain-encoding nucleotide sequence

<400> SEQUENCE: 5

```
caggtgcagc tggtggagtc tgggggaggc gtggtccagc ctgggaggtc cctgagactc      60
tcctgtgcag cgtctggatt caccttcagt aactatggca tacactgggt ccgccaggct     120
ccaggcaagg gctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatgga     300
ggatatagtg gctacgattc ggggtttgac tactggggcc agggaaccct ggtcaccgtc     360
tcctcagcta gcaccaaggg cccatccgtc ttccccctgg cacctcctc caagagcacc     420
tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaagggca gccccgagaa ccacaggtgt acaccctgcc cccatcccgg    1080
gaggagatga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctatagca agctcaccgt ggacaagagc    1260
```

| | |
|---|---|
| aggtggcagc agggggaacgt cttctcatgc tccgtgatgc atgaggctct gcacaaccac | 1320 |
| tacacgcaga agagcctctc cctgtctccg ggtaaatga | 1359 |

<210> SEQ ID NO 6
<211> LENGTH: 1371
<212> TYPE: DNA
<213> ORGANISM: Homo sapiens
<220> FEATURE:
<221> NAME/KEY: misc_feature
<223> OTHER INFORMATION: Ab5 Heavy Chain-encoding nucleotide sequence

<400> SEQUENCE: 6

| | |
|---|---|
| caggtgcagc tggtgcagtc tggggctgag gtgaagaagc ctggggcctc agtgaaggtc | 60 |
| tcctgcaagg cttctggata cacct tcacc agttatgata tcaactgggt gcgacaggcc | 120 |
| actggacaag gcttgagtg gatgggatgg atgaacccta acagtggtaa cacaggctat | 180 |
| gcacagaagt tccagggcag agtcaccatg accaggaaca cctccataag cacagcctac | 240 |
| atggagctga gcagcctgag atctgaggac acggccgtgt attactgtgc gagagggtac | 300 |
| gatttttgga gtggttatta ctactactac tacggtatgg acgtctgggg ccaagggacc | 360 |
| acggtcaccg tctcctcagc tagcaccaag ggcccatccg tcttcccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagagag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |
| gaggtcaagt tcaactggta cgtggacggc gtggaggtgc ataatgccaa gacaaagccg | 900 |
| cgggaggagc agtacaacag cacgtaccgt gtggtcagcg tcctcaccgt cctgcaccag | 960 |
| gactggctga atggcaagga gtacaagtgc aaggtctcca acaaagccct cccagccccc | 1020 |
| atcgagaaaa ccatctccaa agccaaaggg cagccccgag aaccacaggt gtacaccctg | 1080 |
| cccccatccc gggaggagat gaccaagaac caggtcagcc tgacctgcct ggtcaaaggc | 1140 |
| ttctatccca gcgacatcgc cgtggagtgg gagagcaatg ggcagccgga gaacaactac | 1200 |
| aagaccacgc ctcccgtgct ggactccgac ggctccttct tcctctatag caagctcacc | 1260 |
| gtggacaaga gcaggtggca gcaggggaac gtcttctcat gctccgtgat gcatgaggct | 1320 |
| ctgcacaacc actacacgca gaagagcctc tccctgtctc cgggtaaatg a | 1371 |

<210> SEQ ID NO 7
<211> LENGTH: 1356
<212> TYPE: DNA
<213> ORGANISM: Homo sapiens
<220> FEATURE:
<221> NAME/KEY: misc_feature
<223> OTHER INFORMATION: Ab6 Heavy Chain-encoding nucleotide sequence

<400> SEQUENCE: 7

| | |
|---|---|
| caggttcagc tggtgcagtc tggagctgag gtgaagaagc ctggggcctc agtgaaggtc | 60 |
| tcctgcaagg cttctggtta caccttt acc agctatggta tcagctgggt gcgacaggcc | 120 |
| cctggacaag gcttgagtg gatgggatgg atcagcgctt acaatggtta cacacactat | 180 |
| gcacagaagc tccagggcag agtcaccatg accacagaca catccacgag cacagcctac | 240 |

| atggagctga | ggagcctgag | atctgacgac | acggccgtgt | attactgtgc | gagagactac | 300 |
| tggtggtaacg | actactacgg | tatggacgtc | tggggccaag | ggaccacggt | caccgtctcc | 360 |
| tcagctagca | ccaagggccc | atccgtcttc | ccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gagagttgag | 660 |
| cccaaatctt | gtgacaaaac | tcacacatgc | ccaccgtgcc | cagcacctga | actcctgggg | 720 |
| ggaccgtcag | tcttcctctt | ccccccaaaa | cccaaggaca | ccctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgtgtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggag | 1080 |
| gagatgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tatagcaagc | tcaccgtgga | caagagcagg | 1260 |
| tggcagcagg | ggaacgtctt | ctcatgctcc | gtgatgcatg | aggctctgca | caaccactac | 1320 |
| acgcagaaga | gcctctccct | gtctccgggt | aaatga | | | 1356 |

<210> SEQ ID NO 8
<211> LENGTH: 1350
<212> TYPE: DNA
<213> ORGANISM: Homo sapiens
<220> FEATURE:
<221> NAME/KEY: misc_feature
<223> OTHER INFORMATION: Ab7 Heavy Chain-encoding nucleotide sequence

<400> SEQUENCE: 8

| caggtgcagc | tggtggagtc | tgggggaggc | gtggtccagc | ctgggaggtc | cctgagactc | 60 |
| tcctgtgcag | cgtctggatt | caccttcagt | acctatggca | tgcactgggt | ccgccaggct | 120 |
| ccaggcaagg | ggctggagtg | ggtggcagtt | atatggtatg | atggaagtaa | taatactat | 180 |
| ggagactccg | tgaagggccg | attcaccatc | tccagagaca | attccaagaa | cacgctgtat | 240 |
| ctgcaaatga | acagcctgag | agccgaggac | acggctgtgt | attactgtgc | gagagataac | 300 |
| agtcactact | actacggtat | ggacgtctgg | ggccaaggga | ccacggtcac | cgtctcctca | 360 |
| gctagcacca | agggcccatc | cgtcttccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | cgccctgac | cagcggcgtg | cacaccttcc | cggctgtcct | acagtcctca | 540 |
| ggactctact | ccctcagcag | cgtggtgacc | gtgccctcca | gcagctttggg | cacccagacc | 600 |
| tacatctgca | acgtgaatca | caagcccagc | aacaccaagg | tggacaagag | agttgagccc | 660 |
| aaatcttgtg | acaaaactca | cacatgccca | ccgtgcccag | cacctgaact | cctgggggga | 720 |
| ccgtcagtct | tcctcttccc | cccaaaaccc | aaggacaccc | tcatgatctc | ccggacccct | 780 |
| gaggtcacat | gcgtggtggt | ggacgtgagc | cacgaagacc | ctgaggtcaa | gttcaactgg | 840 |
| tacgtggacg | gcgtggaggt | gcataatgcc | aagacaaagc | cgcggggagga | gcagtacaac | 900 |

| | |
|---|---|
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

```
<210> SEQ ID NO 9
<211> LENGTH: 1356
<212> TYPE: DNA
<213> ORGANISM: Homo sapiens
<220> FEATURE:
<221> NAME/KEY: misc_feature
<223> OTHER INFORMATION: Ab8 Heavy Chain-encoding nucleotide sequence

<400> SEQUENCE: 9
```

| | |
|---|---|
| caggtgcagc tggtggagtc tgggggaggc gtggtccagc ctgggaggtc cctgagactc | 60 |
| tcctgtgcag cgtctggatt caccttcagt agctatggca tgcactgggt ccgccaggct | 120 |
| ccaggcaagg ggctggagtg gtggcagtt atatggtatg atggaagtga taaatacttt | 180 |
| gcagactccg tgaagggccg attcaccatc tccagagaca attccaagaa cacgctgtat | 240 |
| ctgcaaatga acagcctgag agccgaggac acggctgtgt attactgtgc gagagatggg | 300 |
| atagcaggag ctcgctacgt ctactttgac tactggggcc agggaaccct ggtcaccgtc | 360 |
| tcctcagcta gcaccaaggg cccatccgtc ttccccctgg cacctctc caagagcacc | 420 |
| tctgggggca cagcggccct gggctgcctg gtcaaggact acttccccga accggtgacg | 480 |
| gtgtcgtgga actcaggcgc cctgaccagc ggcgtgcaca ccttcccggc tgtcctacag | 540 |
| tcctcaggac tctactccct cagcagcgtg gtgaccgtgc cctccagcag cttgggcacc | 600 |
| cagacctaca tctgcaacgt gaatcacaag cccagcaaca ccaaggtgga caagaaagtt | 660 |
| gagcccaaat cttgtgacaa aactcacaca tgcccaccgt gcccagcacc tgaactcctg | 720 |
| gggggaccgt cagtcttcct cttccccca aaacccaagg acaccctcat gatctcccgg | 780 |
| acccctgagg tcacatgcgt ggtggtggac gtgagccacg aagaccctga ggtcaagttc | 840 |
| aactggtacg tggacggcgt ggaggtgcat aatgccaaga caaagccgcg ggaggagcag | 900 |
| tacaacagca cgtaccgtgt ggtcagcgtc ctcaccgtcc tgcaccagga ctggctgaat | 960 |
| ggcaaggagt acaagtgcaa ggtctccaac aaagccctcc cagccccat cgagaaaacc | 1020 |
| atctccaaag ccaaagggca gccccgagaa ccacaggtgt acaccctgcc cccatcccgg | 1080 |
| gaggagatga ccaagaacca ggtcagcctg acctgcctgg tcaaaggctt ctatcccagc | 1140 |
| gacatcgccg tggagtggga gagcaatggg cagccggaga caactacaa gaccacgcct | 1200 |
| cccgtgctgg actccgacgg ctccttcttc ctctatagca agctcaccgt ggacaagagc | 1260 |
| aggtggcagc aggggaacgt cttctcatgc tccgtgatgc atgaggctct gcacaaccac | 1320 |
| tacacgcaga agagcctctc cctgtctccg ggtaaa | 1356 |

```
<210> SEQ ID NO 10
<211> LENGTH: 450
<212> TYPE: PRT
<213> ORGANISM: Homo sapiens
<220> FEATURE:
```

<221> NAME/KEY: MISC_FEATURE
<223> OTHER INFORMATION: Ab1 Heavy Chain amino acid sequence

<400> SEQUENCE: 10

Gln Met Gln Leu Gln Glu Ser Gly Pro Gly Leu Val Lys Pro Ser Gln
1               5                   10                  15

Thr Leu Ser Leu Thr Cys Thr Val Ser Asp Gly Ser Ile Ile Ser Gly
            20                  25                  30

Val Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Ser Tyr Asn Pro Ser
    50                  55                  60

Leu Lys Ser Arg Leu Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Gly Tyr Ser Tyr Ala Leu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 11
<211> LENGTH: 450
<212> TYPE: PRT
<213> ORGANISM: Homo sapiens
<220> FEATURE:
<221> NAME/KEY: MISC_FEATURE
<223> OTHER INFORMATION: Ab2 Heavy Chain amino acid sequence

<400> SEQUENCE: 11

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Ile Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Phe Tyr Ser Gly Ser Thr Asp Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Gly Tyr Ser Tyr Ala Leu Phe Asp His Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 12
<211> LENGTH: 452
<212> TYPE: PRT
<213> ORGANISM: Homo sapiens
<220> FEATURE:
<221> NAME/KEY: MISC_FEATURE
<223> OTHER INFORMATION: Ab4 Heavy Chain amino acid sequence

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Ser Gly Tyr Asp Ser Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

-continued

Val Pro Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 456
<212> TYPE: PRT
<213> ORGANISM: Homo sapiens
<220> FEATURE:
<221> NAME/KEY: MISC_FEATURE
<223> OTHER INFORMATION: Ab5 Heavy Chain amino acid sequence

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Gly Tyr Asp Phe Trp Ser Gly Tyr Tyr Tyr Tyr Tyr Gly
            100                 105                 110
Met Asp Val Trp Gly Gln Gly Thr Thr Val Thr Val Ser Ala Ser
            115                 120                 125
Thr Lys Gly Pro Ser Val Phe Pro Leu Ala Pro Ser Ser Lys Ser Thr
130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
            195                 200                 205
Cys Asn Val Asn His Lys Pro Ser Asn Thr Lys Val Asp Lys Arg Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
            275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Glu Glu Met Thr
            355                 360                 365
Lys Asn Gln Val Ser Leu Thr Cys Leu Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
            435                 440                 445
Ser Leu Ser Leu Ser Pro Gly Lys
    450                 455

<210> SEQ ID NO 14
<211> LENGTH: 451
<212> TYPE: PRT
<213> ORGANISM: Homo sapiens
<220> FEATURE:
<221> NAME/KEY: MISC_FEATURE
<223> OTHER INFORMATION: Ab6 Heavy Chain amino acid sequence
```

```
<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Tyr Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Gly Asn Asp Tyr Tyr Gly Met Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 15
<211> LENGTH: 450
<212> TYPE: PRT
<213> ORGANISM: Homo sapiens
<220> FEATURE:
<221> NAME/KEY: MISC_FEATURE
<223> OTHER INFORMATION: Ab7 Heavy Chain amino acid sequence

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Ser His Tyr Tyr Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                305                 310                 315                 320
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 16
<211> LENGTH: 452
<212> TYPE: PRT
<213> ORGANISM: Homo sapiens
<220> FEATURE:
<221> NAME/KEY: MISC_FEATURE
<223> OTHER INFORMATION: Ab8 Heavy Chain amino acid sequence

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asp Lys Tyr Phe Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Ala Gly Ala Arg Tyr Val Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
                145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 17
<211> LENGTH: 120
<212> TYPE: PRT
<213> ORGANISM: Homo sapiens
<220> FEATURE:
<221> NAME/KEY: MISC_FEATURE
<223> OTHER INFORMATION: Ab1 Heavy Chain Variable Domain amino acid
      sequence

<400> SEQUENCE: 17

Gln Met Gln Leu Gln Glu Ser Gly Pro Gly Leu Val Lys Pro Ser Gln
1               5                   10                  15

Thr Leu Ser Leu Thr Cys Thr Val Ser Asp Gly Ser Ile Ile Ser Gly
            20                  25                  30

Val Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Ser Tyr Asn Pro Ser
    50                  55                  60

Leu Lys Ser Arg Leu Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Gly Tyr Ser Tyr Ala Leu Phe Asp Tyr Trp Gly Gln

```
                        100                 105                 110
Gly Thr Leu Val Thr Val Ser Ser
        115                 120

<210> SEQ ID NO 18
<211> LENGTH: 120
<212> TYPE: PRT
<213> ORGANISM: Homo sapiens
<220> FEATURE:
<221> NAME/KEY: MISC_FEATURE
<223> OTHER INFORMATION: Ab2 Heavy Chain Variable Domain amino acid
      sequence

<400> SEQUENCE: 18

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Ile Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Phe Tyr Ser Gly Ser Thr Asp Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Gly Tyr Ser Tyr Ala Leu Phe Asp His Trp Gly Gln
            100                 105                 110

Gly Thr Leu Val Thr Val Ser Ser
        115                 120

<210> SEQ ID NO 19
<211> LENGTH: 120
<212> TYPE: PRT
<213> ORGANISM: Homo sapiens
<220> FEATURE:
<221> NAME/KEY: MISC_FEATURE
<223> OTHER INFORMATION: Ab3 Heavy Chain Variable Domain amino acid
      sequence

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Asp Ser Gly Thr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Asp Tyr Ser Asn Tyr Tyr Phe Asp Tyr Trp Gly Gln
            100                 105                 110

Gly Thr Leu Val Thr Val Ser Ser
        115                 120

<210> SEQ ID NO 20
```

```
<211> LENGTH: 122
<212> TYPE: PRT
<213> ORGANISM: Homo sapiens
<220> FEATURE:
<221> NAME/KEY: MISC_FEATURE
<223> OTHER INFORMATION: Ab4 Heavy Chain Variable Domain amino acid
      sequence

<400> SEQUENCE: 20
```

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Ser Gly Tyr Asp Ser Gly Phe Asp Tyr Trp
            100                 105                 110

Gly Gln Gly Thr Leu Val Thr Val Ser Ser
        115                 120

```
<210> SEQ ID NO 21
<211> LENGTH: 126
<212> TYPE: PRT
<213> ORGANISM: Homo sapiens
<220> FEATURE:
<221> NAME/KEY: MISC_FEATURE
<223> OTHER INFORMATION: Ab3 Heavy Chain Variable Domain amino acid
      sequence

<400> SEQUENCE: 21
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Phe Trp Ser Gly Tyr Tyr Tyr Tyr Tyr Gly
            100                 105                 110

Met Asp Val Trp Gly Gln Gly Thr Thr Val Thr Val Ser Ser
        115                 120                 125

```
<210> SEQ ID NO 22
<211> LENGTH: 121
<212> TYPE: PRT
<213> ORGANISM: Homo sapiens
<220> FEATURE:
<221> NAME/KEY: MISC_FEATURE
<223> OTHER INFORMATION: Ab6 Heavy Chain Variable Domain amino acid
      sequence
```

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Tyr Thr His Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Gly Gly Asn Asp Tyr Tyr Gly Met Asp Val Trp Gly
            100                 105                 110

Gln Gly Thr Thr Val Thr Val Ser Ser
        115                 120

<210> SEQ ID NO 23
<211> LENGTH: 120
<212> TYPE: PRT
<213> ORGANISM: Homo sapiens
<220> FEATURE:
<221> NAME/KEY: MISC_FEATURE
<223> OTHER INFORMATION: Ab7 Heavy Chain Variable Domain amino acid
      sequence

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Gly Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Ser His Tyr Tyr Gly Met Asp Val Trp Gly Gln
            100                 105                 110

Gly Thr Thr Val Thr Val Ser Ser
        115                 120

<210> SEQ ID NO 24
<211> LENGTH: 122
<212> TYPE: PRT
<213> ORGANISM: Homo sapiens
<220> FEATURE:
<221> NAME/KEY: MISC_FEATURE
<223> OTHER INFORMATION: Ab8 Heavy Chain Variable Domain amino acid
      sequence

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
                    20                  25                  30
Gly Met His Trp Val Arg Gln Ala Pro Gly Lys Gly Leu Glu Trp Val
            35                  40                  45

Ala Val Ile Trp Tyr Asp Gly Ser Asp Lys Tyr Phe Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Ala Gly Ala Arg Tyr Val Tyr Phe Asp Tyr Trp
                100                 105                 110

Gly Gln Gly Thr Leu Val Thr Val Ser Ser
            115                 120

<210> SEQ ID NO 25
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab1 Heavy Chain CDR1 amino acid sequence

<400> SEQUENCE: 25

Ser Gly Val Tyr Tyr Trp Ser
1               5

<210> SEQ ID NO 26
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab2 Heavy Chain CDR1 amino acid sequence

<400> SEQUENCE: 26

Ser Gly Gly Tyr Tyr Trp Ser
1               5

<210> SEQ ID NO 27
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab3 Heavy Chain CDR1 amino acid sequence

<400> SEQUENCE: 27

Ser Tyr Ala Met Ser
1               5

<210> SEQ ID NO 28
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab4 Heavy Chain CDR1 amino acid sequence

<400> SEQUENCE: 28

Asn Tyr Gly Ile His
1               5

<210> SEQ ID NO 29
<211> LENGTH: 5
```

```
<212> TYPE: PRT
<213> ORGANISM: Homo sapiens
<220> FEATURE:
<221> NAME/KEY: MISC_FEATURE
<223> OTHER INFORMATION: SYDIN

<400> SEQUENCE: 29

Ser Tyr Asp Ile Asn
1               5

<210> SEQ ID NO 30
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab6 Heavy Chain CDR1 amino acid sequence

<400> SEQUENCE: 30

Ser Tyr Gly Ile Ser
1               5

<210> SEQ ID NO 31
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab7 Heavy Chain CDR1 amino acid sequence

<400> SEQUENCE: 31

Thr Tyr Gly Met His
1               5

<210> SEQ ID NO 32
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab8 Heavy Chain CDR1 amino acid sequence

<400> SEQUENCE: 32

Ser Tyr Gly Met His
1               5

<210> SEQ ID NO 33
<211> LENGTH: 16
<212> TYPE: PRT
<213> ORGANISM: Homo sapiens
<220> FEATURE:
<221> NAME/KEY: MISC_FEATURE
<223> OTHER INFORMATION: Ab1 Heavy Chain CDR2 amino acid sequence

<400> SEQUENCE: 33

Tyr Ile Tyr Tyr Ser Gly Ser Thr Ser Tyr Asn Pro Ser Leu Lys Ser
1               5                   10                  15

<210> SEQ ID NO 34
<211> LENGTH: 16
<212> TYPE: PRT
<213> ORGANISM: Homo sapiens
<220> FEATURE:
<221> NAME/KEY: MISC_FEATURE
<223> OTHER INFORMATION: Ab2 Heavy Chain CDR2 amino acid sequence

<400> SEQUENCE: 34

Tyr Ile Phe Tyr Ser Gly Ser Thr Asp Tyr Asn Pro Ser Leu Lys Ser
```

```
<210> SEQ ID NO 35
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab3 Heavy Chain CDR2 amino acid sequence

<400> SEQUENCE: 35

Val Ile Ser Asp Ser Gly Gly Thr Thr Asp Tyr Ala Asp Ser Val Lys
1               5                   10                  15
Gly

<210> SEQ ID NO 36
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab4 Heavy Chain CDR2 amino acid sequence

<400> SEQUENCE: 36

Val Ile Trp Tyr Asp Gly Ser Asn Lys Tyr Tyr Ala Asp Ser Val Lys
1               5                   10                  15
Gly

<210> SEQ ID NO 37
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab5 Heavy Chain CDR2 amino acid sequence

<400> SEQUENCE: 37

Trp Met Asn Pro Asn Ser Gly Asn Thr Gly Tyr Ala Gln Lys Phe Gln
1               5                   10                  15
Gly

<210> SEQ ID NO 38
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab6 Heavy Chain CDR2 amino acid sequence

<400> SEQUENCE: 38

Trp Ile Ser Ala Tyr Asn Gly Tyr Thr His Tyr Ala Gln Lys Leu Gln
1               5                   10                  15
Gly

<210> SEQ ID NO 39
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab7 Heavy Chain CDR2 amino acid sequence

<400> SEQUENCE: 39

Val Ile Trp Tyr Asp Gly Ser Asn Lys Tyr Tyr Gly Asp Ser Val Lys
1               5                   10                  15
```

Gly

<210> SEQ ID NO 40
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab8 Heavy Chain CDR2 amino acid sequence

<400> SEQUENCE: 40

Val Ile Trp Tyr Asp Gly Ser Asp Lys Tyr Phe Ala Asp Ser Val Lys
1               5                   10                  15

Gly

<210> SEQ ID NO 41
<211> LENGTH: 10
<212> TYPE: PRT
<213> ORGANISM: Homo sapiens
<220> FEATURE:
<221> NAME/KEY: MISC_FEATURE
<223> OTHER INFORMATION: Ab1 Heavy Chain CDR3 amino acid sequence

<400> SEQUENCE: 41

Ser Gly Tyr Ser Tyr Ala Leu Phe Asp Tyr
1               5                   10

<210> SEQ ID NO 42
<211> LENGTH: 10
<212> TYPE: PRT
<213> ORGANISM: Homo sapiens
<220> FEATURE:
<221> NAME/KEY: MISC_FEATURE
<223> OTHER INFORMATION: Ab2 Heavy Chain CDR3 amino acid sequence

<400> SEQUENCE: 42

Ser Gly Tyr Ser Tyr Ala Leu Phe Asp His
1               5                   10

<210> SEQ ID NO 43
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab3 Heavy Chain CDR3 amino acid sequence

<400> SEQUENCE: 43

His Asp Tyr Ser Asn Arg Tyr Tyr Phe Asp Tyr
1               5                   10

<210> SEQ ID NO 44
<211> LENGTH: 13
<212> TYPE: PRT
<213> ORGANISM: Homo sapiens
<220> FEATURE:
<221> NAME/KEY: MISC_FEATURE
<223> OTHER INFORMATION: Ab4 Heavy Chain CDR3 amino acid sequence

<400> SEQUENCE: 44

Asp Gly Gly Tyr Ser Gly Tyr Asp Ser Gly Phe Asp Tyr
1               5                   10

<210> SEQ ID NO 45
<211> LENGTH: 17
<212> TYPE: PRT

-continued

<213> ORGANISM: Homo sapiens
<220> FEATURE:
<221> NAME/KEY: MISC_FEATURE
<223> OTHER INFORMATION: GYDFWSGYYYYYYGMDV

<400> SEQUENCE: 45

Gly Tyr Asp Phe Trp Ser Gly Tyr Tyr Tyr Tyr Tyr Tyr Gly Met Asp
1               5                   10                  15
Val

<210> SEQ ID NO 46
<211> LENGTH: 12
<212> TYPE: PRT
<213> ORGANISM: Homo sapiens
<220> FEATURE:
<221> NAME/KEY: MISC_FEATURE
<223> OTHER INFORMATION: Ab6 Heavy Chain CDR3 amino acid sequence

<400> SEQUENCE: 46

Asp Tyr Gly Gly Asn Asp Tyr Tyr Gly Met Asp Val
1               5                   10

<210> SEQ ID NO 47
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab7 Heavy Chain CDR3 amino acid sequence

<400> SEQUENCE: 47

Asp Asn Ser His Tyr Tyr Tyr Gly Met Asp Val
1               5                   10

<210> SEQ ID NO 48
<211> LENGTH: 13
<212> TYPE: PRT
<213> ORGANISM: Homo sapiens
<220> FEATURE:
<221> NAME/KEY: MISC_FEATURE
<223> OTHER INFORMATION: Ab8 Heavy Chain CDR3 amino acid sequence

<400> SEQUENCE: 48

Asp Gly Ile Ala Gly Ala Arg Tyr Val Tyr Phe Asp Tyr
1               5                   10

<210> SEQ ID NO 49
<211> LENGTH: 642
<212> TYPE: DNA
<213> ORGANISM: Homo sapiens
<220> FEATURE:
<221> NAME/KEY: misc_feature
<223> OTHER INFORMATION: Ab1 Light Chain-encoding nucleotide sequence

<400> SEQUENCE: 49
gacatccaga tgacccagtc tccatcctcc ctgtctgcat ctttaggaga cagagtcacc    60
atcacttgcc gggcaagtca gagcgttgac agatatttca attggtatca gcagaaacct   120
gggaaagccc ctaaggtcct gatctttgct gcatccagtt tgcaaagtgg ggtcccatca   180
aggttcggtg gcagtggatc tgggacagat ttcactctca ccatcagcag tctgcaacct   240
gaagattttg caacttacta ctgtcaacag agctacagta ccccgtggac gttcggccaa   300
gggaccaagg tggaagtcaa acgtacggtg gctgcaccat ctgtcttcat cttcccgcca   360
tctgatgagc agttgaaatc tggaactgcc tctgttgtgt gcctgctgaa taacttctat   420

```
cccagagagg ccaaagtaca gtggaaggtg ataacgccc tccaatcggg taactcccag    480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 50
<211> LENGTH: 642
<212> TYPE: DNA
<213> ORGANISM: Homo sapiens
<220> FEATURE:
<221> NAME/KEY: misc_feature
<223> OTHER INFORMATION: Ab2 Light Chain-encoding nucleotide sequence

<400> SEQUENCE: 50

```
gacatccaga tgacccagtc cccatcctcc ctgtctgcat ctgtaggaga cagagtcacc    60
atcagttgcc gggcaagtca gttcattggc agatatttca attggtatca gcagcaacca   120
gggaaagccc ctaaggtcct gatctatgct gaatccagtt tgcaaagtgg ggtcccatca   180
agattcagtg gcagtggatc tgggacagaa ttcactctca ccatcagcag tctgcaacct   240
gaagattttg caagatacta ctgtcaacag agttacagta cccgtggac gttcggccaa    300 gggaccaagg tggaaatcaa acgtacggtg gctgcaccat ctgtcttcat cttcccgcca   360
tctgatgagc agttgaaatc tggaactgcc tctgttgtgt gcctgctgaa taacttctat    420
cccagagagg ccaaagtaca gtggaaggtg ataacgccc tccaatcggg taactcccag    480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 51
<211> LENGTH: 660
<212> TYPE: DNA
<213> ORGANISM: Homo sapiens
<220> FEATURE:
<221> NAME/KEY: misc_feature
<223> OTHER INFORMATION: Ab4 Light Chain-encoding nucleotide sequence

<400> SEQUENCE: 51

```
gatattgtga tgactcagtc tccactctcc ctgcccgtca cccctggaga gccggcctcc    60
atctcctgca ggtctagtca gagcctcctg aatagtaatg gatacaacta tttggattgg   120
tacctgcaga agccagggca gtctccacag ttcctgatct atttgggttc ttatcgggcc    180
tccggggtcc ctgacaggtt cagtggcagt ggatcaggca cagattttac actgagaatc   240
agcagagtgg aggctgagga tgttggggtt tattactgta tacaaactct acaaactcca   300
ttcactttcg gccctgggac caaagtggat atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc    540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

<210> SEQ ID NO 52
<211> LENGTH: 651
<212> TYPE: DNA
<213> ORGANISM: Homo sapiens
<220> FEATURE:
<221> NAME/KEY: misc_feature
<223> OTHER INFORMATION: Ab5 Light Chain-encoding nucleotide sequence

<400> SEQUENCE: 52

| | | | | | |
|---|---|---|---|---|---|
| gaaattgtgt | tgacgcagtc | tcctggcacc | ctgtctttgt | ctccagggga | aagagccacc | 60 |
| ctctcctgca | gggccagtca | gagtgttagc | agcagctact | tagcctggta | ccagcagaga | 120 |
| cctggccagg | ctcccaggct | cctcatctat | ggtgcatcca | gcagggccac | tggcatccca | 180 |
| gacaggttca | gtggcagtgg | gtctgggaca | gacttcactc | tcaccatcag | cagtctggag | 240 |
| cctgaagatt | ttgcagtgta | ttactgtctg | cagtctggta | gctctgtccc | gctcactttc | 300 |
| ggcggaggga | ccaaggtgga | gatcaaacgt | acggtggctg | caccatctgt | cttcatcttc | 360 |
| ccgccatctg | atgagcagtt | gaaatctgga | actgcctctg | ttgtgtgcct | gctgaataac | 420 |
| ttctatccca | gagaggccaa | agtacagtgg | aaggtggata | acgccctcca | atcgggtaac | 480 |
| tcccaggaga | gtgtcacaga | gcaggacagc | aaggacagca | cctacagcct | cagcagcacc | 540 |
| ctgacgctga | gcaaagcaga | ctacgagaaa | cacaaagtct | acgcctgcga | agtcacccat | 600 |
| cagggcctga | gctcgcccgt | cacaaagagc | ttcaacaggg | gagagtgtta | a | 651 |

<210> SEQ ID NO 53
<211> LENGTH: 651
<212> TYPE: DNA
<213> ORGANISM: Homo sapiens
<220> FEATURE:
<221> NAME/KEY: misc_feature
<223> OTHER INFORMATION: Ab6 Light Chain-encoding nucleotide sequence

<400> SEQUENCE: 53

| | | | | | |
|---|---|---|---|---|---|
| cagtctgtgc | tgactcagcc | accctcagcg | tctgggaccc | ccgggcagag | ggtcaccatc | 60 |
| tcttgttctg | gaagcagctc | caacatcgga | attaattatg | tatactggta | ccagcagctc | 120 |
| ccaggaacgg | cccccaaact | cctcatctat | aggagtgatc | agcggccctc | aggggtccct | 180 |
| gaccgattct | ctggctccaa | gtctggcacc | tcagcctccc | tggccctcag | tgggctccgg | 240 |
| tccgaggatg | aggctgatta | ttactgtgca | gcatgggatg | acagcctgag | tggtgtggtg | 300 |
| ttcggcggag | ggaccaagct | gaccgtccta | ggccaaccga | aagcggcgcc | ctcggtcact | 360 |
| ctgttcccgc | cctcctctga | ggagcttcaa | gccaacaagg | ccacactggt | gtgtctcata | 420 |
| agtgacttct | acccgggagc | cgtgacagtg | gcctggaagg | cagatagcag | ccccgtcaag | 480 |
| gcgggagtgg | agaccaccac | accctccaaa | caaagcaaca | acaagtacgc | ggccagcagc | 540 |
| tatctgagcc | tgacgcctga | gcagtggaag | tcccacagaa | gctacagctg | ccaggtcacg | 600 |
| catgaaggga | gcaccgtgga | gaagacagtg | gcccctacag | aatgttcata | g | 651 |

<210> SEQ ID NO 54
<211> LENGTH: 651
<212> TYPE: DNA
<213> ORGANISM: Homo sapiens
<220> FEATURE:
<221> NAME/KEY: misc_feature
<223> OTHER INFORMATION: Ab7 Light Chain-encoding nucleotide sequence

<400> SEQUENCE: 54

| | | | | | |
|---|---|---|---|---|---|
| cagtctgtgc | tgacgcagcc | gccctcagtg | tctggggccc | cagggcagag | ggtcaccatc | 60 |
| tcctgcactg | ggagcagctc | caacatcggg | gcaggttatg | atgtaaattg | gtatcagcag | 120 |
| ttcccaggaa | cagcccccaa | actcctcatc | tatgttaaca | acaatcggcc | ctcaggagtc | 180 |
| cctgaccgat | tctctggctc | cacgtctggc | acctcagcct | ccctggccat | cactggactc | 240 |

```
caggctgagg atgaggctga ttattactgc cagtcctatg acaccagcct gagtgcttcg    300
gtattcggcg agggaccag actgaccgtc ctaggccaac cgaaagcggc gccctcggtc     360
actctgttcc cgccctcctc tgaggagctt caagccaaca aggccacact ggtgtgtctc    420
ataagtgact tctacccggg agccgtgaca gtggcctgga aggcagatag cagccccgtc    480
aaggcgggag tggagaccac cacaccctcc aaacaaagca acaacaagta cgcggccagc    540
agctatctga gcctgacgcc tgagcagtgg aagtcccaca aagctacag ctgccaggtc     600 acgcatgaag ggagcaccgt ggagaagaca gtggccccta cagaatgttc a             651
```

<210> SEQ ID NO 55
<211> LENGTH: 645
<212> TYPE: DNA
<213> ORGANISM: Homo sapiens
<220> FEATURE:
<221> NAME/KEY: misc_feature
<223> OTHER INFORMATION: Ab8 Light Chain-encoding nucleotide sequence

<400> SEQUENCE: 55

```
gacatccaga tgacccagtc tccatcctcc ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaggtgg ggtcccatca   180
aagttcagcg gcagtggatc tgggacagat ttcactctca ccatcagcag cctgcagcct   240
gaagattttg caacttatta ctgccaacaa tattataatt acccattcac tttcggccct   300
gggaccacag tggatatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacectgacg   540 ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 56
<211> LENGTH: 214
<212> TYPE: PRT
<213> ORGANISM: Homo sapiens
<220> FEATURE:
<221> NAME/KEY: MISC_FEATURE
<223> OTHER INFORMATION: Ab1 Light Chain amino acid sequence

<400> SEQUENCE: 56

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Ser Val Asp Arg Tyr
            20                  25                  30

Phe Asn Trp Tyr Gln Gln Lys Pro Gly Lys Ala Pro Lys Val Leu Ile
        35                  40                  45

Phe Ala Ala Ser Ser Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Val Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 57
<211> LENGTH: 214
<212> TYPE: PRT
<213> ORGANISM: Homo sapiens
<220> FEATURE:
<221> NAME/KEY: MISC_FEATURE
<223> OTHER INFORMATION: Ab2 Light Chain amino acid sequence

<400> SEQUENCE: 57

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Phe Ile Gly Arg Tyr
            20                  25                  30

Phe Asn Trp Tyr Gln Gln Pro Gly Lys Ala Pro Lys Val Leu Ile
        35                  40                  45

Tyr Ala Glu Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Arg Tyr Tyr Cys Gln Gln Ser Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 58
<211> LENGTH: 219
<212> TYPE: PRT

<213> ORGANISM: Homo sapiens
<220> FEATURE:
<221> NAME/KEY: MISC_FEATURE
<223> OTHER INFORMATION: Ab4 Light Chain amino acid sequence

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Asn Gly Tyr Asn Tyr Leu Asp Trp Tyr Leu Gln Lys Pro Gly Gln Ser
        35                  40                  45

Pro Gln Phe Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ile Gln Thr
                85                  90                  95

Leu Gln Thr Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 59
<211> LENGTH: 216
<212> TYPE: PRT
<213> ORGANISM: Homo sapiens
<220> FEATURE:
<221> NAME/KEY: MISC_FEATURE
<223> OTHER INFORMATION: Ab5 Light Chain amino acid sequence

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Leu Gln Ser Gly Ser Ser Val
                85                  90                  95

Pro Leu Thr Phe Gly Gly Gly Thr Lys Val Glu Ile Lys Arg Thr Val

```
                    100                 105                 110
Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135             140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
210                 215

<210> SEQ ID NO 60
<211> LENGTH: 216
<212> TYPE: PRT
<213> ORGANISM: Homo sapiens
<220> FEATURE:
<221> NAME/KEY: MISC_FEATURE
<223> OTHER INFORMATION: Ab6 Light Chain amino acid sequence

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Tyr Val Tyr Trp Tyr Gln Gln Leu Pro Gly Thr Ala Pro Lys Leu Leu
            35                  40                  45

Ile Tyr Arg Ser Asp Gln Arg Pro Ser Gly Val Pro Asp Arg Phe Ser
        50                  55                  60

Gly Ser Lys Ser Gly Thr Ser Ala Ser Leu Ala Leu Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
210                 215

<210> SEQ ID NO 61
<211> LENGTH: 217
```

```
<212> TYPE: PRT
<213> ORGANISM: Homo sapiens
<220> FEATURE:
<221> NAME/KEY: MISC_FEATURE
<223> OTHER INFORMATION: Ab7 Light Chain amino acid sequence

<400> SEQUENCE: 61
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val Asn Trp Tyr Gln Gln Phe Pro Gly Thr Ala Pro Lys Leu
        35                  40                  45

Leu Ile Tyr Val Asn Asn Asn Arg Pro Ser Gly Val Pro Asp Arg Phe
    50                  55                  60

Ser Gly Ser Thr Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Ser Ala Ser Val Phe Gly Gly Thr Arg Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

```
<210> SEQ ID NO 62
<211> LENGTH: 214
<212> TYPE: PRT
<213> ORGANISM: Homo sapiens
<220> FEATURE:
<221> NAME/KEY: MISC_FEATURE
<223> OTHER INFORMATION: Ab8 Light Chain amino acid sequence

<400> SEQUENCE: 62
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Gly Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Phe
                85                  90                  95

```
Thr Phe Gly Pro Gly Thr Thr Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 63
<211> LENGTH: 107
<212> TYPE: PRT
<213> ORGANISM: Homo sapiens
<220> FEATURE:
<221> NAME/KEY: MISC_FEATURE
<223> OTHER INFORMATION: Ab1 Light Chain Variable Domain amino acid
      sequence

<400> SEQUENCE: 63

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Ser Val Asp Arg Tyr
            20                  25                  30

Phe Asn Trp Tyr Gln Gln Lys Pro Gly Lys Ala Pro Lys Val Leu Ile
        35                  40                  45

Phe Ala Ala Ser Ser Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Val Lys
            100                 105
```

<210> SEQ ID NO 64
<211> LENGTH: 107
<212> TYPE: PRT
<213> ORGANISM: Homo sapiens
<220> FEATURE:
<221> NAME/KEY: MISC_FEATURE
<223> OTHER INFORMATION: Ab2 Light Chain Variable Domain amino acid
      sequence

<400> SEQUENCE: 64

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Phe Ile Gly Arg Tyr
            20                  25                  30

Phe Asn Trp Tyr Gln Gln Pro Gly Lys Ala Pro Lys Val Leu Ile
        35                  40                  45

Tyr Ala Glu Ser Ser Leu Gln Ser Gly Val Pro Ser Arg Phe Ser Gly
```

```
                    50                  55                  60
Ser Gly Ser Gly Thr Glu Phe Thr Leu Thr Ile Ser Ser Leu Gln Pro
 65                  70                  75                  80

Glu Asp Phe Ala Arg Tyr Tyr Cys Gln Gln Ser Tyr Ser Thr Pro Trp
                 85                  90                  95

Thr Phe Gly Gln Gly Thr Lys Val Glu Ile Lys
            100                 105
```

<210> SEQ ID NO 65
<211> LENGTH: 108
<212> TYPE: PRT
<213> ORGANISM: Homo sapiens
<220> FEATURE:
<221> NAME/KEY: MISC_FEATURE
<223> OTHER INFORMATION: Ab3 Light Chain Variable Domain amino acid
      sequence

<400> SEQUENCE: 65

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Phe Ser Ser Asn
                 20                  25                  30

Tyr Leu Ala Trp Tyr Gln Gln Lys Pro Gly Gln Ala Pro Arg Leu Phe
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln Tyr Gly Ile Ser Pro
                 85                  90                  95

Cys Ser Phe Gly Gln Gly Thr Lys Leu Glu Ile Lys
            100                 105
```

<210> SEQ ID NO 66
<211> LENGTH: 112
<212> TYPE: PRT
<213> ORGANISM: Homo sapiens
<220> FEATURE:
<221> NAME/KEY: MISC_FEATURE
<223> OTHER INFORMATION: Ab4 Light Chain Variable Domain amino acid
      sequence

<400> SEQUENCE: 66

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Asn Ser
                 20                  25                  30

Asn Gly Tyr Asn Tyr Leu Asp Trp Tyr Leu Gln Lys Pro Gly Gln Ser
             35                  40                  45

Pro Gln Phe Leu Ile Tyr Leu Gly Ser Tyr Arg Ala Ser Gly Val Pro
         50                  55                  60

Asp Arg Phe Ser Gly Ser Gly Ser Gly Thr Asp Phe Thr Leu Arg Ile
 65                  70                  75                  80

Ser Arg Val Glu Ala Glu Asp Val Gly Val Tyr Tyr Cys Ile Gln Thr
                 85                  90                  95

Leu Gln Thr Pro Phe Thr Phe Gly Pro Gly Thr Lys Val Asp Ile Lys
            100                 105                 110
```

<210> SEQ ID NO 67

<211> LENGTH: 109
<212> TYPE: PRT
<213> ORGANISM: Homo sapiens
<220> FEATURE:
<221> NAME/KEY: MISC_FEATURE
<223> OTHER INFORMATION: Ab5 Light Chain Variable Domain amino acid
      sequence

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Leu Gln Ser Gly Ser Ser Val
                85                  90                  95

Pro Leu Thr Phe Gly Gly Gly Thr Lys Val Glu Ile Lys
            100                 105

<210> SEQ ID NO 68
<211> LENGTH: 110
<212> TYPE: PRT
<213> ORGANISM: Homo sapiens
<220> FEATURE:
<221> NAME/KEY: MISC_FEATURE
<223> OTHER INFORMATION: Ab6 Light Chain Variable Domain amino acid
      sequence

<400> SEQUENCE: 68

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ile Asn
            20                  25                  30

Tyr Val Tyr Trp Tyr Gln Gln Leu Pro Gly Thr Ala Pro Lys Leu Leu
        35                  40                  45

Ile Tyr Arg Ser Asp Gln Arg Pro Ser Gly Val Pro Asp Arg Phe Ser
 50                  55                  60

Gly Ser Lys Ser Gly Thr Ser Ala Ser Leu Ala Leu Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110

<210> SEQ ID NO 69
<211> LENGTH: 111
<212> TYPE: PRT
<213> ORGANISM: Homo sapiens
<220> FEATURE:
<221> NAME/KEY: MISC_FEATURE
<223> OTHER INFORMATION: Ab7 Light Chain Variable Domain amino acid
      sequence

<400> SEQUENCE: 69

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val Asn Trp Tyr Gln Gln Phe Pro Gly Thr Ala Pro Lys Leu
        35                  40                  45

Leu Ile Tyr Val Asn Asn Arg Pro Ser Gly Val Pro Asp Arg Phe
    50                  55                  60

Ser Gly Ser Thr Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Ser Ala Ser Val Phe Gly Gly Gly Thr Arg Leu Thr Val Leu
            100                 105                 110

<210> SEQ ID NO 70
<211> LENGTH: 107
<212> TYPE: PRT
<213> ORGANISM: Homo sapiens
<220> FEATURE:
<221> NAME/KEY: MISC_FEATURE
<223> OTHER INFORMATION: Ab8 Light Chain Variable Domain amino acid
      sequence

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Gly Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Phe
                85                  90                  95

Thr Phe Gly Pro Gly Thr Thr Val Asp Ile Lys
            100                 105

<210> SEQ ID NO 71
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab1 Light Chain CDR1 amino acid sequence

<400> SEQUENCE: 71

Arg Ala Ser Gln Ser Val Asp Arg Tyr Phe Asn
1               5                   10

<210> SEQ ID NO 72
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab2 Light Chain CDR1 amino acid sequence

<400> SEQUENCE: 72

Arg Ala Ser Gln Phe Ile Gly Arg Tyr Phe Asn
1               5                   10

```
<210> SEQ ID NO 73
<211> LENGTH: 12
<212> TYPE: PRT
<213> ORGANISM: Homo sapiens
<220> FEATURE:
<221> NAME/KEY: MISC_FEATURE
<223> OTHER INFORMATION: Ab3 Light Chain CDR1 amino acid sequence

<400> SEQUENCE: 73

Arg Ala Ser Gln Ser Phe Ser Ser Asn Tyr Leu Ala
1               5                   10

<210> SEQ ID NO 74
<211> LENGTH: 16
<212> TYPE: PRT
<213> ORGANISM: Homo sapiens
<220> FEATURE:
<221> NAME/KEY: MISC_FEATURE
<223> OTHER INFORMATION: Ab4 Light Chain CDR1 amino acid sequence

<400> SEQUENCE: 74

Arg Ser Ser Gln Ser Leu Leu Asn Ser Asn Gly Tyr Asn Tyr Leu Asp
1               5                   10                  15

<210> SEQ ID NO 75
<211> LENGTH: 12
<212> TYPE: PRT
<213> ORGANISM: Homo sapiens
<220> FEATURE:
<221> NAME/KEY: MISC_FEATURE
<223> OTHER INFORMATION: Ab5 Light Chain CDR1 amino acid sequence

<400> SEQUENCE: 75

Arg Ala Ser Gln Ser Val Ser Ser Ser Tyr Leu Ala
1               5                   10

<210> SEQ ID NO 76
<211> LENGTH: 13
<212> TYPE: PRT
<213> ORGANISM: Homo sapiens
<220> FEATURE:
<221> NAME/KEY: MISC_FEATURE
<223> OTHER INFORMATION: Ab6 Light Chain CDR1 amino acid sequence

<400> SEQUENCE: 76

Ser Gly Ser Ser Ser Asn Ile Gly Ile Asn Tyr Val Tyr
1               5                   10

<210> SEQ ID NO 77
<211> LENGTH: 14
<212> TYPE: PRT
<213> ORGANISM: Homo sapiens
<220> FEATURE:
<221> NAME/KEY: MISC_FEATURE
<223> OTHER INFORMATION: Ab7 Light Chain CDR1 amino acid sequence

<400> SEQUENCE: 77

Thr Gly Ser Ser Ser Asn Ile Gly Ala Gly Tyr Asp Val Asn
1               5                   10

<210> SEQ ID NO 78
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab8 Light Chain CDR1 amino acid sequence
```

```
<400> SEQUENCE: 78

Arg Ala Ser Gln Gly Ile Ser Asn Tyr Leu Ala
1               5                   10

<210> SEQ ID NO 79
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab1 Light Chain CDR2 amino acid sequence

<400> SEQUENCE: 79

Ala Ala Ser Ser Leu Gln Ser
1               5

<210> SEQ ID NO 80
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab2 Light Chain CDR2 amino acid sequence

<400> SEQUENCE: 80

Ala Glu Ser Ser Leu Gln Ser
1               5

<210> SEQ ID NO 81
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab2 Light Chain CDR2 amino acid sequence

<400> SEQUENCE: 81

Gly Ala Ser Ser Arg Ala Thr
1               5

<210> SEQ ID NO 82
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab4 Light Chain CDR2 amino acid sequence

<400> SEQUENCE: 82

Leu Gly Ser Tyr Arg Ala Ser
1               5

<210> SEQ ID NO 83
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab5 Light Chain CDR2 amino acid sequence

<400> SEQUENCE: 83

Gly Ala Ser Ser Arg Ala Thr
1               5
```

```
<210> SEQ ID NO 84
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab6 Light Chain CDR2 amino acid sequence

<400> SEQUENCE: 84

Arg Ser Asp Gln Arg Pro Ser
1               5

<210> SEQ ID NO 85
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab7 Light Chain CDR2 amino acid sequence

<400> SEQUENCE: 85

Val Asn Asn Asn Arg Pro Ser
1               5

<210> SEQ ID NO 86
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab8 Light Chain CDR2 amino acid sequence

<400> SEQUENCE: 86

Ala Ala Ser Ser Leu Gln Gly
1               5

<210> SEQ ID NO 87
<211> LENGTH: 9
<212> TYPE: PRT
<213> ORGANISM: Homo sapiens
<220> FEATURE:
<221> NAME/KEY: MISC_FEATURE
<223> OTHER INFORMATION: Ab1 Light Chain CDR3 amino acid sequence

<400> SEQUENCE: 87

Gln Gln Ser Tyr Ser Thr Pro Trp Thr
1               5

<210> SEQ ID NO 88
<211> LENGTH: 9
<212> TYPE: PRT
<213> ORGANISM: Homo sapiens
<220> FEATURE:
<221> NAME/KEY: MISC_FEATURE
<223> OTHER INFORMATION: Ab2 Light Chain CDR3 amino acid sequence

<400> SEQUENCE: 88

Gln Gln Ser Tyr Ser Thr Pro Trp Thr
1               5

<210> SEQ ID NO 89
<211> LENGTH: 9
<212> TYPE: PRT
<213> ORGANISM: Homo sapiens
<220> FEATURE:
<221> NAME/KEY: MISC_FEATURE
<223> OTHER INFORMATION: Ab3 Light Chain CDR3 amino acid sequence
```

```
<400> SEQUENCE: 89

Gln Gln Tyr Gly Ile Ser Pro Cys Ser
1               5

<210> SEQ ID NO 90
<211> LENGTH: 9
<212> TYPE: PRT
<213> ORGANISM: Homo sapiens
<220> FEATURE:
<221> NAME/KEY: MISC_FEATURE
<223> OTHER INFORMATION: Ab4 Light Chain CDR3 amino acid sequence

<400> SEQUENCE: 90

Ile Gln Thr Leu Gln Thr Pro Phe Thr
1               5

<210> SEQ ID NO 91
<211> LENGTH: 10
<212> TYPE: PRT
<213> ORGANISM: Homo sapiens
<220> FEATURE:
<221> NAME/KEY: MISC_FEATURE
<223> OTHER INFORMATION: Ab5 Light Chain CDR3 amino acid sequence

<400> SEQUENCE: 91

Leu Gln Ser Gly Ser Ser Val Pro Leu Thr
1               5                   10

<210> SEQ ID NO 92
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab6 Light Chain CDR3 amino acid sequence

<400> SEQUENCE: 92

Ala Ala Trp Asp Asp Ser Leu Ser Gly Val Val
1               5                   10

<210> SEQ ID NO 93
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab7 Light Chain CDR3 amino acid sequence

<400> SEQUENCE: 93

Gln Ser Tyr Asp Thr Ser Leu Ser Ala Ser Val
1               5                   10

<210> SEQ ID NO 94
<211> LENGTH: 9
<212> TYPE: PRT
<213> ORGANISM: Homo sapiens
<220> FEATURE:
<221> NAME/KEY: MISC_FEATURE
<223> OTHER INFORMATION: Ab8 Light Chain CDR3 amino acid sequence

<400> SEQUENCE: 94

Gln Gln Tyr Tyr Asn Tyr Pro Phe Thr
1               5
```